US009662086B2

(12) United States Patent
Ohta et al.

(10) Patent No.: US 9,662,086 B2
(45) Date of Patent: May 30, 2017

(54) RADIOGRAPHIC IMAGE CAPTURING APPARATUS

(71) Applicant: FUJIFILM Corporation, Tokyo (JP)

(72) Inventors: Yasunori Ohta, Kanagawa (JP); Naoyuki Nishino, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 14/606,627

(22) Filed: Jan. 27, 2015

(65) Prior Publication Data

US 2015/0164462 A1 Jun. 18, 2015

Related U.S. Application Data

(63) Continuation of application No. 13/729,536, filed on Dec. 28, 2012, which is a continuation of application No. PCT/JP2011/066405, filed on Jul. 20, 2011.

(30) Foreign Application Priority Data

Jul. 26, 2010 (JP) ................................. 2010-167255
Jul. 26, 2010 (JP) ................................. 2010-167257

(51) Int. Cl.
*A61B 6/00* (2006.01)
*A61B 5/00* (2006.01)
(52) U.S. Cl.
CPC ............ *A61B 6/563* (2013.01); *A61B 5/0059* (2013.01); *A61B 6/4405* (2013.01); *A61B 6/4411* (2013.01); *A61B 6/461* (2013.01); *A61B 6/48* (2013.01); *A61B 6/548* (2013.01); *A61B 6/587* (2013.01); *A61B 6/588* (2013.01); *A61B 6/4233* (2013.01); *A61B 6/4291* (2013.01); *A61B 6/542* (2013.01)

(58) Field of Classification Search
CPC .......... A61B 6/582; A61B 6/585; A61B 6/08; A61B 6/4233; A61B 6/587
See application file for complete search history.

(56) References Cited

U.S. PATENT DOCUMENTS 7,874,729 B2    1/2011  Okuno et al.
2003/0194056 A1*  10/2003  Spahn .................... A61B 6/08
                                                378/205

(Continued)

FOREIGN PATENT DOCUMENTS

CN    1575769 A    2/2005
CN    201422883 Y    3/2010

(Continued)

OTHER PUBLICATIONS

Rejection of the Application issued by the JPO on Oct. 29, 2013, in connection with corresponding Japanese Patent Application No. 2010-167255.

(Continued)

*Primary Examiner* — Hoon Song
(74) *Attorney, Agent, or Firm* — Edwards Neils LLC; Jean C. Edwards, Esq.

(57) ABSTRACT

The radiographic imaging device that configures the disclosed radiographic imaging system has at least a camera that images a main cassette body. Said camera is integrally configured to a radiation source and a control device that controls the main cassette body or is integrally configured to a main radiation source body that houses the radiation source.

10 Claims, 41 Drawing Sheets

(56) References Cited

U.S. PATENT DOCUMENTS

| | | | |
|---|---|---|---|
| 2005/0058257 A1 | 3/2005 | Fischer et al. | |
| 2005/0100134 A1 | 5/2005 | Bauer et al. | |
| 2005/0111620 A1 | 5/2005 | Livermore et al. | |
| 2007/0049815 A1 | 3/2007 | Sanjay-Gopal et al. | |
| 2009/0046828 A1* | 2/2009 | Ohta | A61B 6/00 378/1 |
| 2009/0136000 A1* | 5/2009 | Nishii | A61B 6/08 378/98.3 |
| 2011/0049370 A1 | 3/2011 | Yoshida et al. | |
| 2011/0286579 A1 | 11/2011 | Butzine et al. | |

FOREIGN PATENT DOCUMENTS

| | | |
|---|---|---|
| JP | 08-266535 A | 10/1996 |
| JP | 11-104117 A | 4/1999 |
| JP | 2003-093354 A | 4/2003 |
| JP | 2005-261525 A | 9/2005 |
| JP | 2007-507035 A | 3/2007 |
| JP | 2008-104703 A | 5/2008 |
| JP | 2008-125981 A | 6/2008 |
| JP | 2008-206740 A | 9/2008 |
| JP | 2009-028367 A | 2/2009 |
| JP | 2010-161624 A | 7/2010 |
| JP | 2011-045439 A | 3/2011 |

OTHER PUBLICATIONS

Rejection of the Application, issued by the Japanese Patent Office (JPO) on Mar. 25, 2014, in connection with Japanese Patent Application No. 2010-167257.

Chinese Office Action, dated Sep. 24, 2014, issued by the Chinese Patent Office in the corresponding Chinese Patent Application No. 201180033017.1.

Non-Final Office Action Issued in parent U.S. Appl. No. 13/729,536 by the USPTO on Aug. 19, 2014.

Final Office Action Issued in parent U.S. Appl. No. 13/729,536 by the USPTO on Dec. 10, 2014.

Final Office Action issued by the US Patent and Trademark Office (USPTO) on Jan. 14, 2016 in connection with U.S. Appl. No. 13/729,536.

* cited by examiner ized as nationally licensed practitioners. In Japan, for example, persons who are legally permitted to engage in the business of applying radiation to a human body (to capture a radiographic image of the human body) are limited to doctors and dentists (hereinafter simply referred to as "doctors") and medical radiological technicians (hereinafter simply referred to as "radiological technicians") according to the Radiology Technicians Act. If a doctor or radiological technician who has legal authority concerning application of radiation to a subject is unable to go to a disaster site or a home care treatment site for some reason, then a person other than a doctor or radiological technician, i.e., a person who is not qualified as a medical radiological technician according to the Radiology Technicians Act (hereinafter referred to as an "operator"), may take a radiographic image capturing apparatus to the site and perform a preparatory procedure to make the radiographic image capturing apparatus ready to capture radiographic images, e.g., to position a body region to be imaged of the subject with respect to a cassette device of the radiation detector. However, such an operator is not legally permitted to capture radiographic images of the subject with the radiographic image capturing apparatus. According to the present practice, a qualified person such as a doctor or radiological technician needs to go to the disaster site or the home care treatment site in order to capture radiographic images of the subject with the radiographic image capturing apparatus.

RADIOGRAPHIC IMAGE CAPTURING APPARATUS

CROSS-REFERENCE TO RELATED APPLICATIONS AND PRIORITY CLAIMS

This application is a continuation application of U.S. patent application Ser. No. 13/729,536, filed on Dec. 28, 2012, which in turn is a Continuation of International Application No. PCT/JP2011/066405 filed on Jul. 20, 2011, which was published under PCT Article 21(2) in Japanese, which is based upon and claims the benefit of priority from Japanese Patent Applications No. 2010-167255 filed on Jul. 26, 2010, and No. 2010-167257 filed on Jul. 26, 2010, the contents all of which are incorporated herein by reference.

TECHNICAL FIELD

The present invention relates to a radiographic image capturing apparatus (radiographic imaging device), a radiographic image capturing system (radiographic imaging system), and a radiographic image capturing method (radiographic imaging method) for applying radiation from a radiation source to a subject, detecting radiation that has passed through the subject with a radiation detector, and converting the detected radiation into a radiographic image.

BACKGROUND ART

In the medical field, there have widely been used radiographic image capturing apparatus, which apply radiation to a subject and guide radiation that has passed through the subject to a radiation conversion panel (radiation detector) in order to capture a radiographic image. Known forms of radiation conversion panels include a conventional radiographic film for recording a radiographic image by way of exposure, and a stimulable phosphor panel for storing radiation energy representing a radiographic image in a phosphor and emitting stimulated light representing the radiographic image if the stimulable phosphor panel is irradiated with stimulating light. The radiographic film with the recorded radiographic image is supplied to an image developing device, which develops the radiographic image. The stimulable phosphor panel is supplied to an image reading device, which reads the radiographic image from the stimulable phosphor panel as a visible image.

In an operating room or the like, it is necessary to read a recorded radiographic image immediately from a radiation conversion panel after the radiographic image has been captured for the purpose of quickly and appropriately treating the patient. As a radiation detector that meets such a requirement, there have been developed a radiation detector of a direct conversion type having a solid-state detector for converting radiation directly into an electric signal, and a radiation detector of an indirect conversion type having a scintillator for temporarily converting radiation into visible light and a solid-state detector for converting the visible light into an electric signal.

The radiation detector is housed in a radiation detecting cassette (cassette device), which is permeable to radiation. As disclosed in Japanese Laid-Open Patent Publication No. 2003-093354, such radiographic image capturing apparatus are developed on the assumption that they will be used in order to capture radiographic images of patients in hospitals.

There are potential demands for capturing radiographic images outside of hospitals. To meet such demands, radiographic image capturing apparatus, which are mounted on motor vehicles dedicated for medical checkups, have been proposed in the art (see Japanese Laid-Open Patent Publication No. 2008-206740). However, such proposed radiographic image capturing apparatus mounted on medical checkup motor vehicles are relatively large in size. Needs have arisen for capturing radiographic images of persons suffering from natural disasters at disaster sites, or persons who are receiving home-care services in their homes. However, existing medical checkup motor vehicles cannot be used in the former applications as it is difficult to get them to disaster sites. Although existing medical checkup motor vehicles may be driven to homes of persons who are receiving home-care services, i.e., home care treatment sites, the image capturing process is highly burdensome to people to be imaged, because such people have to be taken from their homes into the medical checkup motor vehicle in order to capture radiographic images. Therefore, there have been demands for small-size portable radiographic image capturing apparatus for use at natural disaster sites or homes receiving home-care services.

There has been developed a portable radiographic image capturing apparatus, which can be folded into a compact form as a whole, as disclosed in Japanese Laid-Open Patent Publication No. 11-104117.

SUMMARY OF INVENTION

Problems to be Solved by the Invention

If a radiographic image capturing apparatus is reduced in overall size and weight, it becomes easy to carry around. A doctor or radiological technician carries the radiographic image capturing apparatus to a disaster site or a home care treatment site. At the disaster site or the home care treatment site, the doctor or radiological technician assembles the radiographic image capturing apparatus and captures a radiographic image using the same.

Radiographic images can usually only be captured by doctors or similarly qualified persons who are author- To eliminate the above shortcomings, the technologies disclosed in Japanese Laid-Open Patent Publication No. 2003-093354 and Japanese Laid-Open Patent Publication No. 2008-206740 may be applied in order to capture radiographic images of a subject, according to instructions from a doctor or a radiological technician who remains in a waiting location (e.g., a medical organization or a medical checkup motor vehicle) where the doctor or radiological technician cannot see the subject directly.

According to the technology disclosed in Japanese Laid-Open Patent Publication No. 2003-093354, an image (radiographic image) of an affected region of an emergency patient (subject) who has been carried into a medical organization is sent to the mobile terminal of a doctor who is not available at the medical organization, and the doctor is asked to give instructions as to a next radiographic image to be captured of the emergency patient. If the technology disclosed in Japanese Laid-Open Patent Publication No. 2003-093354 is applied directly, then the image of the affected region of the emergency patient, which is sent to the mobile terminal of the doctor in order to seek the doctor's instructions as to a next radiographic image to be captured, may possibly be a radiographic image that has been captured without the approval of the doctor. In addition, since the image of the affected region of the emergency patient needs to be sent to the mobile terminal of the doctor in order to seek the doctor's instructions as to a next radiographic image to be captured, the doctor is unable to instruct a person at the site how to capture a radiographic image of the patient in real time.

According to the technology disclosed in Japanese Laid-Open Patent Publication No. 2008-206740, the exposure of a subject to radiation is interrupted based on an optical image representing a body movement of the subject. Even if the technology disclosed in Japanese Laid-Open Patent Publication No. 2008-206740 were applied directly, the doctor is unable to instruct a person at the site to capture a radiographic image of the patient in real time.

Object of Invention

The present invention has been made in view of the above problems. It is an object of the present invention to provide a radiographic image capturing apparatus, a radiographic image capturing system, and a radiographic image capturing method, which are capable of capturing an image of a subject without requiring a doctor or a radiological technician to travel directly to a disaster site or a home care treatment site.

Configurations of Invention

To achieve the aforementioned objects, a radiographic image capturing apparatus according to the present invention comprises:
- a radiation source for outputting radiation;
- a radiation detector for detecting radiation that has passed through a subject and converting the detected radiation into a radiographic image upon application of the radiation to the subject from the radiation source;
- a cassette device that is permeable to the radiation and accommodates the radiation detector therein;
- a camera for capturing an image of at least the cassette device; and
- a camera image communication unit that transmits an image of the cassette device captured by the camera to a waiting location communication unit provided in a waiting location where a doctor or radiological technician having authority to apply the radiation to the subject waits while being unable to see the subject directly, wherein the camera is made integral with a controller for controlling the radiation source and the cassette device, or is made integral with a radiation source device accommodating the radiation source therein.

Further, in order to achieve the aforementioned objects, a radiographic image capturing system according to the present invention comprises:
- a radiographic image capturing apparatus having a radiation source for outputting radiation, a radiation detector for detecting radiation that has passed through a subject and converting the detected radiation into a radiographic image upon application of the radiation to the subject from the radiation source, a cassette device that is permeable to the radiation and accommodates the radiation detector therein, a camera for capturing an image of at least the cassette device, and a camera image communication unit that externally transmits an image of the cassette device captured by the camera; and
- a console and a waiting location communication unit which are disposed at a waiting location where a doctor or radiological technician having authority to apply the radiation to the subject waits while being unable to see the subject directly, the waiting location communication unit being adapted to receive an image of the cassette device from the camera image communication unit, the console being connected electrically to the waiting location communication unit, the image of the cassette device being input from the waiting location communication unit to the console, wherein the camera is made integral with a controller of the radiographic image capturing apparatus for controlling the radiation source and the cassette device, or is made integral with a radiation source device accommodating the radiation source therein.

Furthermore, in order to achieve the aforementioned objects, there is provided a radiographic image capturing method comprising the steps of:
- constructing a controller for controlling a cassette device, which accommodates a radiation detector therein, and a radiation source integrally with a camera, or constructing a radiation source device, which accommodates the radiation source therein, integrally with the camera;
- capturing an image of at least the cassette device with the camera;
- transmitting an image of the cassette device captured by the camera to a waiting location communication unit provided in a waiting location where a doctor or radiological technician having authority to apply the radiation to the subject waits while being unable to see the subject directly;
- in a case that a region to be imaged of the subject is included within the image of the cassette device transmitted to the waiting location communication unit, giving an instruction from the waiting location communication unit to the radiation source to emit the radiation, and thereby emitting the radiation from the radiation source and applying the radiation to the subject; and detecting radiation that has passed through the subject and the cassette device, and converting the detected radiation into a radiographic image, with the radiation detector.

Effect of Invention

According to the present invention, at a disaster site or a home care treatment site, the camera, which is constructed integrally with the controller or with the radiation source device, captures an image of at least the cassette device. The camera image communication unit transmits an image of the cassette device captured by the camera to the waiting location communication unit, which is disposed at the waiting location. Consequently, a doctor or radiological technician, who is waiting at the waiting location while unable to observe the subject directly, can provide instructions to an operator of the radiographic image capturing apparatus, who is currently at the disaster site or the home care treatment site, for capturing an image of the subject in real time, based on the image of the cassette device, which was received by the waiting location communication unit. Accordingly, image capturing can be carried out with respect to the subject, even though the doctor or radiological technician cannot travel directly to the disaster site or the home care treatment site.

DESCRIPTION OF EMBODIMENTS

A radiographic image capturing apparatus and a radiographic image capturing system including the radiographic image capturing apparatus, according to a preferred exemplary embodiment of the present invention, in relation to a radiographic image capturing method, will be described in detail below with reference to FIGS. 1 through 41B.

Configurations of Embodiments

Figure 1:
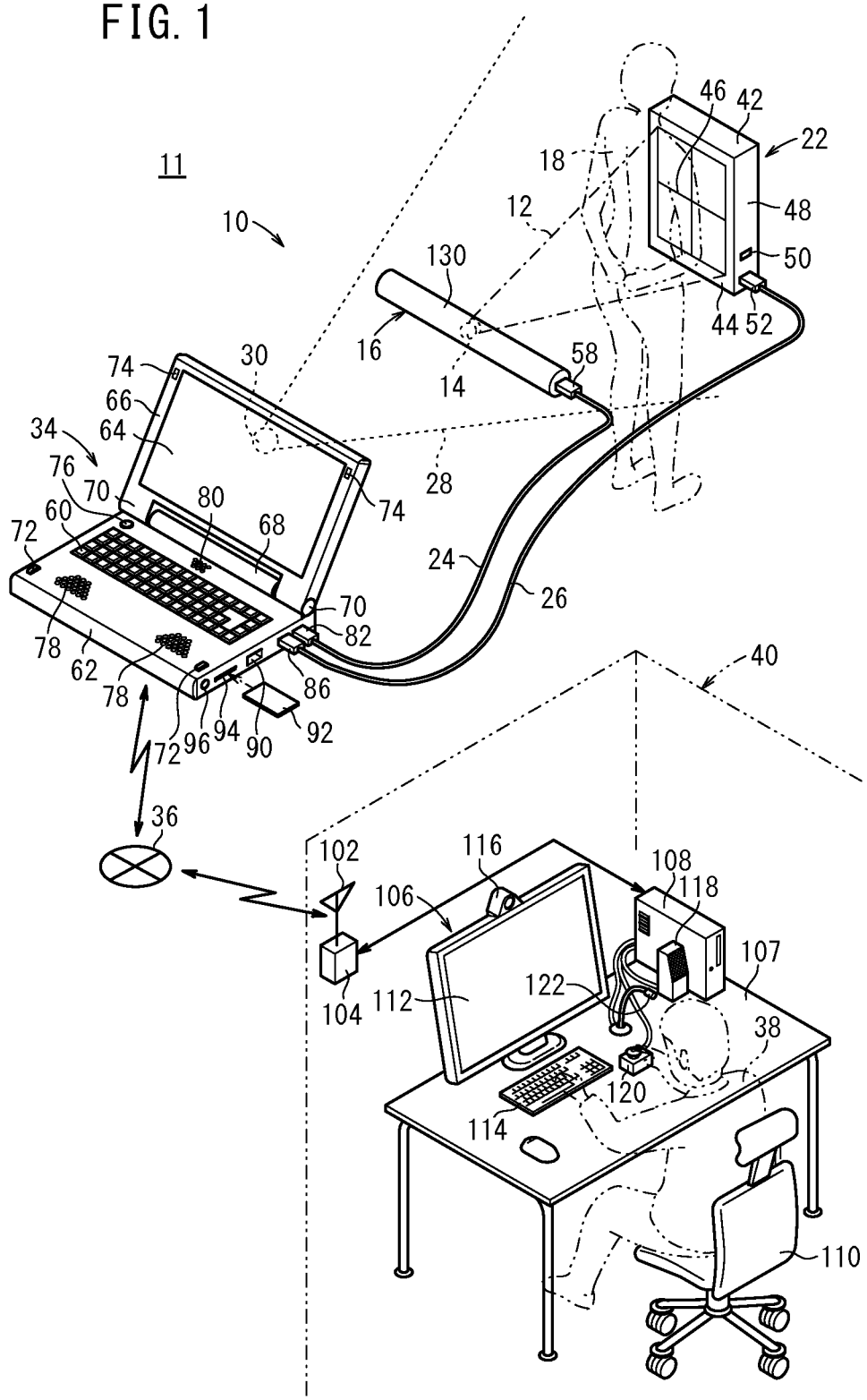
FIG. 1 is a perspective view of a radiographic image capturing apparatus and a radiographic image capturing system according to an exemplary embodiment of the present invention.
Figure 2:
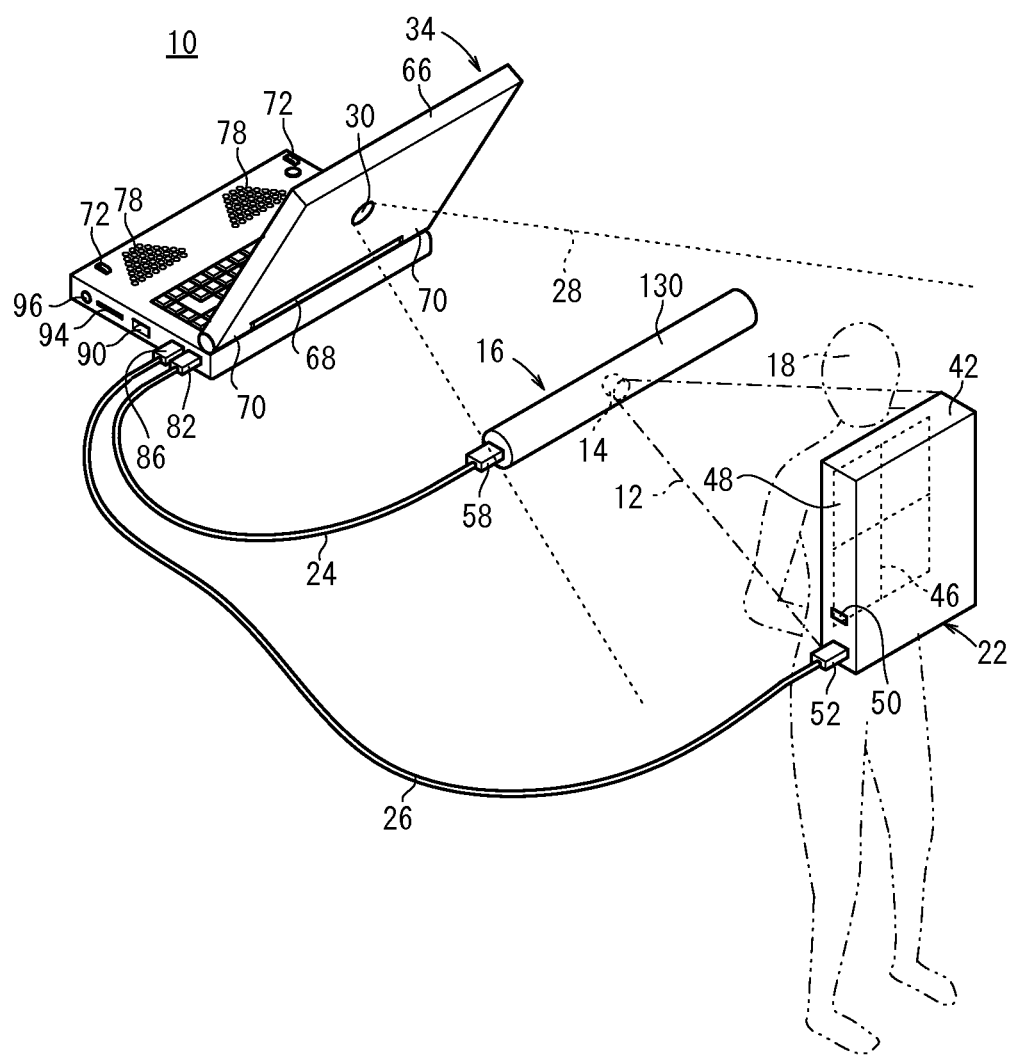
FIG. 2 is a perspective view of the radiographic image capturing apparatus shown in FIG. 1.

As shown in FIGS. 1 and 2, a radiographic image capturing system 11 according to the present exemplary embodiment includes a radiographic image capturing apparatus 10. The radiographic image capturing apparatus 10 has a radiation source device 16, a cassette device 22, and a portable information terminal 34 (controller, PC).

The radiation source device 16 houses therein a radiation source 14 for emitting radiation 12, and is made of a material that is permeable to radiation 12. The cassette device 22 houses therein a radiation detector 20 (see FIGS. 3 and 4) for converting radiation 12 that has passed through a subject 18 into a radiographic image, and is made of a material that is permeable to radiation 12. The portable information terminal (controller, PC) 34 is electrically connected through a USB cable 24 to the radiation source device 16, and is electrically connected through a USB cable 26 to the cassette device 22. Further, the portable information terminal 34 accommodates therein a web camera 30 for capturing an image of a prescribed image capturing region 28, and serves as a portable terminal which can be operated by an operator 32 (see FIG. 5) of the radiographic image capturing apparatus 10. In this case, the portable information terminal 34 is capable of sending signals to and receiving signals from a medical organization 40 (waiting location) to which a doctor (or radiological technician) 38 belongs, via a network 36 such as a public network or the like by way of wireless communications.

Radiographic images can usually be captured only by doctors or similarly qualified persons who are authorized as nationally licensed practitioners. The operator 32 refers to a person who is not qualified as a medical radiological technician according to the Radiology Technicians Act of Japan, or more specifically, a person other than doctors and dentists (hereinafter simply referred to as "doctors") and medical radiological technicians (hereinafter simply referred to as "radiological technicians") who have legal authority to apply radiation 12 to the subject 18.

Further, according to the present exemplary embodiment, the subject 18 is present at a disaster site or a home care treatment site, whereas the doctor (or radiological technician) 38 is present (waits) in a (remote) medical organization 40 where the doctor 38 is unable to see the subject 18 directly. The doctor 38 is unable to go to the disaster site or the home care treatment site for certain reasons, whereas the operator 32 travels to the disaster site or the home care treatment site in lieu of the doctor 38. Hereinafter, reference numeral 38 will be used to represent a doctor.

Figure 7:
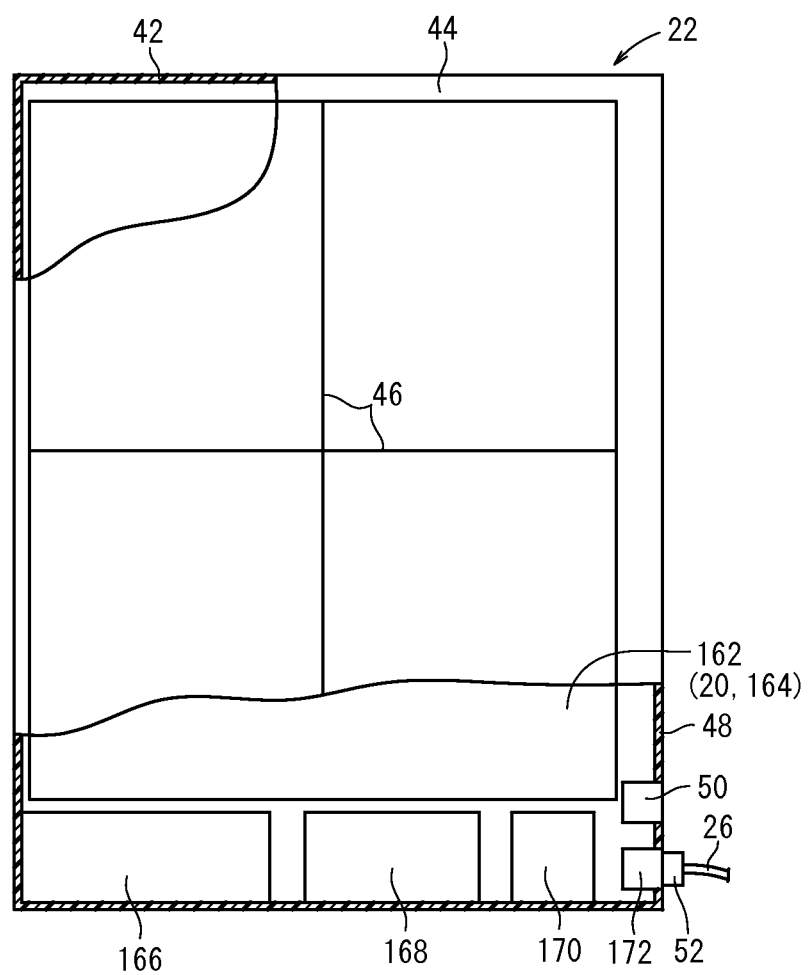
FIG. 7 is a plan view of a cassette device shown in FIGS. 1 and 2.

As shown in FIGS. 1 through 4 and 7, the cassette device 22 includes a substantially rectangular housing 42 made of a material permeable to radiation 12. The housing 42 includes a surface, referred to as an irradiated surface 44, which faces toward the radiation source device 16 and is irradiated with radiation 12. The cassette device 22 is formed with guide lines 46 disposed within an irradiated area (irradiated field), which is irradiated with radiation 12, of the irradiated surface 44, and which serves as a reference for an image capturing area and an image capturing position. The guide lines 46 provide an outer frame (irradiated field of radiation 12), which as shown in FIG. 7, is substantially aligned with the outer edge of the radiation detector 20 as viewed in plan. Further, on one side surface 48 of the housing 42, a switch 50 is arranged for activating the cassette device 22, and a connector 52 of the USB cable 26 is connected thereto.

Figure 3:
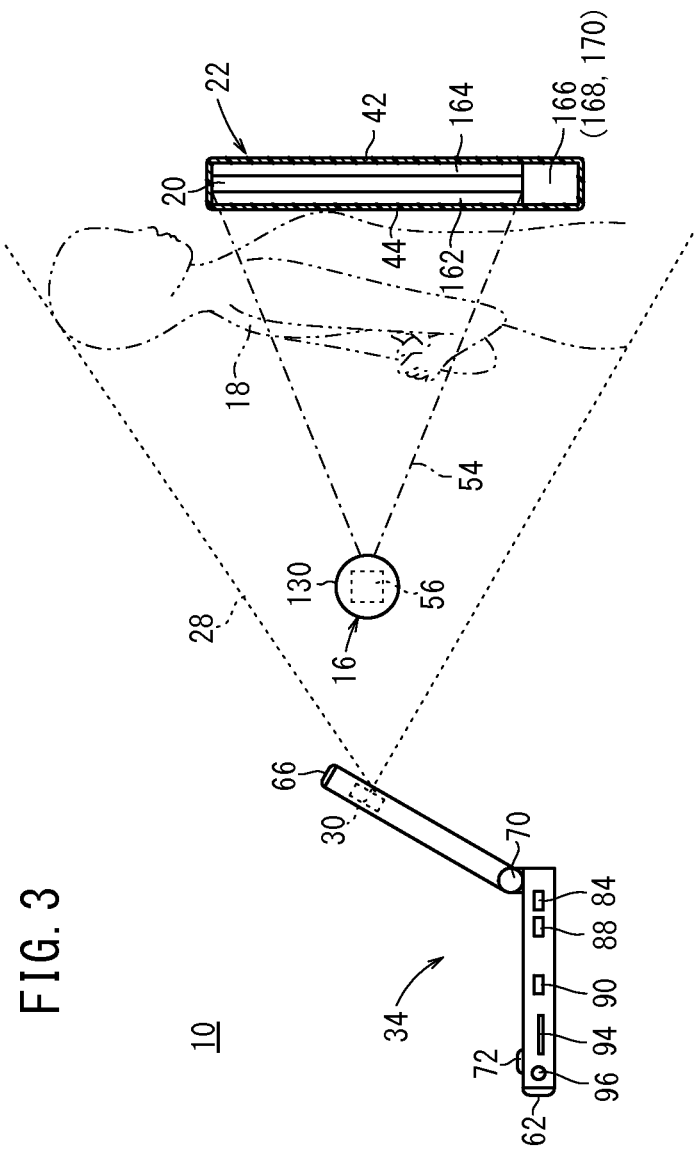
FIG. 3 is a side elevational view of the radiographic image capturing apparatus shown in FIGS. 1 and 2.
Figure 6:
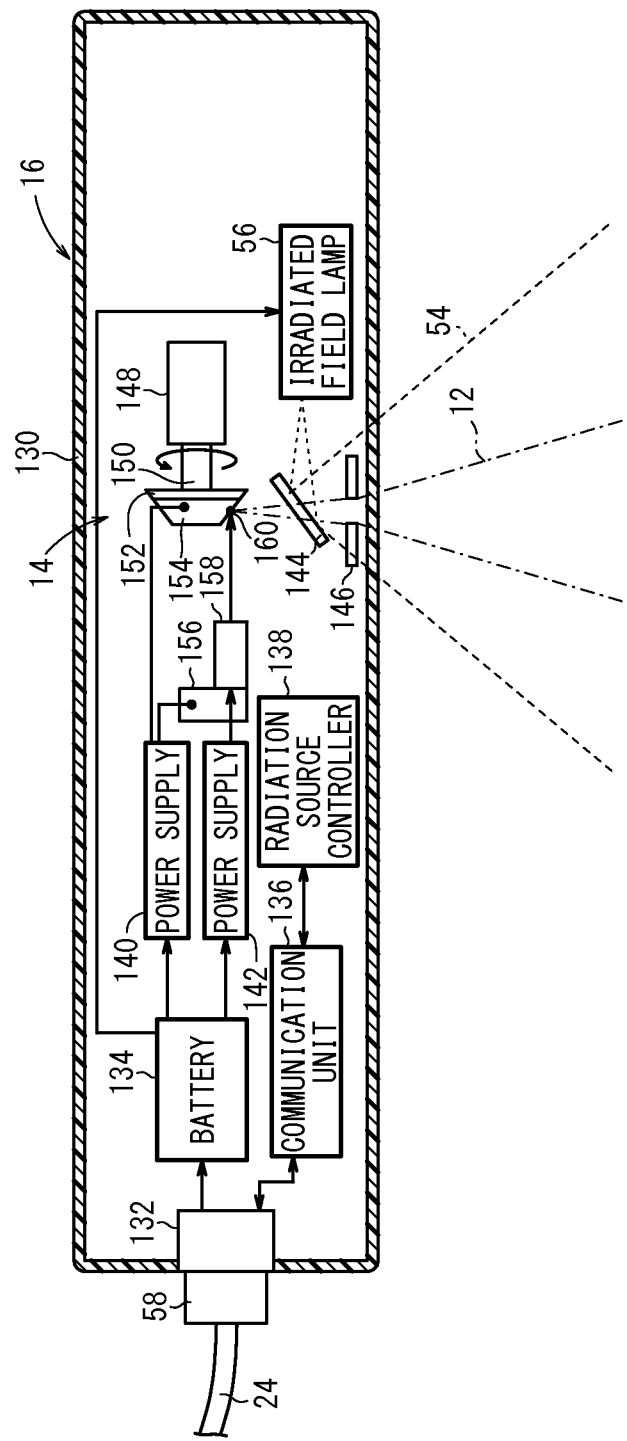
FIG. 6 is a view showing an internal structure of a radiation source device shown in FIG. 1.

As shown in FIGS. 3 and 6, the radiation source device 16 has a substantially cylindrical casing 130 made of a material permeable to radiation 12. In this case, the casing 130 of the radiation source device 16 houses therein, in addition to the radiation source 14, an irradiated field lamp 56 for emitting irradiation light 54. The irradiated field lamp 56 applies irradiation light 54 to the irradiated surface 44 before the radiation source 14 outputs radiation 12, thereby illuminating the irradiated field of the radiation 12 on the irradiated surface 44.

It is assumed that a straight line interconnecting a focus point 160, to be described later, of the radiation source 14 and a central position of the guide lines 46, i.e., a point of intersection between the criss-crossing guide lines 46, is substantially perpendicular to the irradiated surface 44 (see FIGS. 1, 2, and 7). If the distance (imaging distance) between the focus point 160 and the central position of the criss-crossing guide lines 46 is set to a source-to-image distance (SID), then the outer edge of the irradiated field, which is displayed on the irradiated surface 44 upon application of irradiation light 54 thereto, essentially is aligned with the outer frame of the guide lines 46. Further, the location of the casing 130 through which the irradiation light 54 passes preferably is made of a material permeable to the irradiation light 54, for example. Furthermore, as shown in FIGS. 1, 2 and 6, a connector 58 of the USB cable 24 is connected to a side surface of the casing 130.

As shown in FIGS. 1 through 4 and 16, the portable information terminal 34 comprises a notebook-sized personal computer (PC) including an operating unit 60 such as a keyboard, etc., disposed on an upper surface (facing a lid 66) of a main body 62, and a display unit 64 such as a display or the like is disposed on a lower surface (facing the operating unit 60) of the lid 66. With the present embodiment, a description is given of a notebook type portable information terminal 34. However, the portable information terminal 34 may be a different type of portable terminal having various functions, including the operating unit 60, the display unit 64, etc., such as a mobile phone or a PDA (personal information terminal).

Figure 16:
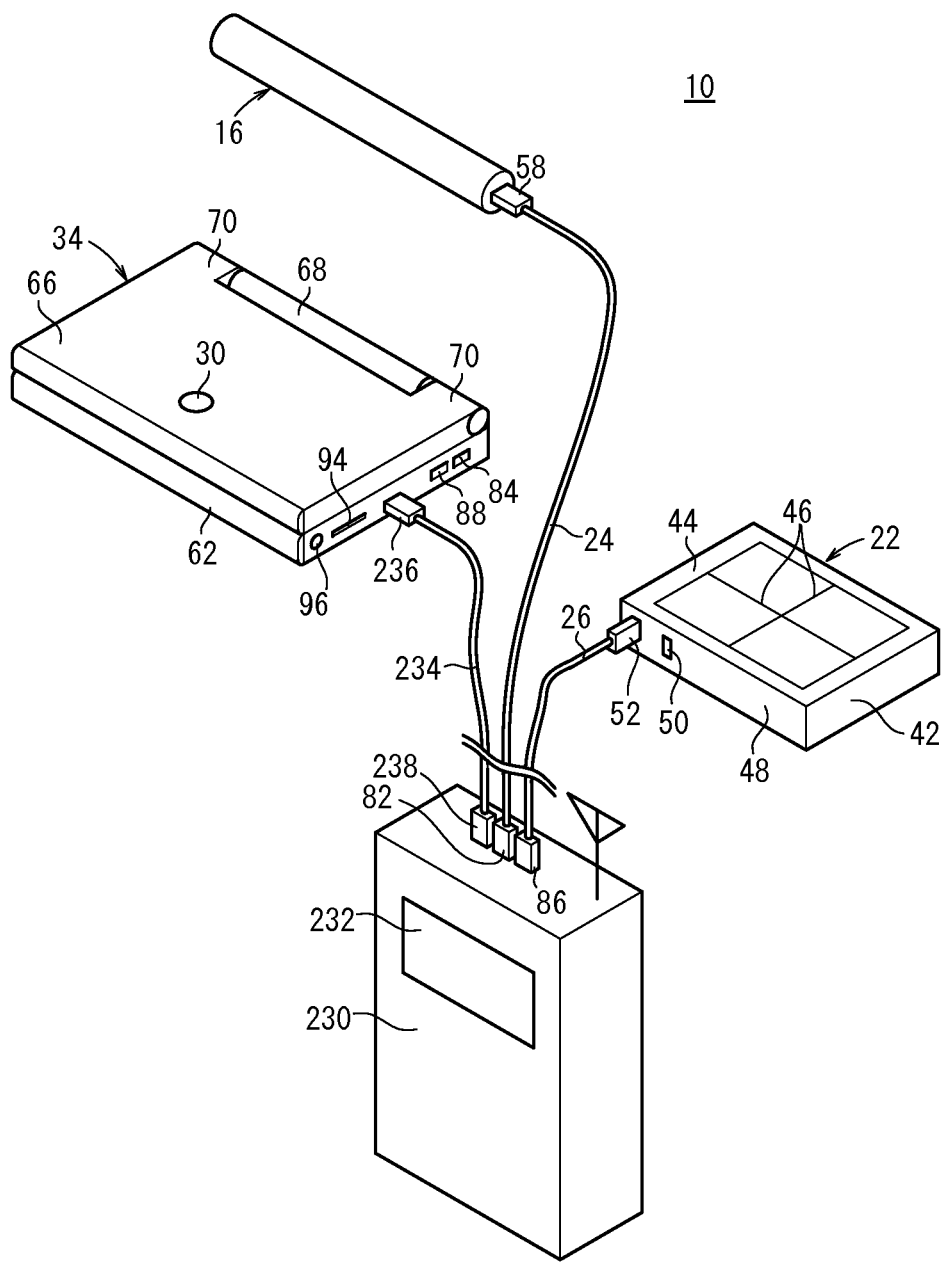
FIG. 16 is a perspective view showing a manner in which a portable information terminal, a radiation source device, and a cassette device are charged in a medical organization.

During times that the portable information terminal 34 is not in use, the main body 62 and the lid 66 are folded over one another about a shaft 68 on one side of the main body 62 and two hinges 70 connected to respective ends of the shaft 68, as shown in FIG. 16. The upper surface of the main body 62 has two teeth 72, and the lower surface of the lid 66 has two recesses 74 corresponding respectively to the two teeth 72. If the upper surface of the main body 62 and the lower surface of the lid 66 are brought into contact with each other at a time that the portable information terminal 34 is not in use, the teeth 72 are fitted respectively into the recesses 74, thereby keeping the main body 62 and the lid 66 folded over each other.

During times that the portable information terminal 34 is in use, the lid 66 is turned away from the main body 62 about the shaft 68 and the hinges 70, thereby unfolding the main body 62 and the lid 66 away from each other, from the folded position shown in FIG. 16 to the operational position shown in FIGS. 1 through 4.

On the upper surface of the main body 62 in the vicinity of the operating unit 60, there are provided a power supply switch 76 for activating the portable information terminal 34, speakers (audio output unit) 78 for outputting speech sounds, and a microphone 80 for detecting voices of the subject 18 and the operator 32.

Further, USB terminals 84, 88, 90, a card slot 94, and an AC adapter input terminal 96 are provided on a side surface of the main body 62. A connector 82 of the USB cable 24 is fitted into the USB terminal 84. A connector 86 of the USB cable 26 is fitted into the USB terminal 88. By fitting of a connector of a non-illustrated USB cable into the USB terminal 90, information can be transmitted to and received from an external device through the USB cable. A memory card 92 is cable of being mounted in the card slot 94.

On the other hand, on the upper surface of the lid 66, a web camera 30 is arranged as an optical camera. Accordingly, the web camera 30 is constructed integrally with the portable information terminal 34.

Integral construction between the web camera 30 and the portable information terminal 34 is not limited to the structures shown in FIGS. 1 through 4, in which the web camera 30 is incorporated in the portable information terminal 34, but includes a structure in which, at least at times that the radiographic image capturing apparatus 10 is in use, the web camera 30 and the portable information terminal 34 are joined (connected) together in an integral manner.

Therefore, the web camera 30 may be made integral with the portable information terminal 34 in any one of the following situations (1) through (3). (1) The web camera 30 is connected to the portable information terminal 34 by a cable, which is included in the radiographic image capturing apparatus 10. (2) The web camera 30 is connected to the portable information terminal 34 by a cable, which is provided by the operator 32. (3) During times that the radiographic image capturing apparatus 10 is in use, the portable information terminal 34 is coupled to the web camera 30, and during times that the radiographic image capturing apparatus 10 is serviced for maintenance or is not in use, the web camera 30 can be spaced (or separated) from the portable information terminal 34.

In order to enable the web camera 30 to be spaced from the portable information terminal 34 during times that the radiographic image capturing apparatus 10 is serviced for maintenance or is not in use, for example, the web camera 30 may be coupled to the portable information terminal 34 by a coupling means such as a clip or the like. The web camera 30 is coupled to the portable information terminal 34 by the coupling means only at times that the radiographic image capturing apparatus 10 is in use. Further, the coupling means may incorporate a ball joint to facilitate coupling of the web camera 30 to the portable information terminal 34 and to change the orientation thereof freely. If the web camera 30 is coupled to the portable information terminal 34 by way of such a coupling means, the web camera 30 and the portable information terminal 34 must be connected to each other through a wired link (e.g., a USB cable) or a wireless link.

If the web camera 30 and the portable information terminal 34 are connected to each other by a cable, then since the web camera 30 can independently be placed in a desired position within the range permitted by the length of the cable, the web camera 30 can be positioned with greater freedom than if the web camera 30 were incorporated in the portable information terminal 34.

Concerning the web camera 30, by turning the lid 66 with respect to the main body 62, the upper surface of the lid 66 is made to face toward the cassette device 22, the radiation source device 16, and the subject 18, and further, if the operator 32 turns on the power supply switch 76 thereby energizing the portable information terminal 34, an image is captured as an image capturing region 28 at least of the irradiated region (region within the guide lines 46) of the radiation 12. More preferably, as shown in FIGS. 1 through 4, in a state in which the subject 18 is positioned between the radiation source device 16 and the cassette device 22, the web camera 30 captures as an image capturing region 28 a predetermined region including the radiation source device 16, the subject 18, and the cassette device 22.

In this case, the web camera 30 continuously captures an optical image of the image capturing region 28, and outputs a camera image (moving image) which is representative of the continuously captured optical image. The web camera 30 can also (intermittently) capture optical images of the image capturing region 28 at given time intervals, and output a camera image (still image) representative of the intermittently captured optical image or a camera image (still image) captured at a certain time.

Figure 5:
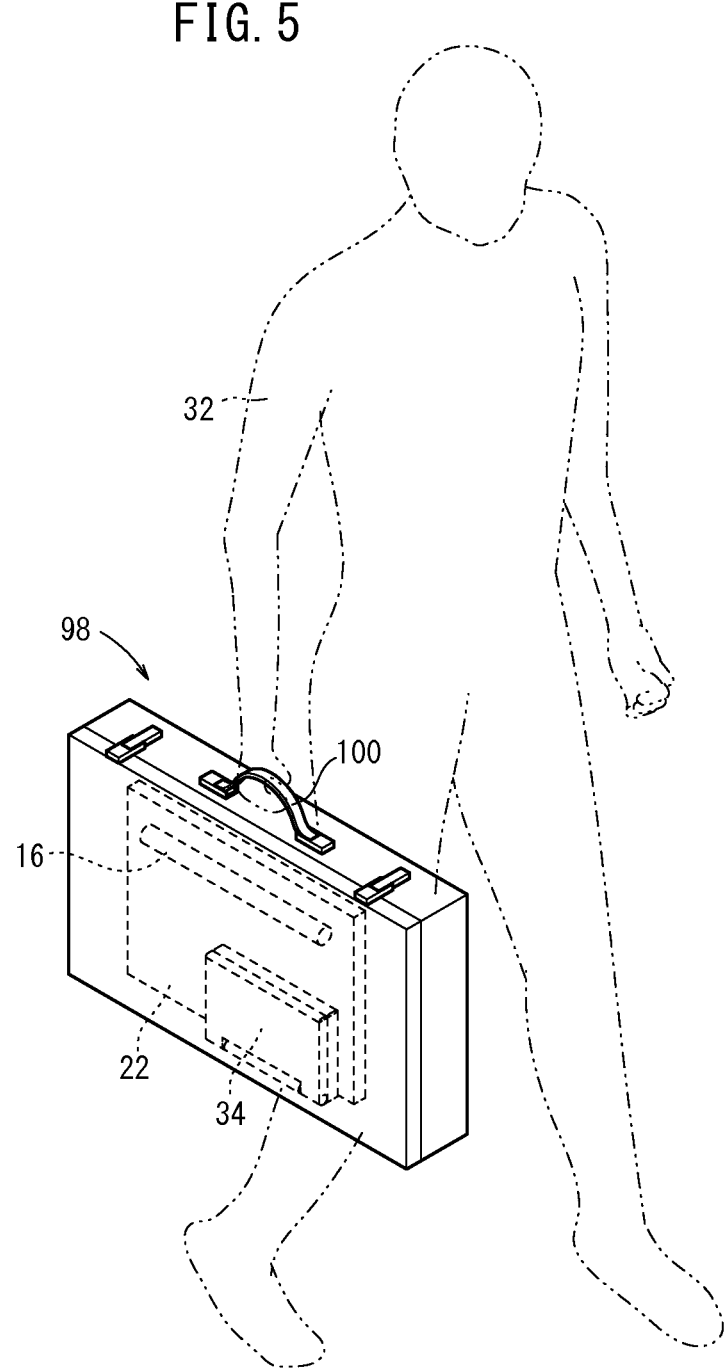
FIG. 5 is a perspective view showing the manner in which the radiographic image capturing apparatus shown in FIGS. 1 and 2 is carried.

FIG. 5 shows a state of the radiographic image capturing apparatus 10, at a time that the radiographic image capturing apparatus 10 is carried by the operator 32.

During times that the radiographic image capturing apparatus 10 is carried by the operator 32, the radiation source device 16, the cassette device 22, and the folded portable information terminal 34 are housed in an attaché case 98, in a state in which the connectors 52, 58, 82, 86 (see FIGS. 1 and 2) are taken out, and the electrical connections by the USB cables are disconnected. Thus, the operator 32 can grip the handle 100 and carry the attaché case 98 from the medical organization 40 to a desired location, e.g., a disaster site or a home care treatment site. Accordingly, at the location where the attaché case 98 is carried, the operator 32 can remove the radiation source device 16, the cassette device 22, and the folded portable information terminal 34 from the attaché case 98, and assemble these components into the configuration shown in FIGS. 1 through 4. The operator 32 can then perform a preparatory procedure in order to ready the radiographic image capturing apparatus 10 for capturing radiographic images of a disaster victim at a disaster site or a home-care-service recipient at a home care treatment site.

In this manner, the radiographic image capturing apparatus 10 according to the present exemplary embodiment can be referred to as a portable radiographic image capturing apparatus, in which the web camera 30 and the portable information terminal 34 are made integral with each other. The disaster victim or the home-care-service recipient, who is a subject to be imaged in order to produce a radiographic image thereof, will hereinafter be referred to as the subject 18.

Returning to FIG. 1, the medical organization 40 includes a communication unit (waiting location communication unit, wireless communication unit) 104 having an antenna 102 for sending signals to and receiving signals from the portable information terminal 34 via the network 36 by way of wireless communications. A console 106 is electrically connected to the communication unit 104.

The console 106 is connected to a radiology information system (RIS), not shown, which generally manages radiographic images and other information that are handled in a radiological department of the medical organization 40. The RIS is connected to a hospital information system (HIS), not shown, which generally manages medical information in the medical organization 40.

The console 106 is placed on a desk 107 in a room where a doctor 38 in the medical organization 40 is present.

The console 106 comprises a main body 108 for carrying out various processing sequences, a display unit 112, an operating unit 114, a web camera 116, a speaker 118 for outputting speech sounds, an exposure switch 120, and a microphone 122 capable of inputting the voice of the doctor 38 thereto.

The display unit 112 is a display for displaying predetermined images and information for the doctor 38, who is seated in a chair 110 at the desk 107. The operating unit 114 is a keyboard or the like, which is operated by the doctor 38. The web camera 116 is mounted on an upper end of the display unit 112 for capturing an image of the doctor 38. The exposure switch 120 can be turned on by the doctor 38 in order to initiate emission of radiation 12 from the radiation source 14.

As described above, the portable information terminal 34 and the communication unit 104 send signals to and receive signals from each other via the network 36 by way of wireless communications.

For this purpose, the portable information terminal 34 is capable of sending camera images output from the web camera 30, a radiographic image supplied via the USB cable 26 from the cassette device 22 (radiation detector 20), and voice signals representative of voices of the operator 32 or the subject 18 input to the microphone 80, through the antenna 102 of the medical organization 40 to the communication unit 104 via the network 36 by way of wireless communications.

On the other hand, the communication unit 104 is capable of sending a camera image (a moving image, still images captured intermittently, or still images captured at predetermined times) of the doctor 38 captured by the web camera 116, an exposure control signal generated in the main body 108 based on the doctor 38 turning on the exposure switch 120, and a voice signal representing the voice of the doctor 38 input to the microphone 122, to the portable information terminal 34 via the antenna 102 and the network 36 by way of wireless communications.

The display unit 64 of the portable information terminal 34 is capable of displaying at least one of a camera image of the image capturing region 28 captured by the web camera 30, a radiographic image from the radiation detector 20, and a camera image of the doctor 38 captured by the web camera 116. The display unit 64 also is capable of displaying information (character information) corresponding to the voice and exposure control signals referred to above. Moreover, the speakers 78 are capable of outputting the voice of the doctor 38, and a sound that depends on the exposure control signal (an alarm sound indicative of the start of emission of radiation 12 from the radiation source 14).

The portable information terminal 34 sends a synchronization control signal, which is generated based on the exposure control signal, to the radiation source device 16 and the cassette device 22 via the USB cables 24, 26, for thereby synchronizing (start of) emission of radiation 12 from the radiation source 14 and detection and conversion of radiation 12 into a radiographic image in the radiation detector 20 with each other.

On the other hand, on the console 106, similar to the case of the display unit 64, the display unit 112 is capable of displaying at least one of a camera image in the image capturing region 28 captured by the web camera 30, a radiographic image from the radiation detector 20, and a camera image of the doctor 38 captured by the web camera 116. The display unit 112 also is capable of displaying information (character information) corresponding to the voice and exposure control signals referred to above. Moreover, the speaker 118 is capable of outputting voices of the operator 32 or the subject 18 and sounds depending on the exposure control signal.

Internal structural details of the radiation source device 16 and the cassette device 22 will be described in specific detail below with reference to FIGS. 6 through 9.

As shown in FIG. 6, in the interior of the radiation source device 16, there are accommodated the radiation source 14, the irradiated field lamp 56, the USB terminal 132 in which the connector 58 of the USB cable 24 is fitted, a battery 134, a communication unit (radiation source communication unit) 136, a radiation source controller 138 for controlling the radiation source 14, a mirror 144 made of a material permeable to radiation 12, and a collimator 146, which is made of a material impermeable to radiation 12 but is permeable to the irradiation light 54. The battery 134 can be charged from an external source (e.g., the portable information terminal 34) via the USB cable 24, the connector 58, and the USB terminal 132, and is capable of supplying electric power to various components in the radiation source device 16.

The radiation source 14 comprises a field-emission-type radiation source.

More specifically, the radiation source 14 includes a disk-shaped rotary anode 152 mounted on a rotational shaft 150, which can be rotated about its axis through a rotating mechanism 148, an annular target layer 154 disposed on the surface of the rotary anode 152 and which is made mainly of a metallic element such as Mo or the like, a cathode 156 disposed in confronting relation to the rotary anode 152, and a field-emission-type electron source 158 disposed on the cathode 156 in confronting relation to the target layer 154.

The radiation source controller 138 controls the radiation source 14 in order to output radiation 12 according to a synchronization control signal based on an exposure control signal, which is received from the portable information terminal 34 (see FIGS. 1 through 5) via the USB cable 24, the connector 58, the USB terminal 132, and the communication unit 136.

More specifically, the radiation source 14 is controlled by the radiation source controller 138 to output radiation 12 in the following manner. The rotating mechanism 148 rotates the rotational shaft 150 to thereby rotate the rotary anode 152. The battery 134 supplies electric power to a power supply 142, which applies a voltage (negative voltage) to the field-emission-type electron source 158. The battery 134 also supplies electric power to a power supply 140, which applies a voltage between the rotary anode 152 and the cathode 156, i.e., the power supply 140 applies a positive voltage to the rotary anode 152 and a negative voltage to the cathode 156.

The field-emission-type electron source 158 emits electrons, which are accelerated to bombard the target layer 154 under the voltage applied between the rotary anode 152 and the cathode 156. The bombarded surface (focus point 160) of the target layer 154 emits radiation 12 at an intensity level depending on the applied electrons. Radiation 12 passes through the mirror 144, the irradiation area thereof is constricted by the collimator 146, and radiation 12 is output from the radiation source device 16.

Until the radiation source controller 138 is supplied with the synchronization control signal from the portable information terminal 34, the radiation source controller 138 controls the irradiated field lamp 56 in order to emit irradiation light 54. The irradiation light 54 emitted from the irradiated field lamp 56 is reflected by the mirror 144 in the direction of the collimator 146, and is output from the radiation source device 16.

Figure 4:
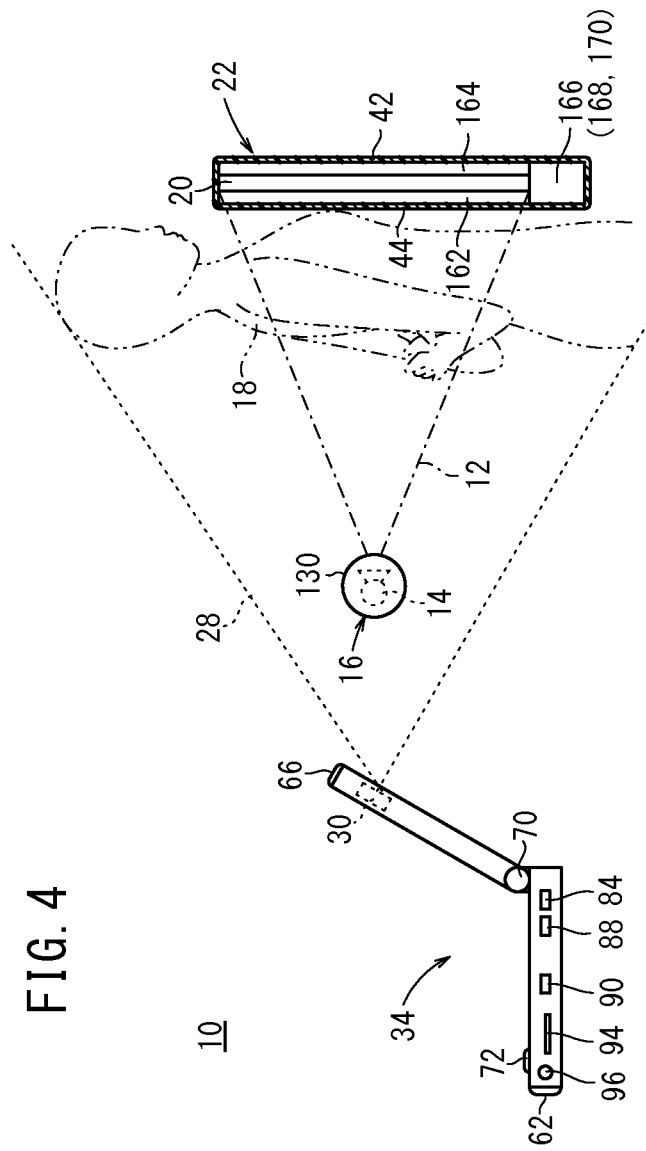
FIG. 4 is a side elevational view of the radiographic image capturing apparatus shown in FIGS. 1 and 2.

As shown in FIGS. 3, 4 and 7, the cassette device 22 houses therein a grid 162 for removing scattered rays of radiation 12 from the subject 18 if the radiation source 14 applies radiation 12 to the subject 18, the radiation detector 20, and a lead plate 164 for absorbing back scattered rays of radiation 12, which are successively arranged in this order from the irradiated surface 44 of the cassette device 22, which faces toward the subject 18. The irradiated surface 44 of the cassette device 22 may be constructed as the grid 162.

The radiation detector 20 may comprise an indirect conversion type of radiation detector including a scintillator for converting radiation 12 having passed through the subject 18 into visible light, and solid-state detectors (hereinafter also referred to as pixels) made of amorphous silicon (a-Si) or the like for converting visible light into electric signals, or a direct conversion type of radiation detector comprising solid-state detectors made of amorphous selenium (a-Se) or the like for converting the dose of radiation 12 directly into electric signals.

The aforementioned switch 50 and the USB terminal 172 with which the connector 52 of the USB cable 26 is fitted are disposed on the side surface 48 of the cassette device 22.

Furthermore, the cassette device 22 also houses therein a battery 166, a cassette controller 168, and a communication unit 170.

The battery 166, which is chargeable from an external device (e.g., the portable information terminal 34) through the USB cable 26, the connector 52 and the USB terminal 172, supplies electric power to various components (the radiation detector 20, the cassette controller 168, the communication unit 170) of the cassette device 22. The cassette controller 168 controls the radiation detector 20 with electric power supplied from the battery 166. The communication unit 170 sends and receives signals, including information of the radiation 12 detected by the radiation detector 20, to and from the portable information terminal 34 by way of the USB terminal 172, the connector 52, and the USB cable 26.

A plate of lead or the like preferably is placed over the side surfaces of the cassette controller 168 and the communication unit 170 under the irradiated surface 44, so as to protect the cassette controller 168 and the communication unit 170 against damage, which otherwise would be caused if these components were irradiated with radiation 12.

Figure 8:
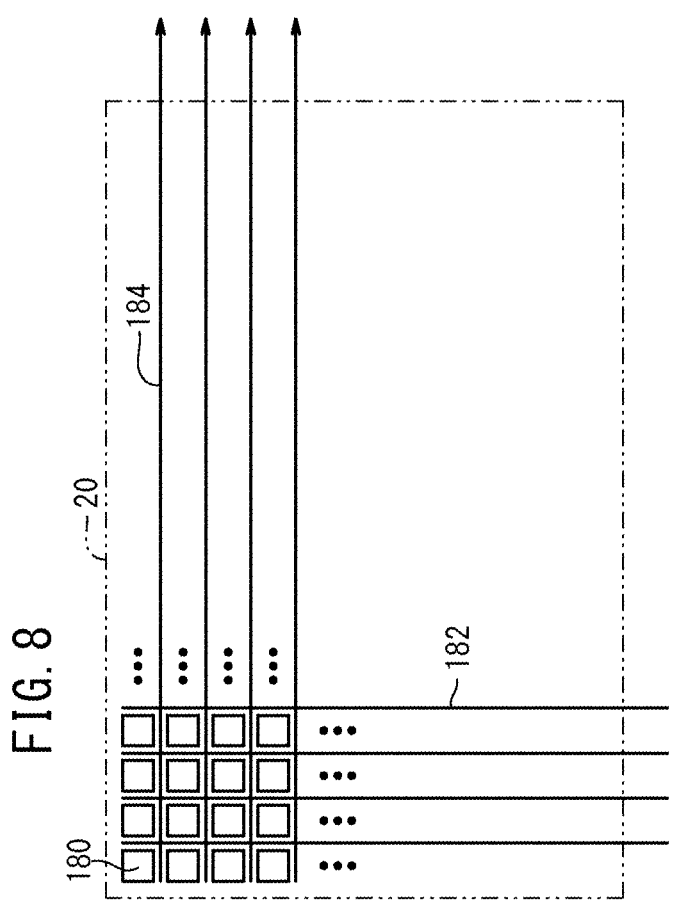
FIG. 8 is a view showing schematically a matrix made up of pixels in a radiation detector.

As schematically shown in FIG. 8, the radiation detector 20 comprises a number of pixels 180 arrayed on a substrate, not shown, a number of gate lines 182 for supplying control signals to the pixels 180, and a number of signal lines 184 for reading electric signals output from the pixels 180.

A circuit arrangement of the cassette device 22, which incorporates an indirect conversion type of radiation detector 20, for example, will be described in detail below with reference to FIG. 9.

Figure 9:
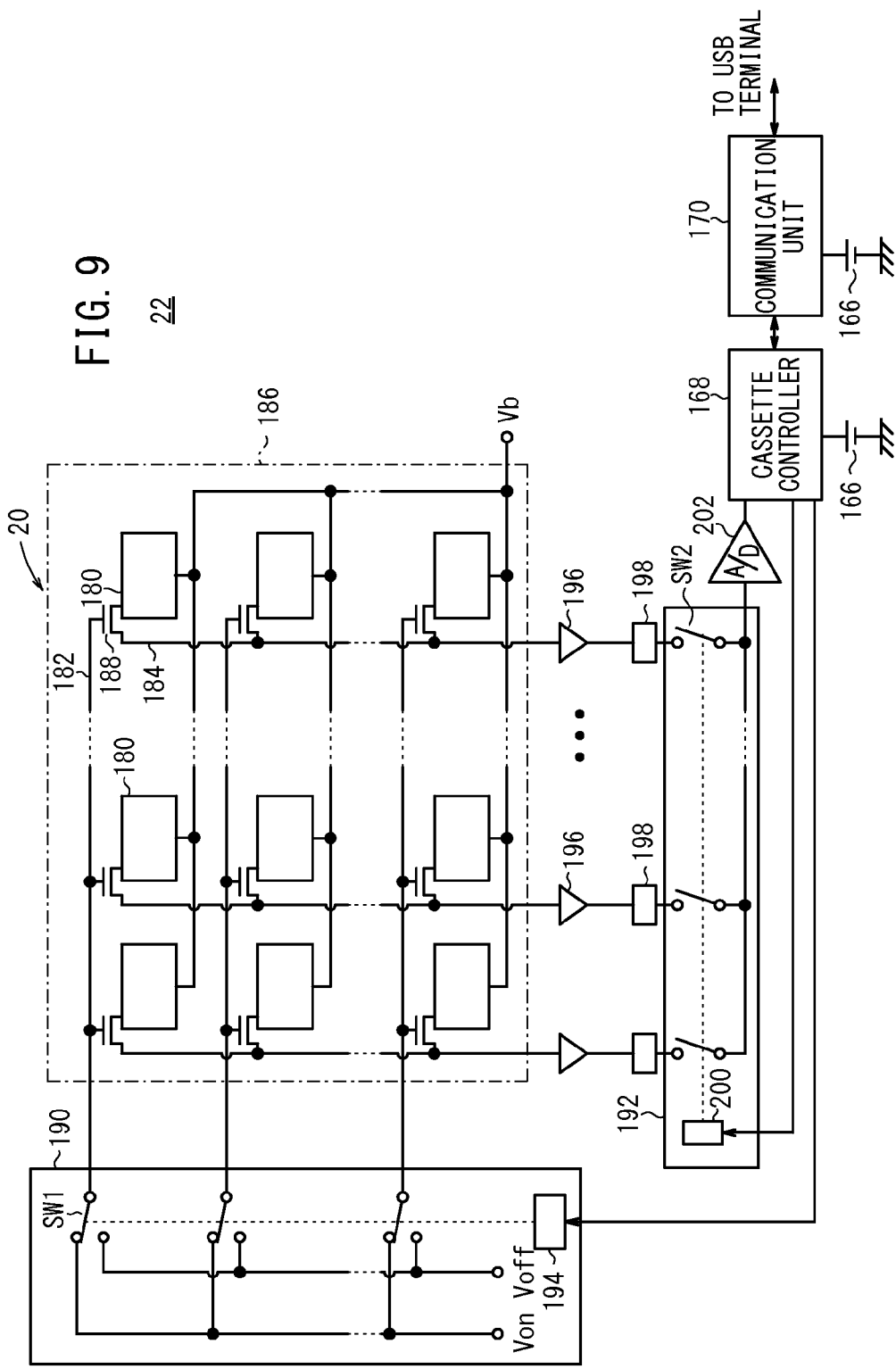
FIG. 9 is a circuit diagram of the cassette device.

As shown in FIG. 9, the radiation detector 20 comprises an array of TFTs 188 arranged in rows and columns, and a photoelectric conversion layer 186 including pixels 180 and made of a material such as amorphous silicon (a-Si) or the like for converting visible light into electric signals. The photoelectric conversion layer 186 is disposed on the array of TFTs 188. If radiation 12 is applied to the radiation detector 20, the pixels 180, which are supplied with a bias voltage Vb from the battery 166, generate electric charges by converting visible light into electric signals (analog signals). The TFTs 188 are turned on along each row at a time, whereupon the electric charges can be read out from the pixels 180 as an image signal.

The TFTs 188 are connected to the respective pixels 180. The gate lines 182, which extend parallel to the rows, and the signal lines 184, which extend parallel to the columns, are connected to the TFTs 188. The gate lines 182 are connected to a line scanning driver 190, and the signal lines 184 are connected to a multiplexer 192. The gate lines 182 are supplied with control signals Von, Voff from the line scanning driver 190 for turning on and off the TFTs 188 along the rows. The line scanning driver 190 comprises a plurality of switches SW1 for switching between the gate lines 182, and an address decoder 194 for outputting a selection signal for selecting one of the switches SW1 at a time. The address decoder 194 is supplied with an address signal from the cassette controller 168.

The signal lines 184 are supplied with electric charges that are stored by the pixels 180 through the TFTs 188 arranged in columns. Electric charges supplied to the signal lines 184 are amplified by amplifiers 196, which are connected respectively to the signal lines 184. The amplifiers 196 are connected to the multiplexer 192 through respective sample and hold circuits 198. The multiplexer 192 comprises a plurality of switches SW2 for successively switching between the signal lines 184, and an address decoder 200 for outputting selection signals for selecting one of the switches SW2 at a time. The address decoder 200 is supplied with address signals from the cassette controller 168. The multiplexer 192 has an output terminal connected to an A/D converter 202. A radiographic image signal, which is generated by the multiplexer 192 based on electric charges from the sample and hold circuits 198, is converted by the A/D converter 202 into a digital image signal representing radiographic image information, which is supplied to the cassette controller 168.

The TFTs 188, which function as switching devices, may be combined with another image capturing device such as a CMOS (Complementary Metal-Oxide Semiconductor) image sensor or the like. Alternatively, the TFTs 188 may be replaced with a CCD (Charge-Coupled Device) image sensor for shifting and transferring electric charges by way of shift pulses, which correspond to gate signals in the TFTs.

Figure 10:
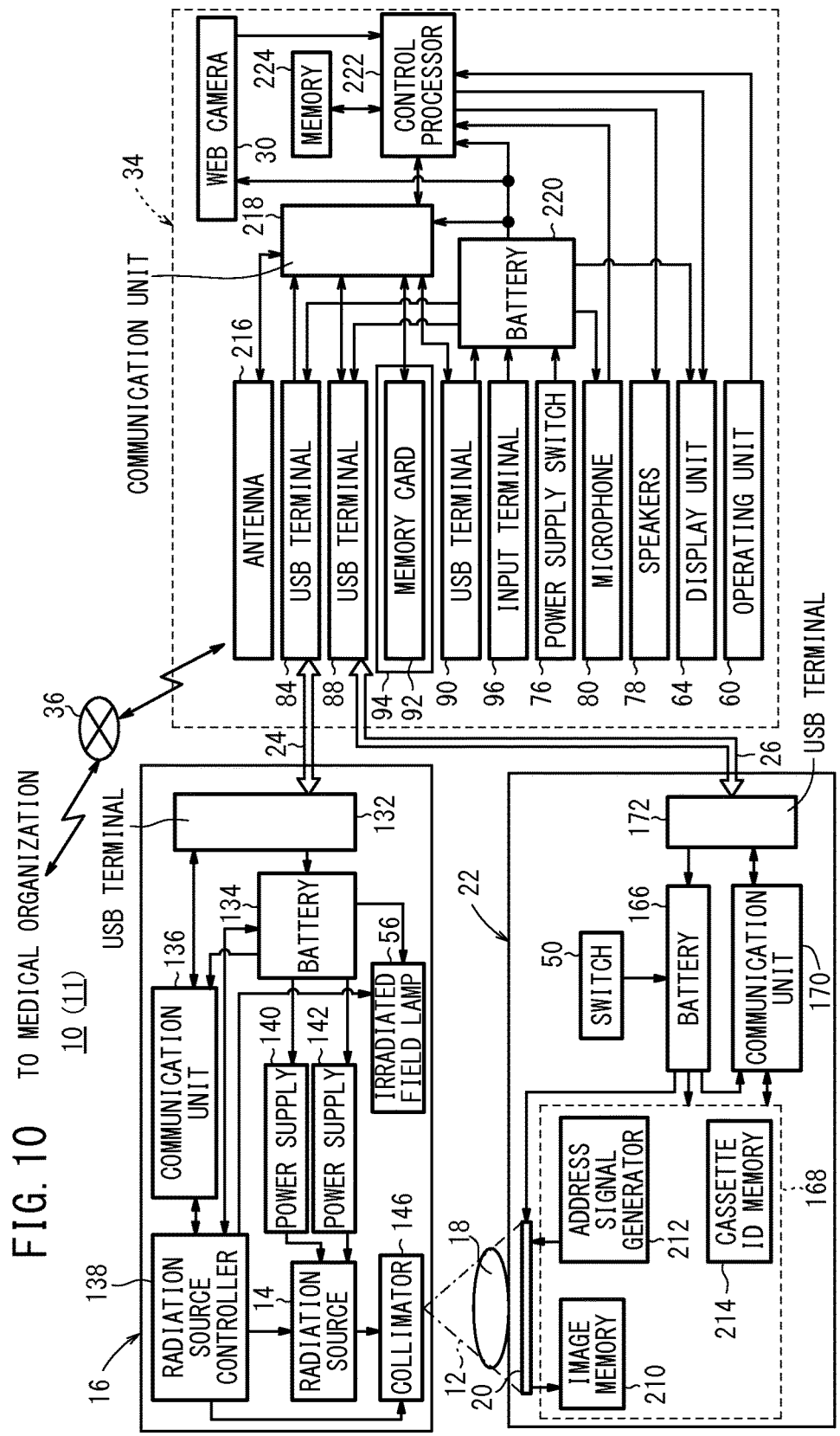
FIG. 10 is a block diagram of the radiographic image capturing apparatus shown in FIG. 1.
Figure 11:
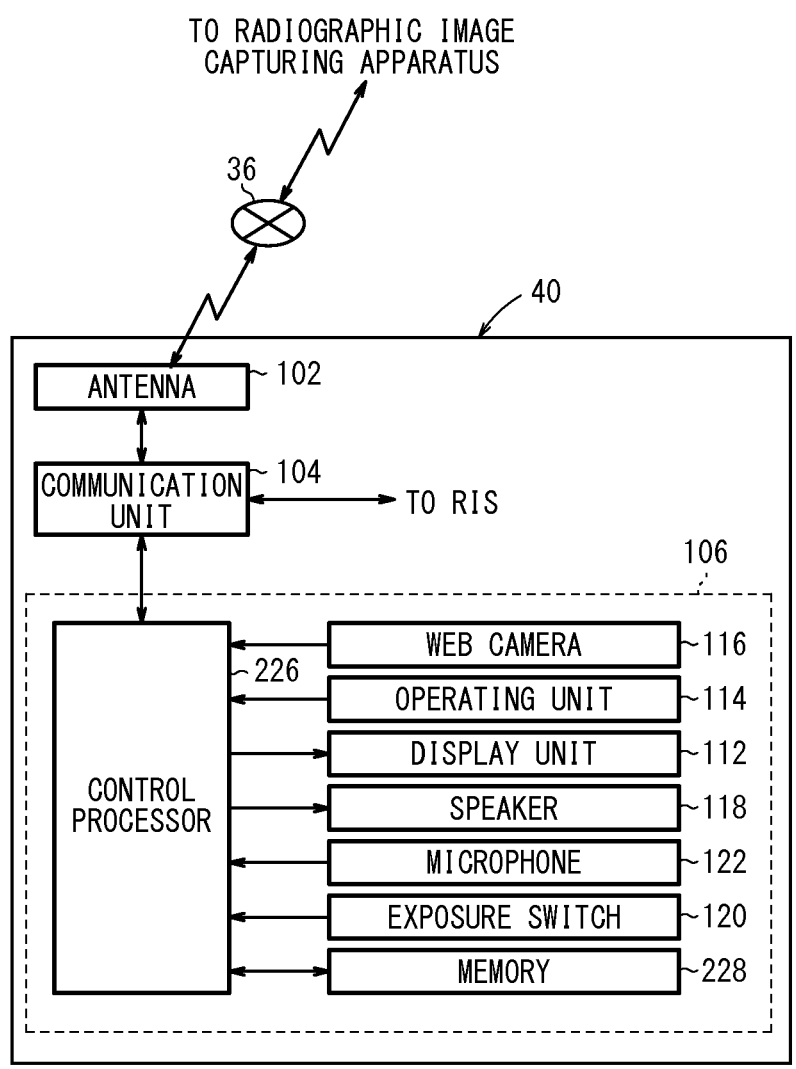
FIG. 11 is a block diagram of a medical organization shown in FIG. 1.

FIG. 10 shows in block form the radiographic image capturing apparatus 10, and FIG. 11 shows in block form the medical organization 40.

In FIGS. 10 and 11, constituent elements that have not been described above with reference to FIGS. 1 through 9 will be described in further detail, together with portions of the constituent elements that were described in FIGS. 1 through 9.

The cassette controller 168 of the cassette device 22 comprises an image memory 210, an address signal generator 212, and a cassette ID memory 214.

The address signal generator 212 supplies address signals to the address decoder 194 of the line scanning driver 190, and to the address decoder 200 of the multiplexer 192. The image memory 210 stores radiographic images detected by the radiation detector 20. The cassette ID memory 214 stores cassette ID information for identifying (the cassette device 22 of) the radiographic image capturing apparatus 10.

In this case, the cassette controller 168 sends the cassette ID information stored in the cassette ID memory 214, and the radiographic image information stored in the image memory 210 to the portable information terminal 34 from the communication unit 170 via the USB terminal 172 and the USB cable 26.

The portable information terminal 34 further includes a communication unit (controller communication unit, camera image communication unit) 218, a battery 220 for supplying electric power to various components of the portable information terminal 34, a control processor 222 for performing various control processes, and a memory 224 for storing camera images, radiographic images, etc.

The communication unit 218 sends signals to and receives signals from the exterior by way of wireless communications via an antenna 216, sends signals to and receives signals from the exterior by way of wired communications via the USB terminals 84, 88, 90, and sends signals to and receives signals from the memory card 92, which is inserted in the card slot 94.

If the operator 32 turns on the power supply switch 76, the battery 220 supplies electric power to the web camera 30, the speakers 78, the microphone 80, the communication unit 218, and the control processor 222. Further, while the portable information terminal 34 is electrically connected by the USB cables 24, 26 respectively to the radiation source device 16 and the cassette device 22, the battery 220 is capable of charging the batteries 134, 166 respectively via the USB cables 24, 26. Moreover, the battery 220 can also be charged from the exterior via the input terminal 96.

More specifically, in the foregoing manner, with the portable information terminal 34 electrically connected by the USB cable 24 to the radiation source device 16, electric power can be supplied and signals can be sent and received (transmitted) between the portable information terminal 34 and the radiation source device 16 by way of wired communications. Further, with the portable information terminal 34 electrically connected by the USB cable 26 to the cassette device 22, electric power can be supplied and signals can be sent and received (transmitted) between the portable information terminal 34 and the cassette device 22 by way of wired communications.

The control processor 222 comprises a CPU of the portable information terminal 34, which carries out various control sequences by reading and executing programs stored in the memory 224.

More specifically, the control processor 222 stores in the memory 224 camera images captured by the web camera 30 together with radiographic images and cassette ID information received from the cassette device 22 via the USB cable 26 and the communication unit 218, and together therewith, the control processor 222 controls the display unit 64 to display at least one of the camera images and the radiographic images. Further, the control processor 222 sends at least one of the camera images, and the radiographic images and the cassette ID information by way of wireless communications to the medical organization 40 via the communication unit 218, the antenna 216, and the network 36. In addition, the control processor 222 sends a voice signal representing the voice of the operator 32 or the voice of the subject 18 input to the microphone 80 by way of wireless communications to the medical organization 40 via the communication unit 218, the antenna 216, and the network 36.

Further, the control processor 222 controls the display unit 64 to display a camera image (of the doctor 38) captured by the web camera 116 and received from the medical organization 40 via the network 36, the antenna 216, and the communication unit 218, and outputs the voice of the doctor 38 from the speaker 78 based on the voice signal received from the medical organization 40. Furthermore, in the case that the control processor 222 receives an exposure control signal from the medical organization 40, the control processor 222 generates a synchronization control signal depending on the received exposure control signal, and sends the generated synchronization control signal to the radiation source device 16 and the cassette device 22 via the USB cable 24, 26. Accordingly, synchronization can be realized between output of radiation 12 from the radiation source 14 and detection and conversion of the radiation 12 into radiographic image information by the radiation detector 20.

The console 106 also includes a memory 228 and a control processor 226 for performing various control sequences.

The control processor 226 comprises a CPU of the main body 108, which carries out various control sequences by reading and executing programs stored in the memory 228.

More specifically, the control processor 226 stores the camera image captured by the web camera 116 in the memory 228, together with displaying the camera image on the display unit 112. Further, the control processor 226 sends the camera image captured by the web camera 116 to the portable information terminal 34 by way of wireless communications via the communication unit 104, the antenna 102, and the network 36. The control processor 226 also sends a voice signal representing the voice of the doctor 38 input to the microphone 122 to the portable information terminal 34 by way of wireless communications via the communication unit 104, the antenna 102, and the network 36.

Further, the control processor 226 stores in the memory 228 at least one of the camera image that was transmitted wirelessly from the portable information terminal 34, and the radiographic image and cassette ID information, together with displaying at least one of the camera image and the radiographic image on the display unit 112. Furthermore, the control processor 226 outputs from the speaker 118 the voice signal representing the voice of the operator 32 or the subject 18 that was transmitted wirelessly from the portable information terminal 34.

Further, prior to output of radiation 12 from the radiation source 14 (in the image capturing preparatory stage), if a region to be imaged of the subject 18 is visible within the outer frame of the guide lines 46 on a camera image captured by the web camera 30 and displayed on the display unit 112 (see FIGS. 14A and 14B), then the doctor 38 judges that an appropriate radiographic image of the region to be imaged of the subject 18 can be acquired if radiation were applied to the subject in this state, whereupon the doctor 38 turns on the exposure switch 120. Based on turning on of the exposure switch 120, the control processor 226 generates an exposure control signal for initiating output of radiation 12 from the radiation source 14, and the generated exposure control signal is transmitted to the portable information terminal 34 by way of wireless communications via the communication unit 104, the antenna 102, and the network 36.

On the other hand, prior to output of radiation 12 from the radiation source 14, if the region to be imaged of the subject 18 is not visible, or if only a portion of the region is included within the outer frame of the guide lines 46 on a camera image captured by the web camera 30 and displayed on the display unit 112 (see FIG. 14C), then the doctor 38 judges that an appropriate radiographic image of the region to be imaged of the subject 18 cannot be acquired by applying radiation 12 to the subject 18 in this condition. In this case, next, the doctor 38, without turning on the exposure switch 120, issues an instruction by voice over the microphone 122 to change the position or posture of the subject 18 so that the region to be imaged is included within the outer frame of the guide lines 46. Accordingly, in the case that such a voice signal (instruction signal) is input corresponding to the voice from the microphone 122, the control processor 226 does not generate an exposure control signal.

Operations of the Present Exemplary Embodiment

The radiographic image capturing apparatus 10 and the radiographic image capturing system 11 according to the present exemplary embodiment basically are constructed as described above. Next, operations (a radiographic image capturing method) thereof will be described below with reference to the flowcharts shown in FIGS. 12 and 13. In explaining such operations, FIGS. 1 through 11 may also be referred to as needed.

Figure 12:
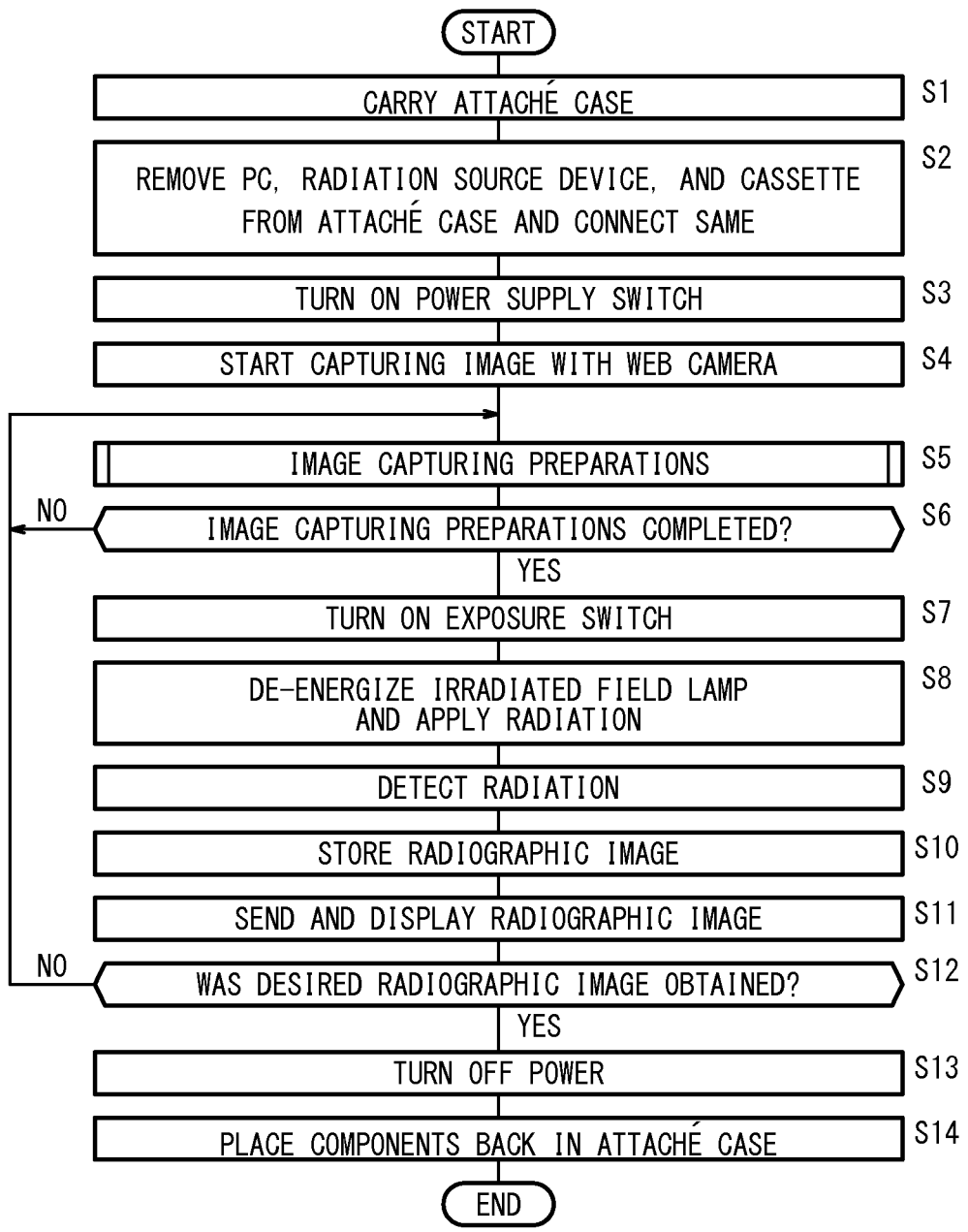
FIG. 12 is a flowchart for describing image capturing by the radiographic image capturing apparatus and the radiographic image capturing system shown in FIG. 1.

In step S1 shown in FIG. 12, the operator 32 (see FIG. 5) carries an attaché case 98 from the medical organization 40, where the doctor 38 is unable to observe the subject 18 directly, to a disaster site or a home care treatment site, according to directions from the doctor 38 who has legal authority to apply radiation 12 to the subject 18 (see FIGS. 1 through 4 and FIG. 10).

In step S2, after the operator 32 has arrived at the disaster site or the home care treatment site, at first, the operator 32 removes the radiation source device 16, the cassette device 22, the portable information terminal 34, and the USB cables 24, 26 from the attaché case 98. Then, the operator 32 connects the portable information terminal 34 and the radiation source device 16 using the USB cable 24, and connects the portable information terminal 34 and the cassette device 22 using the USB cable 26. As a result, the portable information terminal 34 and the radiation source device 16 are connected electrically via the USB cable 24, whereas the portable information terminal 34 and the cassette device 22 are connected electrically via the USB cable 26. Further, in step S2, the operator lays out the portable information terminal 34, the radiation source device 16 and the cassette device 22 according to the positional relationship shown in FIGS. 1 through 4.

In the following step S3, the operator 32 turns the lid 66 away from the main body 62 about the shaft 68 and the hinges 70, so as to unfold the portable information terminal 34 from the folded condition shown in FIGS. 5 and 16, and until the operating unit 60 and the display unit 64 are made visible, as shown in FIGS. 1 through 4. Thereafter, the operator 32 turns on the power supply switch 76 in order to activate the portable information terminal 34.

In this manner, by turning on the power supply switch 76, the battery 220 begins supplying electric power to the web camera 30, the display unit 64, the microphone 80, the communication unit 218, and the control processor 222. Further, the battery 220 begins to charge the battery 134 of the radiation source device 16 and the battery 166 of the cassette device 22 from the USB terminals 84, 88 through the USB cables 24, 26. As a result, the web camera 30 is activated by supply of power from the battery 220 and starts to capture an image of the image capturing region 28. The captured camera image is output to the control processor 222 (step S4).

On the other hand, by supply of power from the battery 220, the control processor 222 reads and executes the program from the memory 224. Owing thereto, the control processor 222 stores the camera image input from the web camera 30 in the memory 224, and displays the camera image on the display unit 64. Further, the control processor 222 transmits the camera image from the communication unit 218 to the exterior by way of wireless communications via the antenna 216.

The camera image from the web camera 30 is sent to the medical organization 40 by way of wireless communications over the network 36. The communication unit 104 of the medical organization 40 outputs to the control processor 226 the camera image received via the antenna 102. The control processor 226 reads and executes the program stored in the memory 228, whereby the camera image input from the web camera 30 is stored in the memory 228, together with displaying the camera image on the display unit 112. Upon viewing the content displayed on the display unit 112, the doctor 38 can reliably grasp the positional relationship between the radiation source device 16, the subject 18, and the cassette device 22 at the disaster site or the home care treatment site.

Next, in step S5, the operator 32 performs image capturing preparations for capturing a radiographic image of a region to be imaged (for example, a chest region) of the subject 18.

Figure 13:
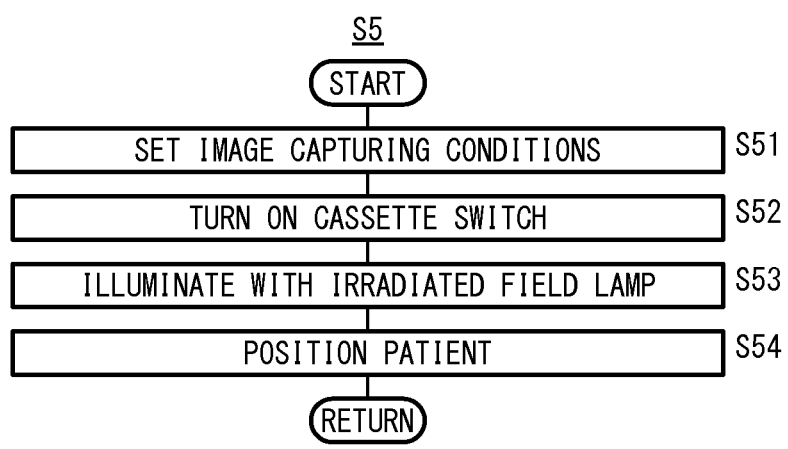
FIG. 13 is a flowchart for describing in greater detail image capturing preparations carried out in step S5 of the flowchart of FIG. 12.
Figure 14A:
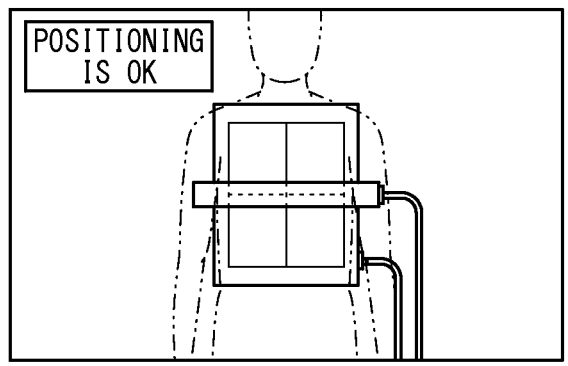
FIGS. 14A to 14C are exemplary views of display screens of at least one of a console and a portable information terminal.
Figure 14B:
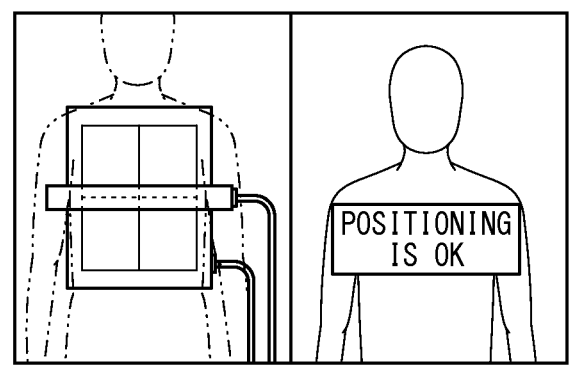
Figure 14C:
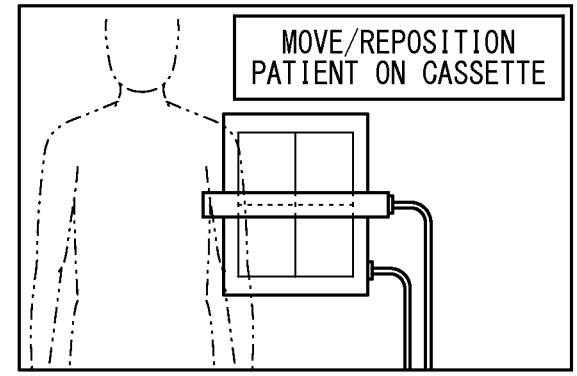

FIG. 13 is a flowchart for describing in greater detail image capturing preparations carried out in step S5. FIGS. 14A to 14C are exemplary views of display content, which is displayed on the display unit 64 of the portable information terminal 34 or the display unit 112 of the console 106 during image capturing preparations.

In step S51 of FIG. 13, the operator 32 operates the operating unit 60 (see FIGS. 1 and 10) of the portable information terminal 34, whereby subject information such as image capturing conditions (e.g., a tube voltage and tube current of the radiation source 14, an exposure time of the radiation 12) or the like pertaining to the subject 18 to be imaged are registered. In this case, if the region to be imaged and the imaging method are known beforehand, the operator 32 may also register such image capturing conditions in advance. The control processor 222 stores (registers) the input image capturing conditions in the memory 224.

In the event that the subject 18 to be imaged is known ahead of time before leaving for the disaster site or the home care treatment site, the operator 32 can enter and register the image capturing conditions by operating the operating unit 60 of the portable information terminal 34 at the medical organization 40 to which the operator 32 belongs.

Further, as described previously, because transmission and reception of signals wirelessly over the network 36 can be performed between the portable information terminal 34 and the medical organization 40, for example, the doctor 38 may input the aforementioned image capturing conditions by operating the operating unit 114 of the console 106, and the input image capturing conditions may be sent wirelessly to the portable information terminal 34 over the network 36. Alternatively, suitable image capturing conditions to be recorded in the memory 224 may be indicated from the medical organization 40 (the doctor 38) by way of wireless communications over the network 36. Further, by the operator 32 operating the operating unit 60, the image capturing conditions, which were indicated by way of wireless communications, can be registered.

If the operator 32 turns on the switch 50 of the cassette device 22 in the following step S52, the battery 166 supplies electric power to the radiation detector 20, the cassette controller 168, and the communication unit 170, thereby activating the cassette device 22 in its entirety. Consequently, the cassette controller 168 sends an activation notice signal, which indicates that the cassette device 22 has been activated, to the portable information terminal 34 by way of the communication unit 170, the USB terminal 172, and the USB cable 26.

Based on the activation notice signal received via the USB cable 26, the USB terminal 88, and the communication unit 218, the control processor 222 sends an image capturing preparation command signal for image capturing preparations, and the image capturing conditions registered in the memory 224 to the radiation source device 16 and the cassette device 22 by way of the communication unit 218, the USB terminals 84, 88, and the USB cables 24, 26.

The battery 134 of the radiation source device 16 continuously supplies electric power to the communication unit 136 and the radiation source controller 138. Therefore, if the radiation source controller 138 receives the image capturing preparation command signal and the image capturing conditions by way of the USB cable 24, the USB terminal 132 and the communication unit 136, the radiation source controller 138 registers the image capturing conditions, and then controls the battery 134 to supply electric power to the irradiated field lamp 56. Upon supplying the irradiated field lamp 56 with the electric power from the battery 134, the irradiated field lamp 56 emits irradiation light 54 (see FIGS. 3, 4, and 6). The irradiation light 54 is reflected by the mirror 144 toward the collimator 146, and is applied to the irradiated surface 44 of the cassette device 22 (step S53).

If the imaging distance is adjusted to the SID, then the irradiated field of radiation 12 that is displayed on the irradiated surface 44 by application of the irradiation light 54 is substantially in agreement with the outer frame of the guide lines 46. On the other hand, if the position of the irradiated field (i.e., the range irradiated by the irradiation light 54) is not in agreement with the position of the outer frame of the guide lines 46, or if the size of the irradiated field is not in agreement with the size of the outer frame of the guide lines 46, then the operator 32 adjusts the positional relationship between the radiation source device 16 and the cassette device 22 in order to bring the imaging distance and the SID into agreement with each other.

The image capturing preparation command signal and the image capturing conditions also are sent to the cassette device 22, so as to enable the cassette controller 168 to recognize that the radiographic image capturing apparatus 10 has been in an image capturing preparation stage, and also to register image capturing conditions in the cassette ID memory 214. Further, it has been described above that the radiation detector 20 is activated by turning on the switch 50. However, the battery 166 may also supply electric power (bias voltage Vb) to the radiation detector 20 in order to activate the radiation detector 20 upon receipt of the image capturing preparation command signal by the cassette controller 168.

In the foregoing manner, the image capturing distance is adjusted to the SID, and in step S54, after the irradiation field of the radiation 12 and the outer frame of the guide lines 46 have been brought into agreement with each other, the operator 32 arranges the subject 18 on the side of the irradiated surface 44 of the cassette device 22, and carries out positioning the subject 18 so that the region to be imaged of the subject 18 is positioned inside the outer frame of the guide lines 46.

In this case, the web camera 30 captures an image of the image capturing region 28 (see FIGS. 1 through 4) including the region to be imaged of the subject 18, the radiation source device 16, and the irradiated surface 44 of the cassette device 22, and the display unit 64 of the portable information terminal 34 displays the camera image captured by the web camera 30. Accordingly, while the operator 32 observes (monitors) the camera image displayed on the display unit 64, by giving instructions to the subject 18, the subject 18 can be positioned so that in the camera image the region to be imaged lies within the outer frame of the guide lines 46.

Further, the camera image captured by the web camera 30 is transmitted (delivered) to the medical organization 40 from the control processor 222 via the communication unit 218, the antenna 216, and the network 36. The communication unit 104 of the medical organization 40 outputs the camera image received over the antenna 102 to the console 106. The control processor 226 of the console 106 stores the camera image in the memory 228 and displays the camera image on the display unit 112.

In addition, in step S6 of FIG. 12, the doctor 38 of the medical organization 40 (see FIGS. 1 and 11) visually confirms the camera images from the web camera 30 (see FIGS. 1 through 4 and 10) displayed on the display unit 112, and judges whether or not the image capturing preparations for the subject 18 have been completed, and more specifically, whether or not the region to be imaged of the subject 18 is visible within the outer frame of the guide lines 46 in the camera image.

For example, as shown in FIG. 14A, in the case that the camera image displayed on the display units 64, 112 is an image in which the region to be imaged (the chest) is visible within the outer frame of the guide lines 46, the doctor 38 judges that an appropriate radiographic image of the subject 18 would be obtained if an image were captured having the positional relationship between the guide lines 46 and the region to be imaged presently displayed on the screens of the display units 64, 112 (step S6: YES). Thereafter, the doctor 38, by way of voice using the microphone 122, or by operating the operating unit 114, conveys to the operator 32 at the site that image capturing preparations are completed.

In this manner, the control processor 226 of the console 106 sends the voice signal input to the microphone 122 or a signal generated by the operating unit 114 to the portable information terminal 34 by way of wireless communications via the communication unit 104, the antenna 102, and the network 36. Based on the signal received via the antenna 216 and the communication unit 218, the control processor 222 of the portable information terminal 34 displays the characters "POSITIONING IS OK" on the display unit 64, thereby indicating that image capturing preparations have been completed, as shown in FIG. 14A. Alternatively, the control processor 222 may inform the operator 32 of completion of image capturing preparations by outputting speech sounds from the speakers 78. Therefore, the operator 32 can grasp that image capturing preparations have been completed by confirming the display content of the display unit 64, or by hearing the speech sounds from the speakers 78.

Further, the web camera 116 of the console 106 captures an image of the doctor 38, and the control processor 226 also sends the camera image from the web camera 116 to the portable information terminal 34 over the communication unit 104, the antenna 102 and the network 36. Owing thereto, as shown in FIG. 14B, the control processor 222 may display both alongside each other on the screen of the display unit 64 the camera image of the web camera 30 (the image showing positioning of the subject 18) and the camera image of the web camera 116 (the image of the doctor 38). At this time, the control processor 222 may also display on the screen of the display unit 64 the characters "POSITIONING IS OK" together with the camera image from the web camera 116.

In this manner, by displaying the image of the doctor 38 on the screen of the display unit 64, and by visually confirming the display content of the display unit 64, the operator 32 can comprehend immediately that the doctor 38 has confirmed the camera image of the web camera 30 and has approved capturing of an image with the present positioning of the subject 18 (i.e., has provided an indication that image capturing preparations are completed.)

Further, along with displaying the images of FIGS. 14A and 14B, the doctor 38 may cause a voice instruction input to the microphone 122 to be output from the speaker 78. Furthermore, similar to the display unit 64, display of images (refer to FIG. 14A or FIG. 14B) may also be performed on the display unit 112.

On the other hand, in step S6, if the camera image of the web camera 30 displayed on the display unit 112 indicates that the region to be imaged of the subject 18 is not included within the outer frame of the guide lines 46 (see FIG. 14C), or that only a portion of the region to be imaged is included therein, then the doctor 38 determines that a desired radiographic image of the subject 18 cannot be produced by capturing a radiographic image in the positional relationship between the guide lines 46 and the region to be imaged that is currently displayed on the screens of the display units 64, 112 (step S6: NO). Then, using the microphone 122 to enter a voice signal or by operating the operating unit 114, the doctor 38 conveys to the operator 32 at the site that the positional relationship between the region to be imaged and the guide lines 46 is inappropriate, and therefore that image capturing preparations must be performed again.

In this manner, the control processor 226 of the console 106 sends the voice signal input to the microphone 122 or a signal (instruction signal) generated by operating the operating unit 114 to the portable information terminal 34 by way of wireless communications via the communication unit 104, the antenna 102, and the network 36. Based on the signal received via the antenna 216 and the communication unit 218, the control processor 222 of the portable information terminal 34 displays the characters "MOVE/REPOSITION PATIENT ON CASSETTE" on the display unit 64, as shown in FIG. 14C, indicating that image capturing preparations must be performed again. Alternatively, speech sounds may be output from the speakers 78. Therefore, the operator 32 can grasp immediately that image capturing preparations must be repeated and the subject 18 must be positioned again, by confirming the content displayed on the display unit 64, or by hearing the speech sounds from the speakers 78.

In the case that the image capturing preparations of step S5 are to be repeated, since the processes of steps S51 to S53 (see FIG. 13) have already been performed, the operator 32 merely repeats and performs positioning of the subject 18 again.

In addition, in step S7, based on the assumption that image capturing preparations have been completed (step S6: YES), the doctor 38 turns on the exposure switch 120. As a result, the control processor 226 generates an exposure control signal to start emission of radiation 12 from the radiation source 14, and sends the exposure control signal to the portable information terminal 34 via the communication unit 104, the antenna 102, and the network 36.

If the control processor 222 receives the exposure control signal via the antenna 216 and the communication unit 218, the control processor 222 generates a synchronization control signal for capturing a radiographic image of the subject 18 by synchronizing start of emission of radiation 12 from the radiation source 14 with detection and conversion of radiation 12 into a radiographic image in the radiation detector 20. The generated synchronization control signal is sent to the radiation source device 16 and the cassette device 22 via the communication unit 218, the USB terminals 84, 88, and the USB cables 24, 26.

In step S8, upon the radiation source controller 138 (see FIGS. 6 and 10) receiving the synchronization control signal through the USB terminal 132 and the communication unit 136, the radiation source controller 138 stops supplying electric power from the battery 134 to the irradiated field lamp 56, thereby de-energizing the irradiated field lamp 56 and stopping emission of irradiation light 54, and together therewith, the radiation source controller 138 controls the radiation source 14 to apply radiation 12 at a predetermined dose to the subject 18 according to the image capturing conditions registered in the radiation source controller 138.

In this manner, in the radiation source 14, the rotating mechanism 148 is controlled by the radiation source controller 138 to rotate the rotational shaft 150 and the rotary anode 152. The power supply 142 applies a negative voltage to the field-emission-type electron source 158 based on electric power supplied from the battery 134, and the power supply 140 applies a voltage between the rotary anode 152 and the cathode 156 based on electric power supplied from the battery 134. The field-emission-type electron source 158 emits electrons, which are accelerated by the voltage applied between the rotary anode 152 and the cathode 156 and bombard the target layer 154. The surface of the target layer 154 that is bombarded with electrons (the focus point 160) emits radiation 12, the intensity of which depends on the applied electrons.

Radiation 12 passes through the mirror 144 and the irradiation area thereof is constricted by the collimator 146, after which radiation 12 is output from the radiation source device 16 and applied to the subject 18. Radiation 12 is applied to and passes through the subject 18 for a given exposure time depending on the image capturing conditions, and reaches the radiation detector 20 in the cassette device 22.

In step S9, since the radiation detector 20 (see FIGS. 3, 4, and FIGS. 7 through 10) is of an indirect conversion type, the scintillator of the radiation detector 20 emits visible light having an intensity that depends on the intensity of the radiation 12. The pixels 180 of the photoelectric conversion layer 186 convert visible light into electric signals and store the electric signals as electric charges. The electric charges stored by the pixels 180, which are representative of a radiographic image of the subject 18, are read from the pixels 180 according to address signals, which are supplied from the address signal generator 212 of the cassette controller 168 to the line scanning driver 190 and the multiplexer 192.

More specifically, in response to the address signal supplied from the address signal generator 212, the address decoder 194 of the line scanning driver 190 outputs a selection signal to select one of the switches SW1, which supplies the control signal Von to the gates of the TFTs 188 connected to the gate line 182 corresponding to the selected switch SW1. In response to the address signal supplied from the address signal generator 212, the address decoder 200 of the multiplexer 192 outputs a selection signal to successively turn on the switches SW2, so as to switch between the signal lines 184 for thereby reading, through the signal lines 184, the electric charges stored in the pixels 180 connected to the selected gate line 182.

The radiographic image read from the pixels 180 connected to the selected gate line 182 is amplified by the respective amplifiers 196, sampled by the sample and hold circuits 198, and supplied via the multiplexer 192 to the A/D converter 202 and converted into digital signals. The converted digital signals, which are representative of the radiographic image, are stored in the image memory 210 of the cassette controller 168 (step S10).

Similarly, the address decoder 194 of the line scanning driver 190 successively turns on the switches SW1 in order to switch between the gate lines 182 according to address signals supplied from the address signal generator 212. The electric charges stored in the pixels 180 connected to the successively selected gate lines 182 are read through the signal lines 184, and are processed into digital signals by the multiplexer 192 and the A/D converter 202, whereupon the digital signals are stored in the image memory 210 of the cassette controller 168 (step S10).

The radiographic image stored in the image memory 210 is transmitted together with the cassette ID information stored in the cassette ID memory 214 to the portable information terminal 34 by way of wired communications via the communication unit 170, the USB terminal 172, and the USB cable 26. The control processor 222 of the portable information terminal 34 stores the radiographic image and the cassette ID information received via the USB terminal 88 and the communication unit 218 in the memory 224, and displays the radiographic image on the display unit 64 (refer to step S11 and FIG. 15A).

Further, the control processor 222 transmits the radiographic image and the cassette ID information to the medical organization 40 wirelessly via the communication unit 218, the antenna 216, and the network 36. Consequently, in the medical organization 40, the communication unit 104 outputs the radiographic image and the cassette ID information received via the antenna 102 to the control processor 226, whereupon the control processor 226 stores the radiographic image and the cassette ID information in the memory 228 together with displaying the radiographic image on the display unit 112 (see FIG. 15A).

In step S12, the doctor 38 visually confirms the radiographic image displayed on the display unit 112 and judges whether or not an appropriate radiographic image of the subject 18 has been obtained.

Figure 15A:
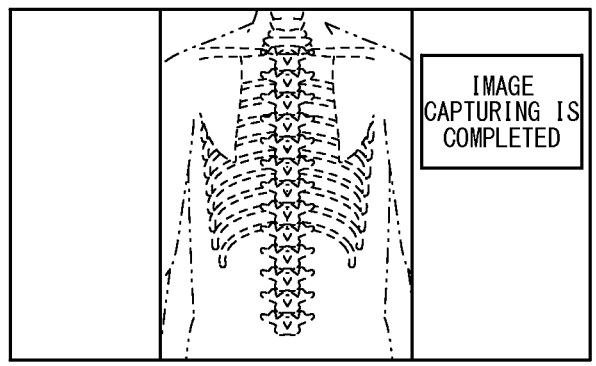
FIGS. 15A to 15C are exemplary views of display screens of at least one of a console and a portable information terminal.

For example, if as shown in FIG. 15A, the radiographic image displayed on the display units 64, 112 is an image that includes the region to be imaged (the chest region) of the subject 18, the doctor 38 determines that image capturing of the radiographic image with respect to the region to be imaged has been completed properly (step S12: YES). Next, the doctor 38, by way of a voice message using the microphone 122, or by operating the operating unit 114, conveys to the operator 32 at the site that image capturing has been completed.

As a result, the control processor 226 of the console 106 sends the voice message input to the microphone 122, or a signal responsive to operations performed using the operating unit 114, to the portable information terminal 34 by way of wireless communications via the communication unit 104, the antenna 102, and the network 36. Based on the signal received via the antenna 216 and the communication unit 218, the control processor 222 of the portable information terminal 34 displays on the display unit 64 the characters "IMAGE CAPTURING IS COMPLETED" as shown in FIG. 15A, or alternatively outputs a voice message from the speaker 78, to indicate completion of image capturing. Accordingly, by visually confirming the content displayed on the display unit 64, or by listening to the voice message from the speaker 78, the operator 32 can grasp that image capturing has been completed.

Figure 15B:
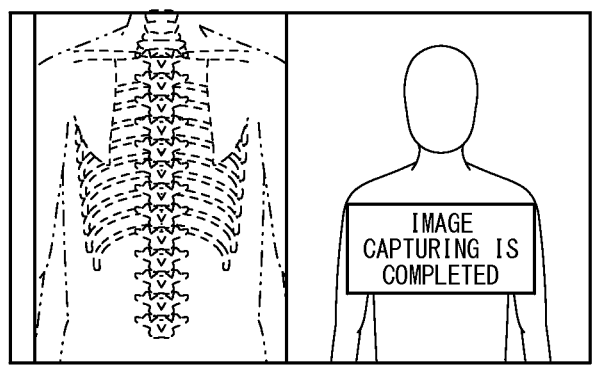

Further, similar to the case of FIG. 14B, as shown in FIG. 15B, the control processor 222 may display alongside each other the radiographic image and the camera image (of the doctor) from the web camera 116 on the screen of the display unit 64, along with displaying the characters "IMAGE CAPTURING IS COMPLETED" in the camera image from the web camera 116.

By displaying in tandem the image of the doctor 38 on the screen of the display unit 64, the operator 32 can understand immediately that the doctor 38 has indicated completion of image capturing.

Further, together with the image displays of FIG. 15A and FIG. 15B, a voice message of the doctor 38 input to the microphone 122 can be output from the speaker 78, or a display image similar to that of the display unit 64 (see FIG. 15A or 15B) can be performed on the display unit 112.

On the other hand, in step S12, in the case that the region to be imaged is not visible within the radiographic image displayed on the display unit 112, or if only a portion of the region to be imaged is included therein (see FIG. 15C), the doctor 38 judges that an appropriate radiographic image could not be obtained and that image recapturing is necessary (step S12: NO). In this case, by a voice message using the microphone 122, or by operating the operating unit 114, the doctor 38 conveys to the operator 32 at the site that the image needs to be captured again.

Figure 15C:
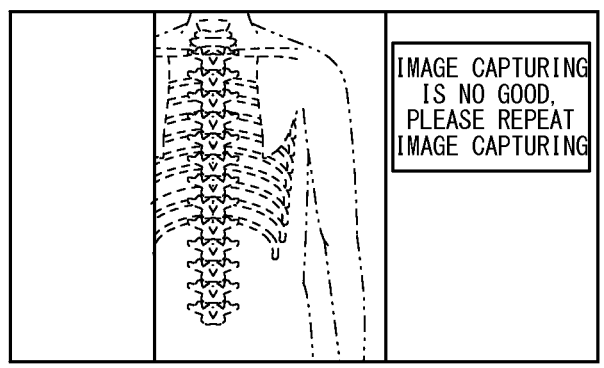

As a result, the control processor 226 of the console 106 transmits wirelessly to the portable information terminal 34, via the communication unit 104, the antenna 102, and the network 36, the voice message input to the microphone 122, or a signal indicative of the content entered using the operating unit 114. Based on the signal received via the antenna 216 and the communication unit 218, as shown in FIG. 15C, the control processor 222 of the portable information terminal 34 displays on the display unit 64 the characters "IMAGE CAPTURING IS NO GOOD, PLEASE REPEAT IMAGE CAPTURING", or outputs a corresponding voice message from the speaker 78 for indicating image-recapturing. Consequently, by visually confirming the content displayed on the display unit 64, or by listening to the voice message from the speaker 78, the operator 32 grasps that image capturing should be carried out again, and returning to step S5, performs the image capturing preparations again according to the instruction content.

In step S13, after completion of image capturing, the operator 32 operates the operating unit 60 or presses the power supply switch 76 in order to shut off the portable information terminal 34, whereupon the battery 220 stops supplying electric power from the battery 220 to various components in the portable information terminal 34, and charging of the batteries 134, 166 from the battery 220 via the USB cables 24, 26 also is halted. The radiation source controller 138 detects cessation of charging of the battery 134, and halts the supply of power from the battery 134 to various components in the radiation source device 16. Furthermore, by pressing the switch 50, the operator 32 turns off the cassette device 22. As a result, supply of power from the battery 166 to various components in the cassette device 22 is halted.

Next, the operator 32 turns the lid 66 toward the main body 62 about the hinges 70 and the shaft 68 of the portable information terminal 34, thereby bringing the teeth 72 into the recesses 74 and folding the portable information terminal 34.

Next, the operator 32 removes the USB cables 24, 26 from the radiation source device 16, the cassette device 22, and the portable information terminal 34. As a result, electrical connection between the portable information terminal 34 and the radiation source device 16, and electrical connection between the portable information terminal 34 and the cassette device 22 are disconnected.

Thereafter, the operator 32 places the radiation source device 16, the cassette device 22, the portable information terminal 34, and the USB cables 24, 26 in the attaché case 98 (step S14), and the operator 32 carries the attaché case 98 back to the medical organization 40 to which the operator 32 belongs.

At the medical organization 40, radiographic images stored in the memory 224 of the radiographic image capturing apparatus 10 carried back by the operator 32 are transmitted to the console 106 or the RIS of the hospital network by way of wireless communications via the communication unit 218 and the antenna 216, or by wired communications via the USB terminals 84, 88, 90. Alternatively, the radiographic images are stored in a memory card 92, after storage thereof the memory card 92 is removed from the card slot 94, and the radiographic images are read out from the memory card 92 and supplied to the RIS. Consequently, in the medical organization 40, detailed radiographic image diagnosis can be implemented on the radiographic images.

As described above, in a state in which the radiographic image capturing apparatus 10 is laid out at a disaster site or a home care treatment site, radiographic images, etc., are transmitted to the medical organization 40 from the portable information terminal 34 via the network 36. Therefore, at the medical organization 40, detailed image diagnosis can be carried out using radiographic images sent from the site.

Advantages of the Present Exemplary Embodiment

As described above, with the radiographic image capturing apparatus 10, the radiographic image capturing system 11, and the radiographic image capturing method according to the present exemplary embodiment, at a disaster site or a home care treatment site, the web camera 30, which is constructed integrally with the portable information terminal 34 (incorporated in the portable information terminal 34), captures an image at least of the cassette device 22 (the guide lines 46 corresponding to the radiation detector 20 accommodated therein), whereas the communication unit 218 transmits the camera image captured by the web camera 30 through the network 36 to the communication unit 104 provided at the medical organization 40.

Owing thereto, based on the camera image received by the communication unit 104, a doctor (or radiological technician) 38 who waits at the (remote) medical organization 40 while being unable to observe the subject 18 directly can provide instructions for capturing an image of the subject 18 in real time to the operator 32 of the radiographic image capturing apparatus 10 at a disaster site or a home care treatment site. Therefore, even if the doctor 38 cannot travel directly to the disaster site or the home care treatment site, i.e., even without accompanying the operator 32 who does not possess a license as a radiographic technician (i.e., who is not qualified to apply radiation 12 to the subject 18), capturing of images with respect to the subject 18 can still be carried out.

In this case, the outer frame of the guide lines 46 corresponds to the irradiated field of radiation 12 at the time that the image capturing distance was set to the SID, and the web camera 30 captures an image of the outer frame of the guide lines 46. Accordingly, the doctor 38 observes the camera image from the web camera 30, and assuming that the region to be imaged of the subject 18 lies within the outer frame of the guide lines 46 (i.e., is imaged inside of the guide lines 46), it can be judged that a suitable radiographic image will be captured by irradiating the subject 18 with radiation 12. On the other hand, in the event that the region to be irradiated of the subject 18 is distanced from or lies outside of the guide lines 46, or if only a portion of the region to be imaged lies within the guide lines 46, in this condition, the doctor 38 can judge that a desired radiographic image cannot be obtained if the subject 18 is irradiated with radiation 12.

In this manner, the web camera 30 captures an image of the guide lines 46, and while observing (monitoring) the camera image from the web camera 30, the doctor 38 judges whether or not the region to be imaged of the subject 18 is included within the guide lines 46, whereby it can be determined whether or not an appropriate radiographic image can be obtained. As a result, even if the doctor 38 cannot directly observe the subject 18 and the operator 32, appropriate instructions for image capturing preparations can be given to the operator 32 at the site.

Further, as noted previously, the web camera 30 is incorporated into an upper side surface of the lid 66 of the portable information terminal 34, and is constructed integrally with the portable information terminal 34. In this case, as shown in FIGS. 1 through 4, because the web camera 30 captures an image of the radiation source device 16, the subject 18, and the cassette device 22 including the guide lines 46, a camera image that includes the guide lines 46 therein can reliably be captured.

Further, while operating the portable information terminal 34, the operator 32 instructs the subject 18 to position the subject 18 with respect to the guide lines 46. Even if radiation 12 is applied from the radiation source 14 to the subject 18 while the operator 32 operates the portable information terminal 34, the operator 32 is reliably prevented from being exposed to radiation 12.

The communication unit 218 of the portable information terminal 34, which incorporates the web camera 30, sends a camera image to the medical organization 40 via the antenna 216 and the network 36. Consequently, the camera image can reliably be sent to the medical organization 40.

In this case, the control processor 222 of the portable information terminal 34 generates a synchronization control signal, which synchronizes with each other output of radiation 12 from the radiation source 14, and conversion of the radiation 12 into a radiographic image in the radiation detector 20. The communication unit 218 sends the synchronization control signal to the communication unit 136 of the radiation source device 16 and to the communication unit 170 of the cassette device 22. Therefore, the radiation source 14 and the radiation detector 20 can reliably be synchronized during times that radiographic images are being captured.

Further, because the portable information terminal 34, the radiation source device 16, and the cassette device 22 are connected electrically via the USB cables 24, 26, the battery 134 of the radiation source device 16 or the battery 166 of the cassette device 22 can reliably be charged from the battery 220 of the portable information terminal 34, together with reliably performing transmission and reception of signals therebetween. More specifically, transmission of image capturing conditions or synchronization control signals from the portable information terminal 34 to the radiation source device 16 and the cassette device 22, as well as transmission of radiographic images from the cassette device 22 to the portable information terminal 34 can reliably be carried out.

Furthermore, inasmuch as the camera image captured by the web camera 30 and the radiographic image are sent from the portable information terminal 34 to the medical organization 40 by way of wireless communications via the network 36, the doctor 38 at the medical organization 40 can give appropriate instructions to the operator 32 and the subject 18 at the site by visually recognizing the camera image and the radiographic image, which are displayed on the display unit 112 of the console 106.

Further, the console 106 includes the exposure switch 120 for initiating output of radiation 12 from the radiation source 14. In this case, if the doctor 38 turns on the exposure switch 120 based on the camera image displayed on the display unit 112, the control processor 226 of the console 106 generates an exposure control signal for initiating output of radiation 12 from the radiation source 14, and sends the generated exposure control signal from the communication unit 104 to the portable information terminal 34 via the network 36. Thus, the control processor 222 of the portable information terminal 34 generates a synchronization control signal based on the exposure control signal received by the communication unit 218, and sends the generated synchronization control signal to the radiation source device 16 and the cassette device 22.

Consequently, the doctor 38 can capture a radiographic image of the subject 18 in real time while monitoring the subject 18 at the medical organization 40 where the doctor 38 is unable to observe the subject 18 directly, without requiring the doctor 38 to travel to the disaster site or the home care treatment site.

More specifically, in a case where image capturing preparations have been completed, if the region to be imaged of the subject 18 is included within the outer frame of the guide lines 46 as shown in the camera image captured by the web camera 30, the doctor 38 turns on the exposure switch 120 to start capturing a radiographic image of the subject 18. On the other hand, if the region to be imaged of the subject 18 is not included within the outer frame of the guide lines 46 in the camera image, or if only a portion of the region to be imaged is included within the outer frame of the guide lines 46 in the camera image, the doctor 38 does not turn on the exposure switch 120, but instead instructs the operator 32 to carry out image capturing preparations once again.

Thus, an image capturing process can easily and reliably be performed under remote control from the medical organization 40.

The doctor 38 instructs the operator 32 at the site through screens, which are displayed on the display unit 64, and via speech sounds, which are output from the speakers 78. Accordingly, the doctor 38 can accurately and efficiently send instructions to the operator 32 at the site.

If the camera images output from the web camera 30 are moving images, or still images that are captured intermittently at given time intervals, the doctor 38 can provide timely instructions to the operator 32 at the site. Even if the camera images are still images captured at certain times during image capturing preparations, the doctor 38 can judge whether or not the subject 18 is in a state that enables radiographic images to be captured by observing the still images.

If the web camera 30 is an optical camera, then the web camera 30 can produce camera images that are easily and highly visible to the doctor 38.

It has been described above that the doctor 38 provides instructions to the operator 32 both through screens that are displayed on the display unit 64 and via speech sounds that are output from the speakers 78. However, the doctor 38 may provide instructions to the operator 32 only through the screens displayed on the display unit 64, or only via speech sounds output from the speakers 78.

It also has been described above that the doctor 38 gives instructions to the operator 32, and that the operator 32 positions the subject 18 according to the content of such instructions. Since speech sounds output from the speakers 78 are heard by the subject 18, the doctor 38 may send instructions directly to the subject 18 in order to position the subject 18. Alternatively, before the subject 18 is positioned, the subject 18 may confirm the content of such instructions, which are displayed on the display unit 64, and the subject 18 may position him or herself with respect to the guide lines according to the instructions.

It also has been described above that the portable information terminal 34 sends the synchronization control signal to the radiation source device 16 and the cassette device 22 via the USB cables 24, 26. However, instead, the control processor 226 of the console 106 may generate a synchronization control signal, and may send the generated synchronization control signal to the radiation source device 16 and the cassette device 22 via the network 36, the portable information terminal 34, and the USB cables 24, 26.

Still further, rather than activating the cassette device 22 by turning on the switch 50, the operator 32 may activate the cassette device 22 by operating the operating unit 60. Alternatively, the doctor 38 may activate the cassette device 22 by operating the operating unit 114.

A case has been described above in which the battery 220 charges the batteries 134, 166 in a state of electrical connection of the portable information terminal 34 to the radiation source device 16 and the cassette device 22 via the USB cables 24, 26. However, in place of this configuration, in a case where the batteries 134, 166 are charged, the batteries 134, 166 may be charged to a capacity that is large enough to capture at least as many radiographic images of the subject 18 as required. Accordingly, a required number of radiographic images of the subject 18 can reliably be captured.

Alternatively, the batteries 134, 166 may be charged only during a time period required for performing steps S3 through S7 of FIG. 12. Thus, since the batteries 134, 166 are not charged while radiographic images are being sent during and after radiographic images are being captured, while image capturing is carried out, noise caused by battery charging is prevented from being added to the electric charge signals (analog signals), or while the radiographic images are being sent, such noise can be prevented from being added to the radiographic images.

It has been described above that a radiographic image begins to be captured if the exposure switch 120 is turned on. However, since a radiographic image may start to be captured by an instruction from the doctor 38, an exposure button (exposure switch) may be displayed on the screen of the display unit 112, which is a touch panel display unit, for example, and the doctor 38 may press the displayed exposure button to start capturing a radiographic image. Alternatively, one button on the operating unit 114 may be used as a dedicated exposure switch, whereby a radiographic image starts to be captured by pressing the button.

The cassette device 22 is in the shape of a box. However, a portion of the cassette device 22 where the radiation detector 20, etc., is positioned may be in the shape of a flexible sheet. Since the flexible sheet can be wound into a roll, the overall radiographic image capturing apparatus 10 including the cassette device 22 can be reduced in size and weight.

Further, during image capturing, the radiation source device 16 and the cassette device 22 are fixed in predetermined positions by non-illustrated fixing members, however, at least during image capturing, the operator 32 may hold the radiation source device 16 by hand.

Although a case has been described above in which the batteries 134, 166 are charged from the battery 220, any one of the three batteries may be regarded as a power supply for the overall radiographic image capturing apparatus 10, which is capable of charging the other two remaining batteries.

Still further, it has been described above that the camera image captured by the web camera 30 is sent from the communication unit 218 of the portable information terminal 34 to the communication unit 104 of the medical organization 40 via the network 36. However, the present exemplary embodiment is not limited to such a configuration.

For example, the communication unit 136 of the radiation source device 16 and the communication unit 170 of the cassette device 22 may include a function for communicating with the communication unit 104 via the network 36, whereby camera images can be sent from the communication units 136, 170.

By providing the communicating function so as to be incorporated in the communication units 136, 170, it is possible for the communication unit 170 to send radiographic images directly to the communication unit 104 via the network 36, and also to send radiographic images to the communication unit 104 via the communication unit 136 and the network 36.

Furthermore, all of the signals may be sent and received between the radiographic image capturing apparatus 10 and the medical organization 40 through the communication units 136, 104 or through the communication units 170, 104.

Moreover, as described above, signals are sent and received between the radiographic image capturing apparatus 10 and the medical organization 40 via the network 36 by way of wireless communications. However, the present exemplary embodiment is not limited to such a configuration. Signals may be sent and received by way of other forms of communication.

More specifically, signals may be sent and received between the radiographic image capturing apparatus 10 and the medical organization 40 by way of wired communications via the network 36.

Alternatively, signals may be sent and received by way of wired and wireless communications via the network 36. More specifically, if the network 36 includes a repeater (repeating device), then signals may be sent and received by way of wired communications (or wireless communications) up to the repeater, and then sent and received by way of wireless communications (or wired communications) beyond the repeater.

Further, another portable terminal such as a mobile telephone or the like may be electrically connected to the portable information terminal 34. Signals may be sent and received between the portable information terminal 34 and the medical organization 40, or may be sent and received between the radiation source device 16 and the cassette device 22, using a communication function of the other portable terminal. According to this modification, the communication unit of the other portable terminal functions as the communication unit 218.

The present exemplary embodiment is applicable to acquisition of radiographic images using a light readout type of radiation detector. Such a light readout type radiation detector operates in the following manner. If radiation is applied to a matrix of solid-state detecting devices, the solid-state detecting devices store an electrostatic latent image depending on the dose of radiation applied thereto. For reading the stored electrostatic latent image, reading light is applied to the solid-state detecting devices to cause the solid-state detecting devices to generate an electric current representing a radiographic image. If erasing light is applied to the radiation detector, a radiographic image represented by the residual electrostatic latent image is erased from the radiation detector, which can be reused (see Japanese Laid-Open Patent Publication No. 2000-105297).

Still further, in order to prevent the radiographic image capturing apparatus 10 from being contaminated with blood and bacteria, the entire radiographic image capturing apparatus 10 may be of a water-resistant and hermetically sealed structure, and the radiographic image capturing apparatus 10 can be sterilized and cleaned as necessary so that it can be used repeatedly.

In the present exemplary embodiment, as shown in FIG. 16, a cradle 230 for charging the batteries 134, 166, 220 (see FIG. 10) is positioned at a desired location in the medical organization 40.

In this case, the cradle 230 is electrically connected to the portable information terminal 34 by a USB cable 234 having connectors 236, 238. Further, the cradle 230 is electrically connected to the radiation source device 16 by a USB cable 24. Moreover, the cradle 230 is electrically connected to the cassette device 22 by a USB cable 26.

The cradle 230 may be capable not only of charging the batteries 134, 166, 220, but may also have a wireless or wired communication function to send and receive necessary information to and from the console 106 and the RIS of the medical organization 40. Information that is sent from the cradle 230 may include radiographic images, which are recorded in the radiographic image capturing apparatus 10 that is connected to the cradle 230.

The cradle 230 has a display unit 232 for displaying a charged state of the radiographic image capturing apparatus 10 connected to the cradle 230, together with other necessary information including radiographic images acquired from the radiographic image capturing apparatus 10.

A plurality of cradles 230 may be connected to a network, and charged states of radiographic image capturing apparatus 10, which are connected to the cradles 230, may be retrieved through the network, so that the user can confirm the locations of radiographic image capturing apparatus 10 that are charged sufficiently based on the retrieved charged stages.

The radiographic image capturing apparatus 10 according to the present exemplary embodiment has been illustrated as being used to capture radiographic images at disaster sites and home care treatment sites. However, the radiographic image capturing apparatus 10 according to the present exemplary embodiment is not limited to capturing radiographic images at disaster sites and home care treatment sites. Alternatively, the radiographic image capturing apparatus 10 may be mounted on medical checkup cars for capturing radiographic images for use in medical checkups, or may be used to capture radiographic images of patients during a doctor's rounds in the medical organization 40. Furthermore, the radiographic image capturing apparatus 10 according to the present exemplary embodiment is not limited to being used for capturing radiographic images in the medical field, but may be applied to capturing radiographic images in various nondestructive tests, for example.

Modifications of the Present Exemplary Embodiment

Modifications (ranging from first through fourteenth modifications) of the above exemplary embodiment will be described below with reference to FIGS. 17 through 41B.

Structural components of the modifications, which are identical to those shown in FIGS. 1 through 16, are denoted by identical reference characters, and such features will not be described in detail below. Further, in FIGS. 17 through 41B, the network 36 and the medical organization 40 are omitted from illustration.

First Modification

Figure 17:
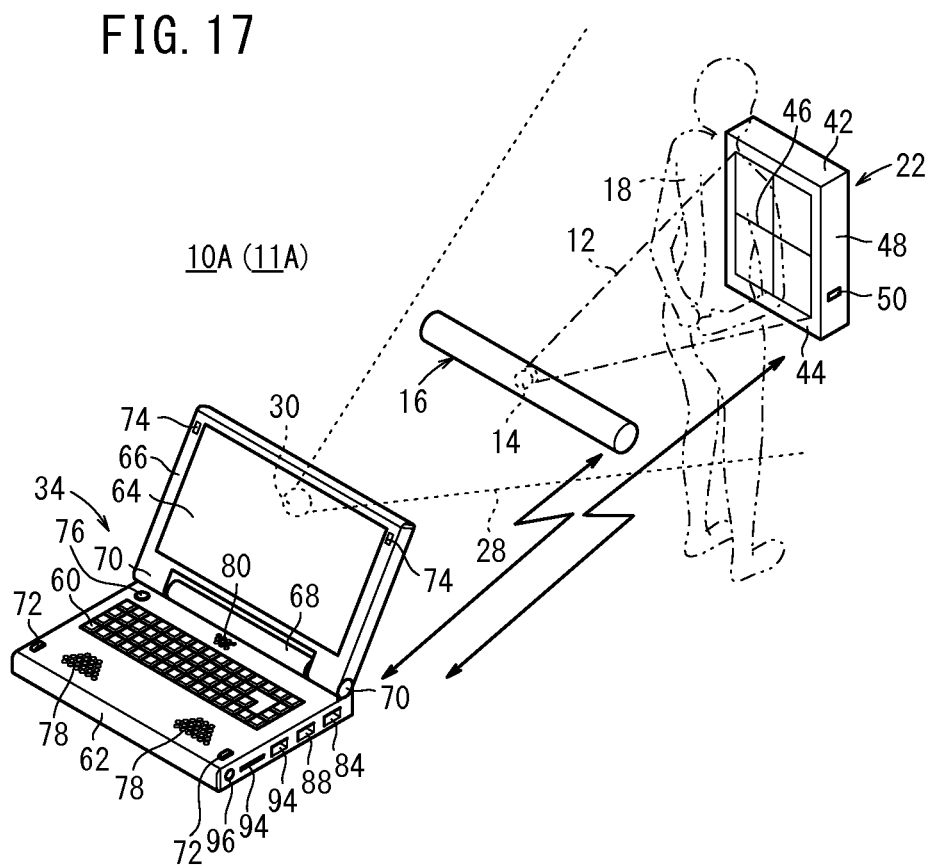
FIG. 17 is a perspective view of a radiographic image capturing apparatus and a radiographic image capturing system according to a first modification.

As shown in FIG. 17, a radiographic image capturing apparatus 10A and a radiographic image capturing system 11A according to a first modification differ from the exemplary embodiment shown in FIGS. 1 through 16, in that signals are sent and received between the portable information terminal 34, the radiation source device 16, and the cassette device 22 by way of wireless communications.

In this case, since the portable information terminal 34, the radiation source device 16, and the cassette device 22 are connected wirelessly over the same link (communications link), USB cables for sending and receiving signals are unnecessary. Owing thereto, no obstacles are presented that impede the work of the operator 32. Accordingly, the operator 32 can carry out work with increased efficiency. Further, by rendering the USB cables unnecessary, the number of parts of the radiographic image capturing apparatus 10A are reduced, and assembly of the apparatus at the site is facilitated.

As noted above, since the portable information terminal 34, the radiation source device 16, and the cassette device 22 exist within the same communications link, transmission and reception of signals for the camera images, radiographic images, etc., to and from the communication unit 104 (see FIGS. 1 and 11) of the medical organization 40 can be performed via any one of the communication units 136, 170, 218 (see FIG. 10).

Apart from transmission and reception of signals between the portable information terminal 34, the radiation source device 16, and the cassette device 22 being carried out by way of wireless communications, the first modification is the same as the exemplary embodiment of FIGS. 1 through 16. Therefore, the various effects and advantages apart from those pertaining to transmission and reception of signals can easily be obtained. Further, with the first modification, instead of the aforementioned wireless communications, signals may be sent and received by way of optical wireless communications using infrared radiation or the like.

Second Modification

Figure 18:
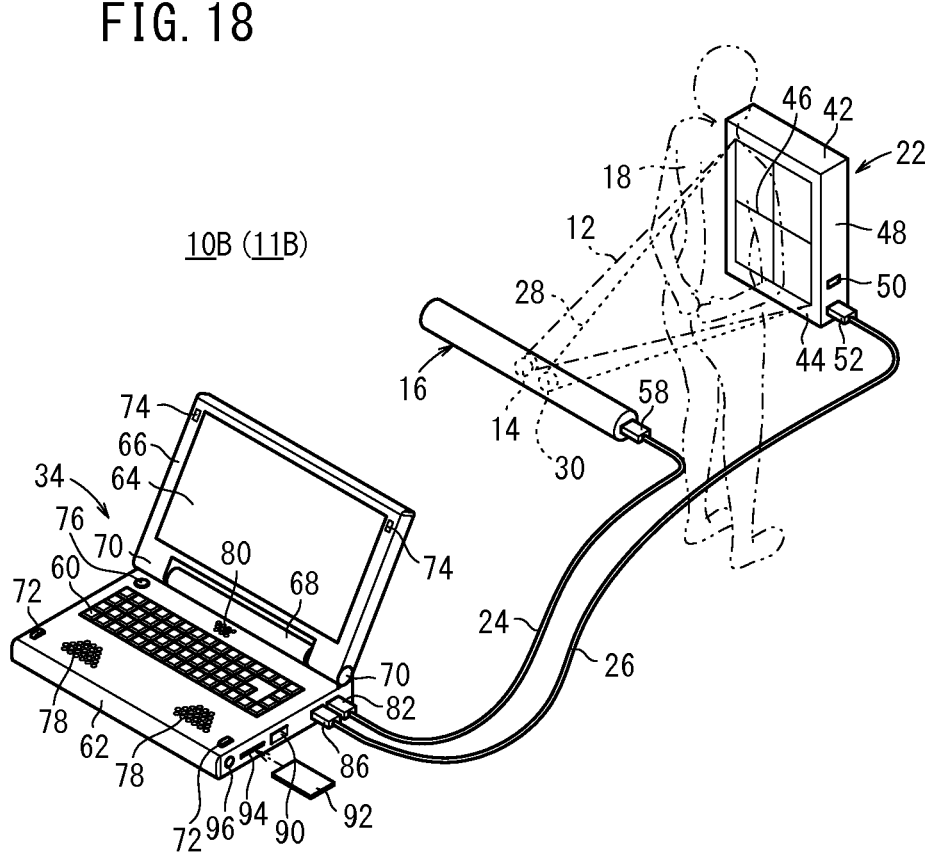
FIG. 18 is a perspective view of a radiographic image capturing apparatus and a radiographic image capturing system according to a second modification.

A radiographic image capturing apparatus 10B and a radiographic image capturing system 11B according to a second modification differ from the exemplary embodiments shown in FIGS. 1 through 17, in that, as shown in FIG. 18, the web camera 30 is accommodated in the radiation source device 16, and the web camera 30 captures an image of the guide lines 46 as the image capturing region 28.

Accordingly, with the second modification, the web camera 30 and the radiation source device 16 are constructed integrally. In this case, integral construction of the web camera 30 and the radiation source device 16 is not limited to the structure shown in FIG. 18, in which the web camera 30 is incorporated in the radiation source device 16, but may also include a configuration in which the web camera 30 and the radiation source device 16 are joined together (connected) integrally at least at times that the radiographic image capturing apparatus 10B is being used.

More specifically, the web camera 30 may be made integral with the radiation source device 16 in any of the following configurations (1) through (3). (1) The web camera 30 is connected electrically to the radiation source device 16 by a cable, which is included in the radiographic image capturing apparatus 10B. (2) The web camera 30 is connected to the radiation source device 16 by a cable, which is provided by the operator 32. (3) During times that the radiographic image capturing apparatus 10B is in use, the radiation source device 16 is coupled to the web camera 30, and at times that the radiographic image capturing apparatus 10B is serviced for maintenance or is not in use, the web camera 30 can be spaced (or separated) from the radiation source device 16.

In configuration (3) as well, in order to enable the web camera 30 to be spaced from the radiation source device 16 at times that the radiographic image capturing apparatus 10B is serviced for maintenance or is not in use, the web camera 30 may be coupled to the radiation source device 16 by a coupling means such as a clip or the like. Owing thereto, the web camera 30 is coupled to the radiation source device 16 by the coupling means only at times that the radiographic image capturing apparatus 10 is in use. Further, the coupling means may be equipped with a ball joint to allow the web camera 30, which is coupled to the radiation source device 16, to freely change the orientation thereof. If the web camera 30 is coupled to the radiation source device 16 by the coupling means, it is a matter of course that the web camera 30 and the radiation source device 16 must be connected to each other through a wired link (e.g., a USB cable) or a wireless link.

Furthermore, if the web camera 30 and the radiation source device 16 are connected to each other through a cable, then since the web camera 30 can be placed independently in any desired position, the web camera 30 can be positioned with greater freedom than if the web camera 30 were incorporated in the radiation source device 16.

Further, in the second modification, only the location of the guide lines 46 is displayed in the camera image of the web camera 30, and therefore, in the case that the camera image is sent to the portable information terminal 34 from the web camera 30 via the USB cable 24, and the camera image is displayed on the display unit 64 of the portable information terminal 34, the doctor 38 can easily determine whether or not the region to be imaged of the subject 18 is included within the outer frame of the guide lines 46.

Apart from the web camera 30 being incorporated in the radiation source device 16, the second modification is the same as the exemplary embodiment of FIGS. 1 through 16, and therefore, the various effects and advantages of FIGS. 1 through 16, apart from those pertaining to incorporation of the web camera 30 in the radiation source device 16, can easily be obtained.

Third Modification

Figure 19:
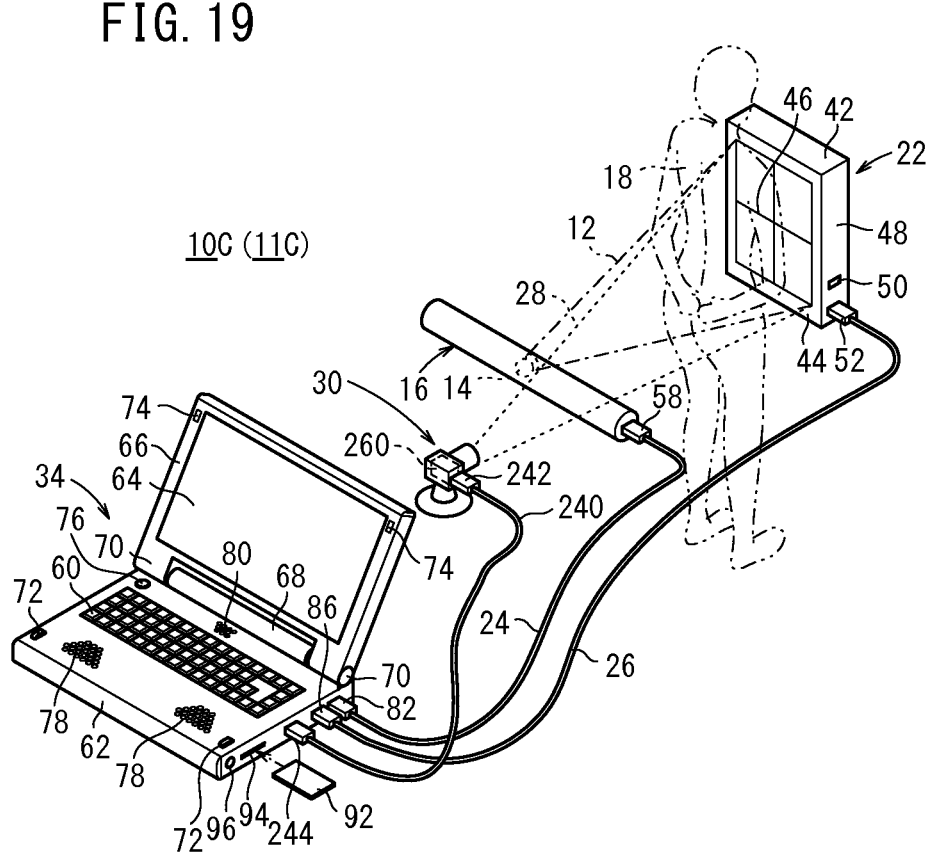
FIG. 19 is a perspective view of a radiographic image capturing apparatus and a radiographic image capturing system according to a third modification.

A radiographic image capturing apparatus 10C and a radiographic image capturing system 11C according to a third modification differ from the exemplary embodiments shown in FIGS. 1 through 18, in that, as shown in FIG. 19, a separate web camera 30 is connected electrically and joined integrally with the portable information terminal 34 by a USB cable 240 having connectors 242, 244.

In this case, the web camera 30 is supplied with electric power from the battery 220 through the USB cable 240, whereas the camera image is sent to the portable information terminal 34 via the USB cable 240. Accordingly, by integrally constructing the separate web camera 30 and the portable information terminal 34 in this manner, although the number of parts of the radiographic image capturing apparatus 10C increases, the advantages of the apparatus shown in FIGS. 1 through 16 can easily be obtained. Further, because the web camera 30 can be arranged independently at any desired position within the range allowed by the length of the USB cable 240, in comparison to a structure in which the web camera 30 is incorporated in the portable information terminal 34, the degree of freedom in positioning the web camera 30 can be increased. In FIG. 19, the communication unit 260 is shown as being mounted on the web camera 30. In this case, with the communication unit 260, transmission and reception of signals such as radiographic images and camera images, etc., may be carried out directly between the communication unit 260 and the communication unit 104 of the medical organization 40 via the network 36 (see FIGS. 1 and 10).

Fourth Modification

Figure 20:
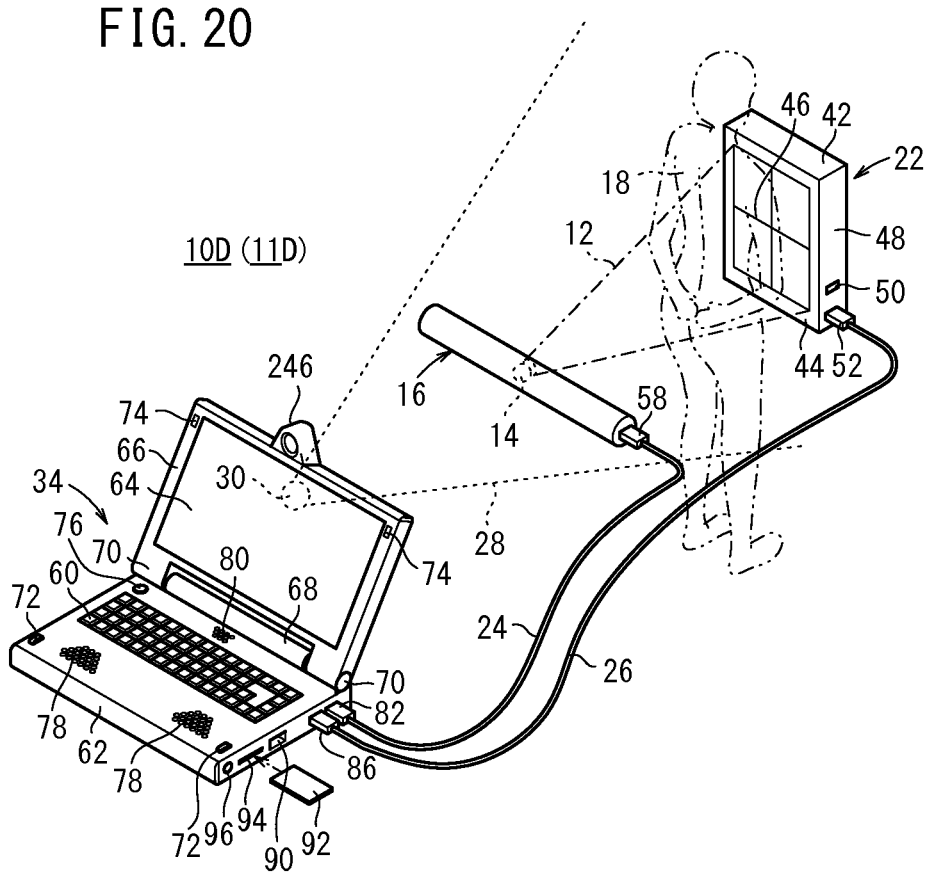
FIG. 20 is a perspective view of a radiographic image capturing apparatus and a radiographic image capturing system according to a fourth modification.

A radiographic image capturing apparatus 10D and a radiographic image capturing system 11D according to a fourth modification differ from the exemplary embodiment shown in FIGS. 1 through 16, in that, as shown in FIG. 20, a web camera 246 also is provided in the lid 66 for capturing an image of the operator 32 during times that the portable information terminal 34 is operated.

In this case, the portable information terminal 34 transmits to the medical organization (see FIGS. 1 and 11) the camera image from the web camera 246 (i.e., the image of the operator 32) by way of wireless communications over the network 36. Therefore, the operator 32 can seek instructions concerning capturing of images while observing the image of the doctor 38 displayed on the display unit 64, whereas the doctor 38 can issue instructions to the operator 32 while observing the image of the operator 32 displayed on the display unit 112. Accordingly, the operator 32 can feel a sense of proximity to the doctor 38 who is in a remote location such as the medical organization 40, whereas the doctor 38 can feel a sense of proximity to the operator 32 who is at the site, and thus the operator 32 and the doctor 38 can carry out image capturing preparations with increased confidence and security.

Further, because in other aspects, apart from the advantages that come about from providing the web camera 246, the fourth modification is the same as the exemplary embodiment of FIGS. 1 through 16, the various effects and advantages thereof can easily be obtained.

Fifth Modification

Figure 21:
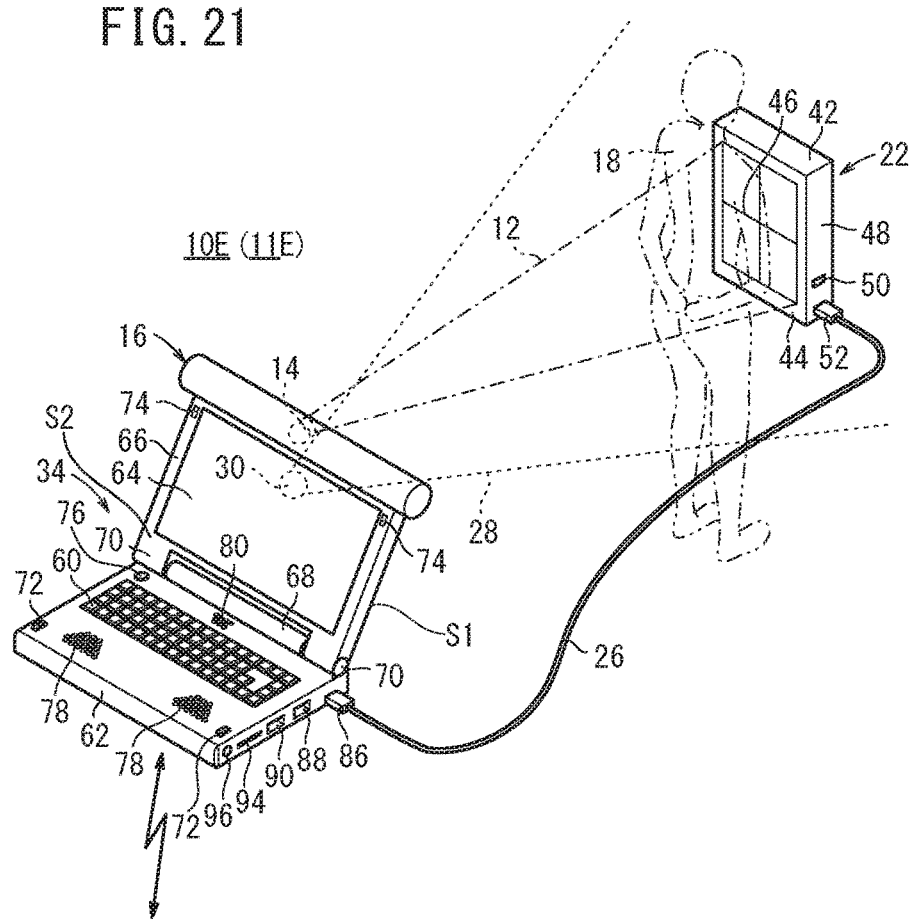
FIG. 21 is a perspective view of a radiographic image capturing apparatus and a radiographic image capturing system according to a fifth modification.

As shown in FIG. 21, a radiographic image capturing apparatus 10E and a radiographic image capturing system 11E according to a fifth modification differ from the exemplary embodiments shown in FIGS. 1 through 20, in that the radiation source device 16 is made integral with the lid 66 as a result of being joined thereto.

In this case, since the USB cable 24 is unnecessary, the radiographic image capturing apparatus 10E can be assembled and accommodated more easily at the site. Further, since the radiation source device 16 and the portable information terminal 34 are made integral with each other, the battery 134, the communication unit 136, and the radiation source controller 138 may be dispensed with. More specifically, the battery 220 is shared as a battery of the radiation source device 16, the control processor 222 is shared as a radiation source controller of the radiation source device 16, and the communication unit 218 is shared as a communication unit of the radiation source device 16. Thus, the radiation source device 16 is simplified in structure, thereby enabling the radiographic image capturing apparatus 10E to be made smaller in size as a whole.

Moreover, since the radiation source device 16 and the portable information terminal 34 are made integral with each other, the operator 32 can change the position and orientation of the portable information terminal 34 while viewing the display unit 64 on a second surface S2, or while operating the operating unit 60, thereby simultaneously adjusting the position and orientation of the radiation source device 16 with respect to the cassette device 22 and the subject 18. According to the fifth modification, therefore, the position and orientation of the radiation source device 16 with respect to the cassette device 22 and the subject 18 can be adjusted easily.

In FIG. 21, the web camera 30 is incorporated in the lid 66 on a first surface S1. However, the web camera 30 may also be incorporated in the radiation source device 16. Further, since the fifth modification is the same as the exemplary embodiments shown in FIGS. 1 through 20, apart from the fact that the radiation source device 16 and the portable information terminal 34 are made integral with each other, the fifth modification offers the same advantages as the exemplary embodiments shown in FIGS. 1 through 20, except that the radiation source device 16 and the portable information terminal 34 are made integral with each other.

Sixth Modification

Figure 22:
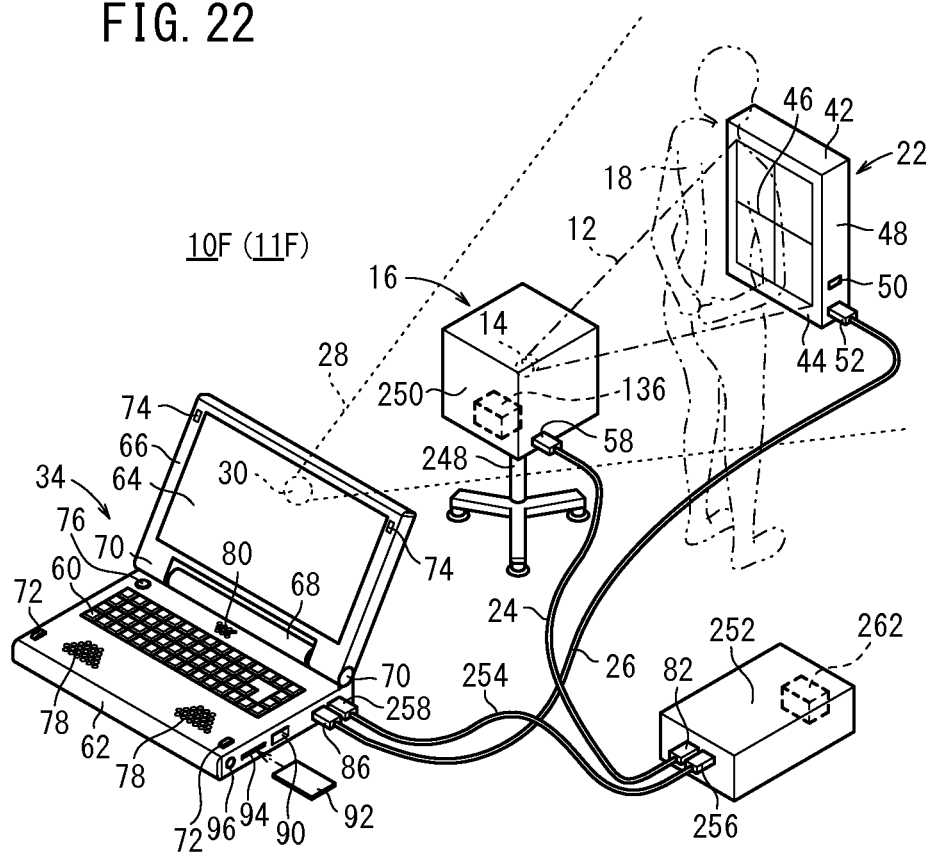
FIG. 22 is a perspective view of a radiographic image capturing apparatus and a radiographic image capturing system according to a sixth modification.

As shown in FIG. 22, a radiographic image capturing apparatus 10F and a radiographic image capturing system 11F according to a sixth modification differ from the exemplary embodiments shown in FIGS. 1 through 21, in that the radiation source 14 comprises a conventional thermionic-emission radiation source, and the radiographic image capturing apparatus 10F includes a high-voltage power supply 252 for energizing a filament of the radiation source 14.

In this case, the radiation source 14 and the communication unit 136 are housed in a casing 250, which is mounted on the upper end of a stand 248, and the casing 250 is electrically connected to the high-voltage power supply 252 by the USB cable 24. Further, the high-voltage power supply 252 and the portable information terminal 34 are electrically connected to each other by a USB cable 254 having connectors 256 and 258. Accordingly, the portable information terminal 34 can control the high-voltage power supply 252 to cause the radiation source 14 to emit radiation 12.

According to the sixth modification, the radiographic image capturing apparatus 10F is relatively large in size and has a relatively large number of parts, because the radiographic image capturing apparatus 10F includes a conventional thermionic-emission radiation source. However, the sixth modification offers the same advantages as those of the exemplary embodiment shown in FIGS. 1 through 16, except that the radiation source 14 is a thermionic-emission type of radiation source.

As shown in FIG. 22, the high-voltage power supply 252 includes a communication unit 262, which is capable of sending and receiving signals representing radiographic images, camera images, etc., to and from the communication unit 104 of the medical organization 40 via the network 36 (see FIGS. 1 and 10).

Seventh Modification

Figure 23:
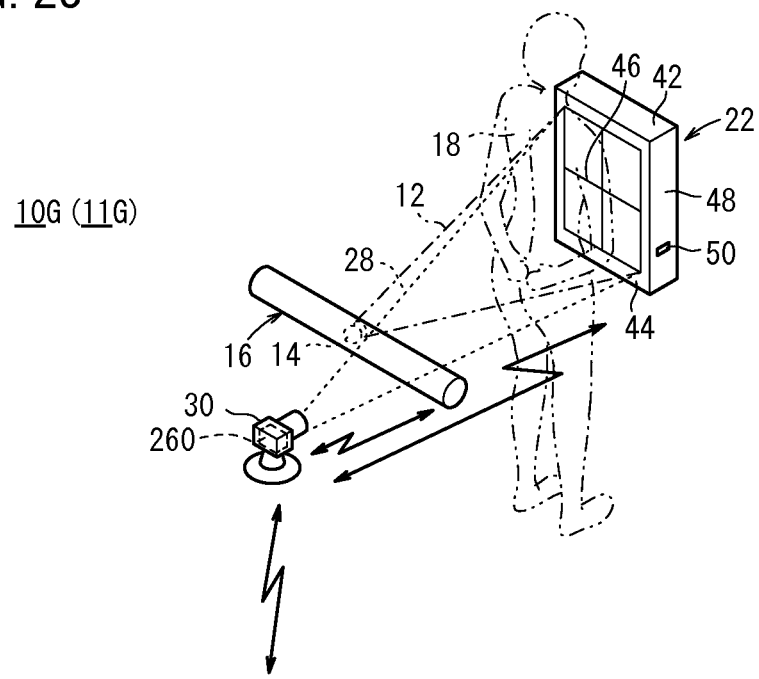
FIG. 23 is a perspective view of a radiographic image capturing apparatus and a radiographic image capturing system according to a seventh modification.

As shown in FIG. 23, a radiographic image capturing apparatus 10G and a radiographic image capturing system 11G according to a seventh modification differ from the exemplary embodiments shown in FIGS. 1 through 22, in that the portable information terminal 34 is not provided, but rather, the radiographic image capturing apparatus 10G is constituted by a separate web camera 30, the radiation source device 16, and the cassette device 22, and transmission and reception of signals therebetween is carried out by way of wireless communications.

In this case, since the radiation source device 16, the cassette device 22, and the web camera 30 are connected wirelessly over a common communications link, transmission and reception of signals including camera images, radiographic images, etc., with the communication unit 104 (see FIGS. 1 and 11) of the medical organization 40 may be performed through any one of the communication units from among the communication unit 260 of the web camera 30 and the communication units 136, 170 (see FIG. 10). For example, the web camera 30 may transmit camera images directly to the medical organization 40 from the communication unit 260 over the network 36 (see FIGS. 1 and 10), or alternatively, the camera images may be transmitted indirectly from the communication unit 260 to the medical organization 40 by way of the communication unit 170 of the cassette device 22, or by way of the communication unit 136 of the radiation source device 16.

Further, because the web camera 30 is arranged independently, the web camera 30 can be disposed in any desired position, and accordingly, the degree of freedom in positioning the web camera 30 can be enhanced.

Moreover, in the seventh modification, a synchronization control signal may be generated by the radiation source controller 138 of the radiation source device 16 or by the cassette controller 168 of the cassette device 22, or alternatively, may be supplied from the console 106 via the communication unit 104, the antenna 102, and the network 36.

In this case as well, the doctor 38 is able to observe the camera image from the web camera 30. Further, by providing the speaker 78 and the microphone 80 in the web camera 30, the radiation source device 16, or the cassette device 22, the operator 32 can seek instructions and advice pertaining to image capturing from the doctor 38, and such instructions can be given to the operator 32 from the doctor 38. More specifically, in the seventh modification, because the display unit 64 is not provided, image capturing preparations according to instructions from the doctor 38 are carried out by way of the operator 32 listening to voice messages of the doctor 38 from the speaker 78.

Apart from the portable information terminal 34 not being provided, and the fact that transmission and reception of signals between the web camera 30, the radiation source device 16 and the cassette device 22 are carried out by way of wireless communications, the seventh modification is essentially the same as the exemplary embodiment of FIGS. 1 through 16, and therefore, aside from the advantages that come about due to the absence of the portable information terminal 34 and by wireless transmission and reception of signals, the same advantages and effects of the exemplary embodiment of FIGS. 1 through 16 can be obtained.

Eighth Modification

Figure 24:
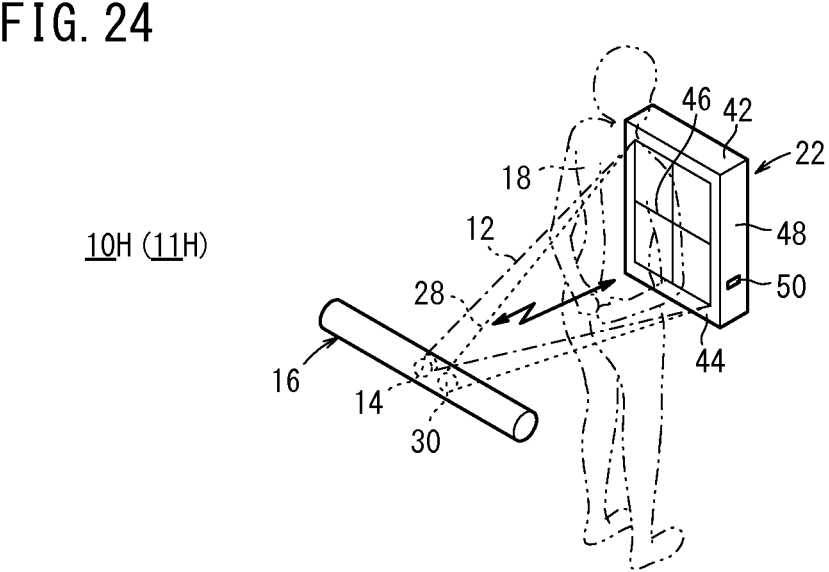
FIG. 24 is a perspective view of a radiographic image capturing apparatus and a radiographic image capturing system according to an eighth modification.

As shown in FIG. 24, a radiographic image capturing apparatus 10H and a radiographic image capturing system 11H according to an eighth modification differ from the seventh embodiment shown in FIG. 23, in that the web camera 30 is incorporated in the radiation source device 16.

In this case, similar to the second modification shown in FIG. 18, the web camera 30 captures an image of the guide lines 46 as the image capturing region 28.

Further, with the eighth modification, since the radiation source device 16 and the cassette device 22 are connected wirelessly over a common communications link, transmission and reception of signals including camera images, radiographic images, etc., with the communication unit 104 (see FIGS. 1 and 11) of the medical organization 40 may be performed through any one of the communication units from among the communication units 136, 170 (see FIG. 10). For example, the web camera 30 may transmit camera images directly to the medical organization 40 from the communication unit 136 over the network 36, or alternatively, the camera images may be transmitted indirectly from the communication unit 136 to the medical organization 40 by way of the communication unit 170 of the cassette device 22.

Furthermore, with the eighth modification, by incorporating the web camera 30 internally in the radiation source device 16, the number of parts can be further reduced. Apart from the web camera 30 being incorporated in the radiation source device 16, the eighth modification is essentially the same as the seventh modification shown in FIG. 23, and therefore, aside from the advantages that come about by constructing the web camera 30 integrally with the radiation source device 16, the same advantages and effects of the seventh modification of FIG. 23 can be obtained.

Ninth Modification

Figure 25:
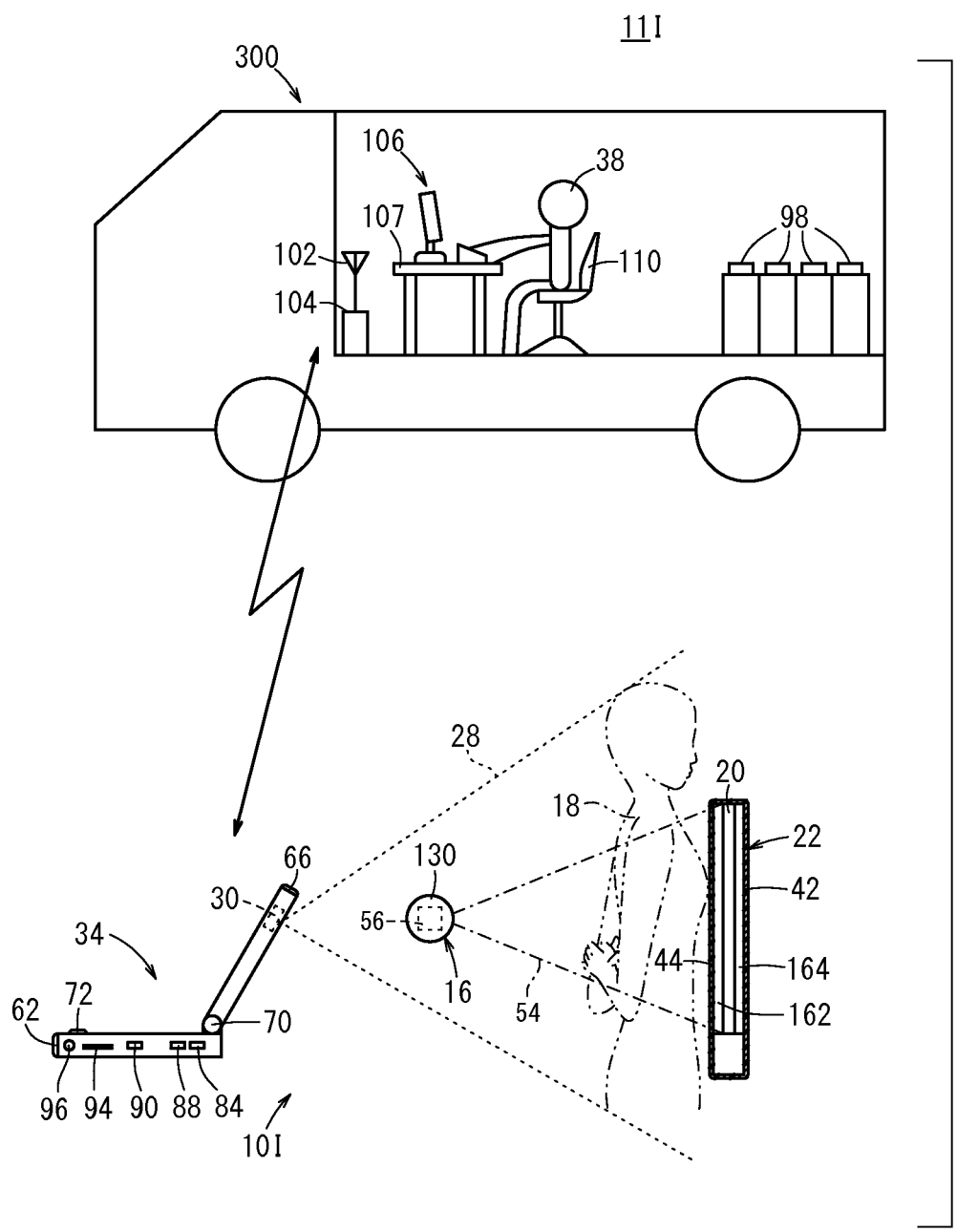
FIG. 25 is a structural view of a radiographic image capturing apparatus and a radiographic image capturing system according to a ninth modification.

As shown in FIG. 25, a radiographic image capturing apparatus 10I and a radiographic image capturing system 11I according to a ninth modification differ from the exemplary embodiments shown in FIGS. 1 through 24, in that the console 106 and a plurality of attaché cases 98, each of which houses therein the radiographic image capturing apparatus 10I, are provided in a medical checkup car 300 (waiting location) in which the doctor 38 is available, and the operator 32 (see FIG. 5) carries at least one of the attaché cases 98 from the medical checkup car 300 to the site. The cabin of the medical checkup car 300 where the doctor 38 is available serves as a waiting location from which the doctor 38 is unable to observe the subject 18 directly.

In this case as well, the radiographic image capturing apparatus 10I, which has been carried to the site, and the communication unit 104 in the medical checkup car 300 are capable of sending and receiving signals therebetween by way of wireless communications. For example, the radiographic image capturing apparatus 10I can send wireless signals representing camera images and radiographic images to the communication unit 104 by way of wireless communications. Therefore, the radiographic image capturing apparatus 10I offers the same advantages as the exemplary embodiments shown in FIGS. 1 through 24. Although the radiographic image capturing apparatus 10I and the communication unit 104 are illustrated in FIG. 25 as sending and receiving signals directly therebetween by way of wireless communications, the radiographic image capturing apparatus 10I and the communication unit 104 may also send and receive signals therebetween by way of wireless communications via the network 36 (see FIGS. 1 and 10).

Tenth Modification

As shown schematically in FIGS. 26A through 30B, a radiographic image capturing apparatus 10J and a radiographic image capturing system 11J according to a tenth modification differ from the exemplary embodiments shown in FIGS. 1 through 25, in that radiation 12a to 12c with an irradiation range narrower than that of the radiation 12 (see FIG. 1) is irradiated through the subject 18 simultaneously or sequentially from the radiation source device 16 to the cassette device 22.

In the tenth modification, with respect to radiation applied at the disaster site or the home care treatment site, the radiation intensity thereof is set to be weak for the purpose of safety (i.e., to prevent unnecessary or accidental exposure to radiation). In addition, image capturing of the subject 18 is performed effectively by the radiation 12a to 12c within a narrow irradiation range, which is narrower than that of the radiation 12, in a condition in which the radiation source device 16 is placed in close proximity to the cassette device 22 with a short SID (source to image distance).

Figure 26A:
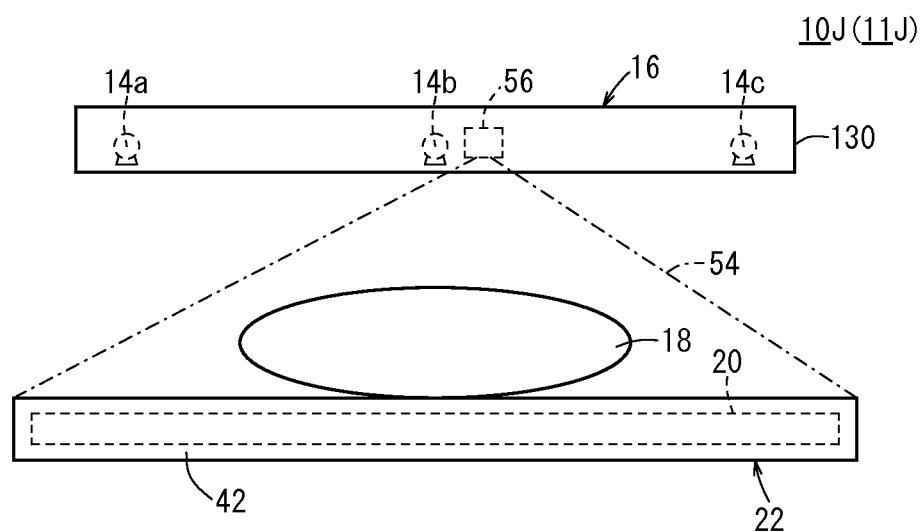
FIGS. 26A and 26B are partial structural views of a radiographic image capturing apparatus and a radiographic image capturing system according to a tenth modification.
Figure 26B:
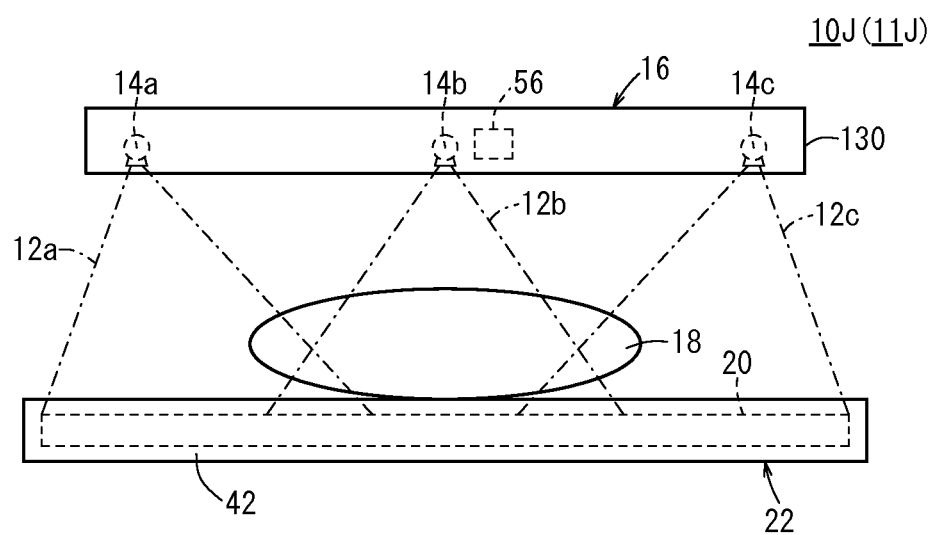
Figure 27A:
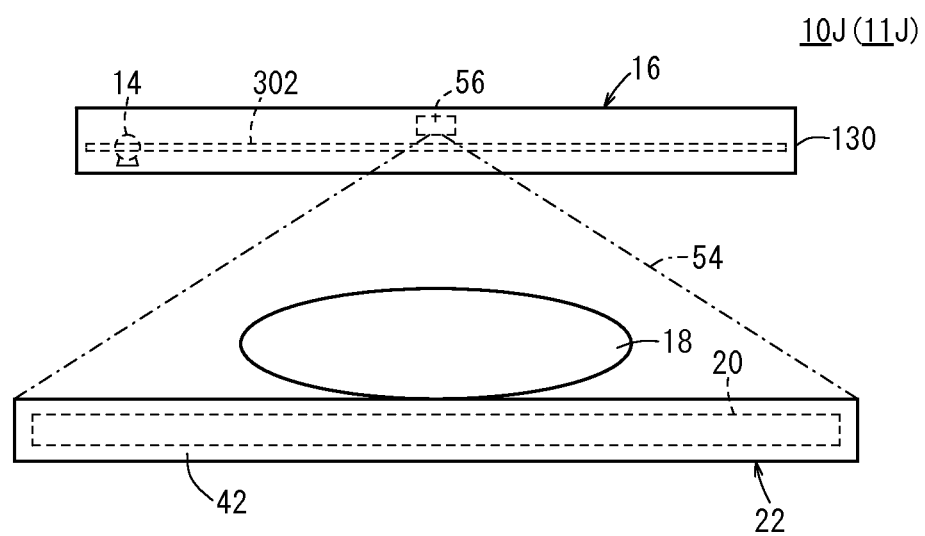
FIGS. 27A and 27B are partial structural views of a radiographic image capturing apparatus and a radiographic image capturing system according to the tenth modification.
Figure 27B:
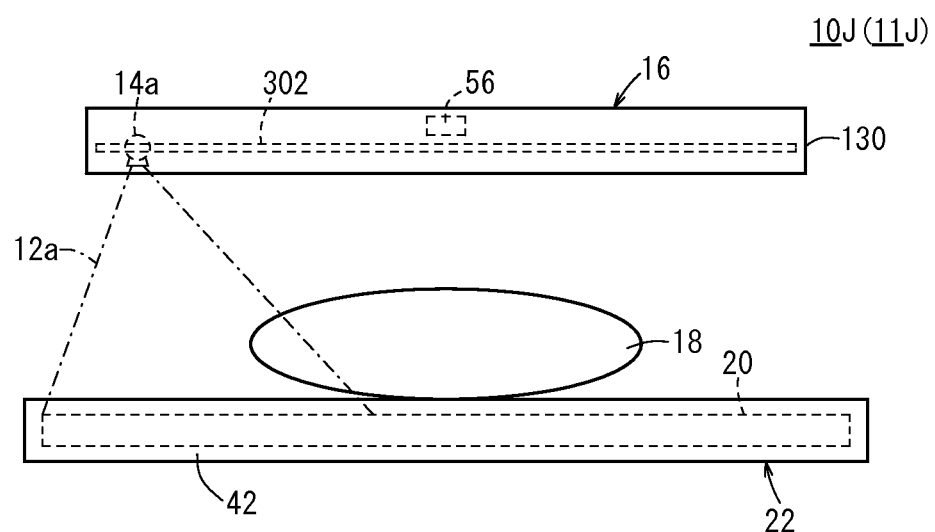
Figure 28A:
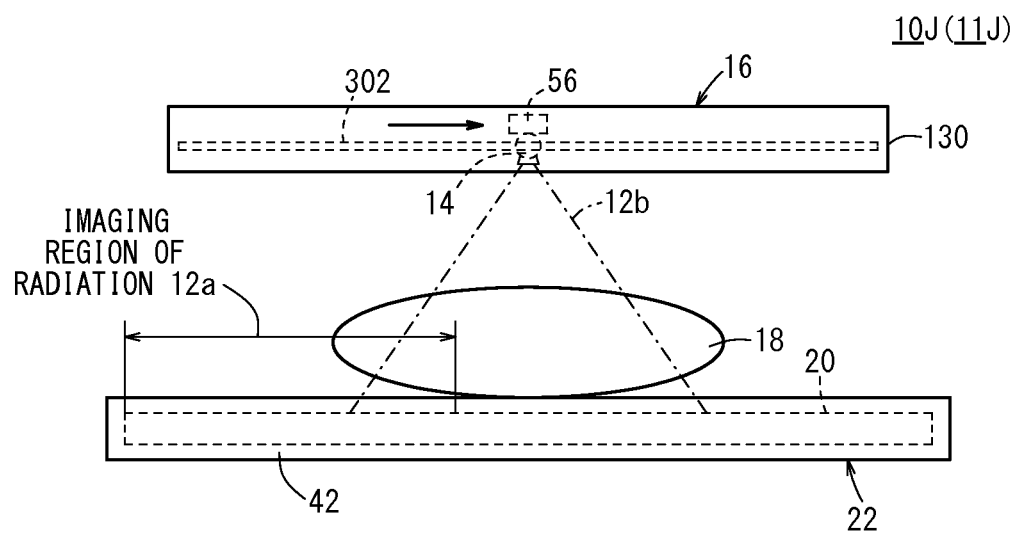
FIGS. 28A and 28B are partial structural views of a radiographic image capturing apparatus and a radiographic image capturing system according to the tenth modification.
Figure 28B:
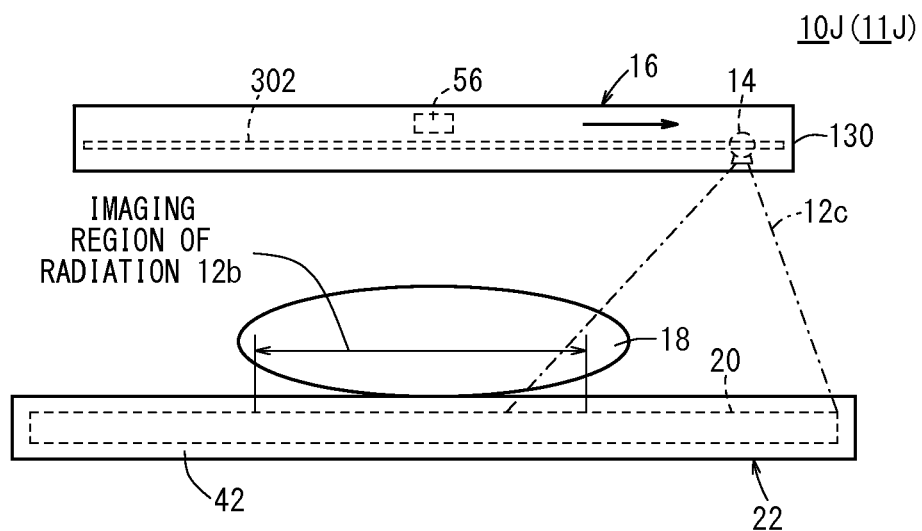
Figure 29A:
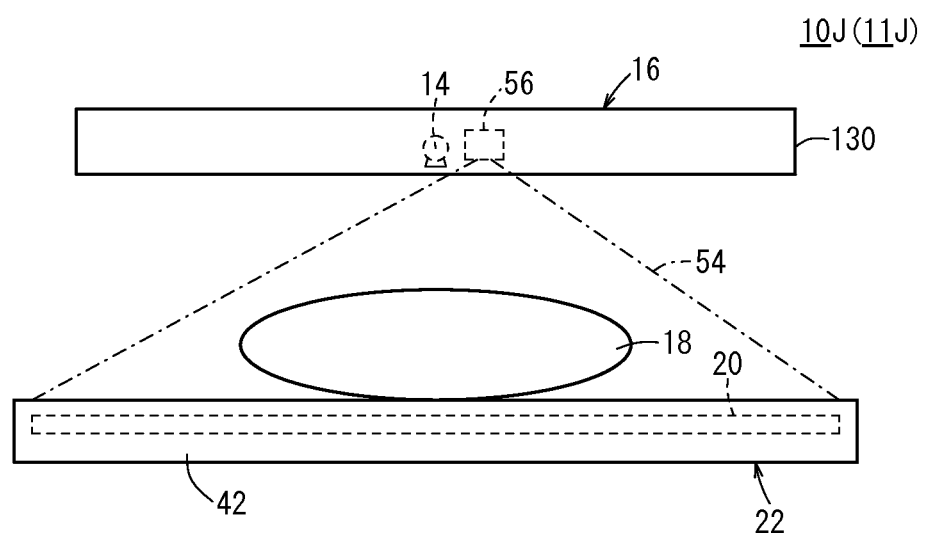
FIGS. 29A and 29B are partial structural views of a radiographic image capturing apparatus and a radiographic image capturing system according to the tenth modification.
Figure 29B:
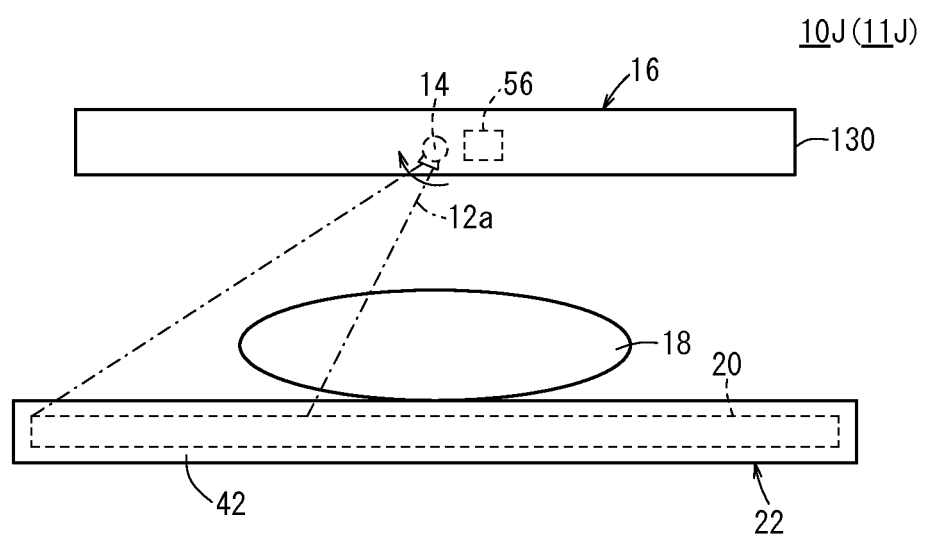
Figure 30A:
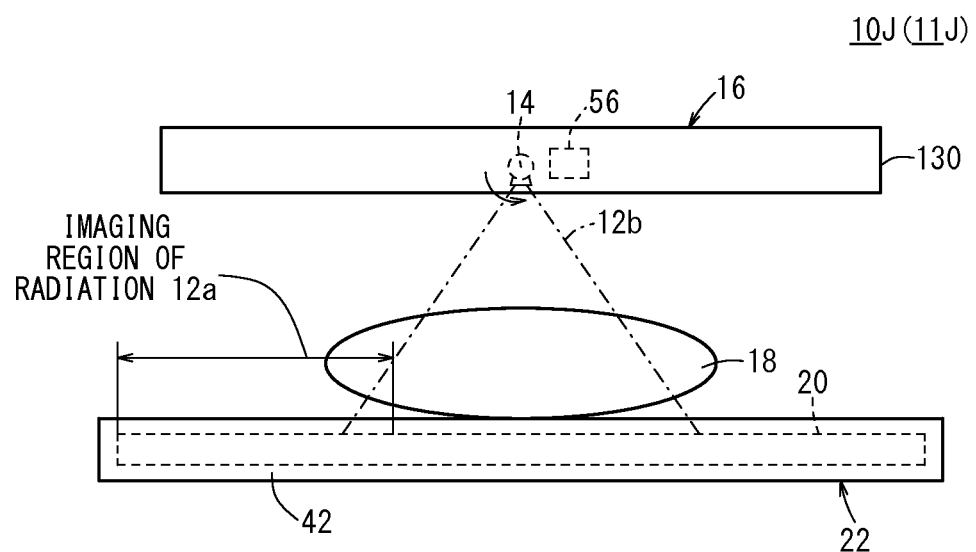
FIGS. 30A and 30B are partial structural views of a radiographic image capturing apparatus and a radiographic image capturing system according to the tenth modification.
Figure 30B:
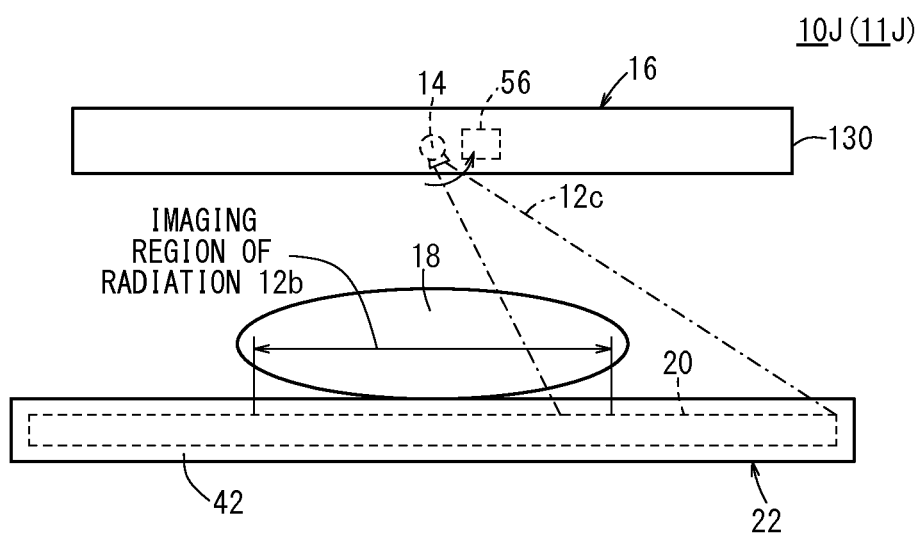

Initially, in the case of FIGS. 26A and 26B, a plurality of radiation sources 14a to 14c are accommodated at predetermined distances in the interior of the radiation source device 16, and after irradiation light 54 is output from the irradiated field lamp 56 and projected onto the irradiated surface 44 (see FIGS. 1, 7 and 16), radiation 12a to 12c is applied simultaneously to (the irradiated surface 44 of) the cassette device 22 from each of the radiation sources 14a to 14c. In this case, radiation 12a to 12c from each of the radiation sources 14a to 14c is output collectively such that a portion of the radiation 12a and a portion of the radiation 12b, and also a portion of the radiation 12b and a portion of the radiation 12c overlap one another. Consequently, each of such radiations 12a to 12c can be applied reliably and without gaps with respect to the total region within the outer frame of the guide lines 46. As a result, even though the radiation intensity is set to be weak, image capturing of the subject 18 can be carried out reliably.

In the case of FIGS. 27A to 28B, inside the radiation source device 16, a rail 302 is disposed along a longitudinal direction of the radiation source device 16, and the radiation source 14 is constituted so as to be movable along the rail 302. In this case, after irradiation light 54 is output from the irradiated field lamp 56 and projected onto the irradiated surface 44 (see FIGS. 1, 7, and 16), the radiation source 14 moves along the rail 302, and radiation 12a to 12c is applied repeatedly at predetermined positions after movement thereof. At this time, the radiation source 14 is moved, and radiation 12a to 12c from the radiation source 14 is output at the positions shown in FIGS. 27B, 28A, and 28B, such that a portion of the radiation 12a and a portion of the radiation 12b, and also a portion of the radiation 12b and a portion of the radiation 12c overlap one another. In this case as well, since each of such radiations 12a to 12c can be applied reliably and without gaps with respect to the total region within the outer frame of the guide lines 46, even though the radiation intensity is set to be weak, image capturing of the subject 18 can be carried out reliably.

In the case of FIGS. 29A through 30B, after irradiation light 54 is output from the irradiated field lamp 56 and projected onto the irradiated surface 44 (see FIGS. 1, 7 and 16), the radiation source 14 is rotated by a non-illustrated rotation mechanism, and after rotation thereof, radiation 12a to 12c is applied repeatedly at respective predetermined angles. At this time, the radiation source 14 is rotated to the angles shown in FIGS. 29B, 30A, and 30B, and radiation 12a to 12c is output such that a portion of the radiation 12a and a portion of the radiation 12b, and also a portion of the radiation 12b and a portion of the radiation 12c overlap one another. In this case as well, since each of such radiations 12a to 12c can be applied reliably and without gaps with respect to the total region within the outer frame of the guide lines 46, even though the radiation intensity is set to be weak, image capturing of the subject 18 can be carried out reliably.

Further, according to the tenth modification, in the radiographic image obtained from the radiation 12a to 12c, at the location where the radiation 12a and the radiation 12b overlap, and at the location where the radiation 12b and the radiation 12c overlap, a known type of corrective process, such as shading correction or the like, may be implemented thereon.

Further, in the examples of FIGS. 27A to 30B, since each of such radiations 12a to 12c may be applied reliably and without gaps with respect to the total region within the outer frame of the guide lines 46, it is acceptable if at least two of such radiation sources 14a to 14c are provided. On the other hand, the sequence of movement or rotation of the radiation source 14, the positions thereof after movement, or the angles thereof after rotation are not limited to the sequence, positions, and angles shown in FIGS. 27B to 28B and 29B to 30B, and the sequence, positions, and angles thereof may be set in other suitable ways.

Further, in the tenth modification, aside from the radiation 12a to 12c being applied simultaneously or sequentially, in other respects the tenth modification is the same as the exemplary embodiments of FIGS. 1 through 25, and therefore, aside from radiating the subject 18 with respective radiations 12a to 12c, the tenth modification offers the same advantages as the exemplary embodiments shown in FIGS. 1 through 25.

FIGS. 31A to 33B illustrate a case in which positioning of the subject 18 is carried out using the web camera 30, which is incorporated in the radiation source device 16, and a case in which positional shifting or slippage of the radiation source device 16 is detected based on the camera image captured by the web camera 30, in the second and eighth modifications.

Figure 31A:
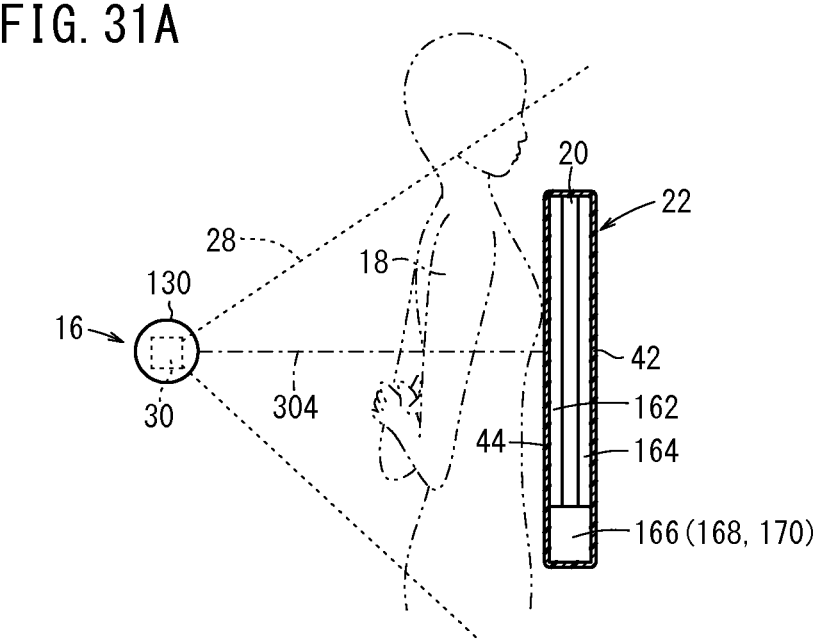
FIG. 31A is a partial structural view of a radiographic image capturing apparatus.
Figure 31B:
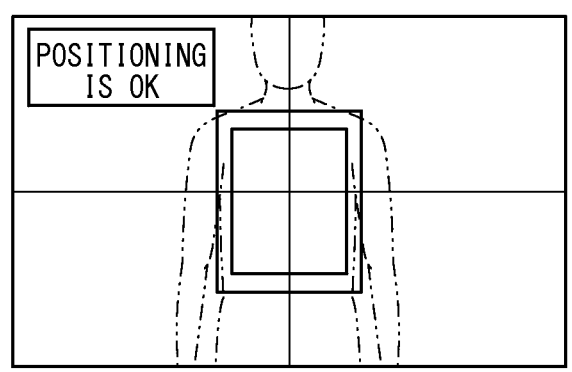
FIG. 31B is an exemplary view of a display screen of at least one of a portable information terminal and a console in the condition shown in FIG. 31A.

As shown in FIG. 31A, in the case that a horizontal axis 304 passing through the center of the web camera 30 and the central position of the guide lines 46 are substantially perpendicular, then as shown in FIG. 31B, the region to be imaged of the subject 18 and the cassette device 22 are displayed in the center of the camera image displayed on the display unit 64 of the portable information terminal 34 (see FIGS. 1 and 10), or on the display unit 112 of the console 106 (see FIGS. 1 and 11). Further, in FIG. 31B, the cross hairs in the camera image indicate a center position of the camera image, and assuming the horizontal axis 304 and the center position of the guide lines 46 are substantially perpendicular, the cross hairs and the center position of the guide lines 46 coincide with each other.

Accordingly, during image capturing preparations, while the operator 32 observes the camera image, by instructing the subject 18, or by adjusting the position of the radiation source device 16 such that the cross hairs coincide with the center position of the guide lines 46, even without visually confirming the subject 18 directly, positioning of the subject 18 can easily be carried out. Moreover, in the case of FIG. 31B, similar to the case of FIGS. 14A and 14B, by bringing the cross hairs and the center position of the guide lines 46 into substantial agreement with each other, the characters "POSITIONING IS OK" are displayed to indicate that image capturing preparations have been completed.

Figure 33A:
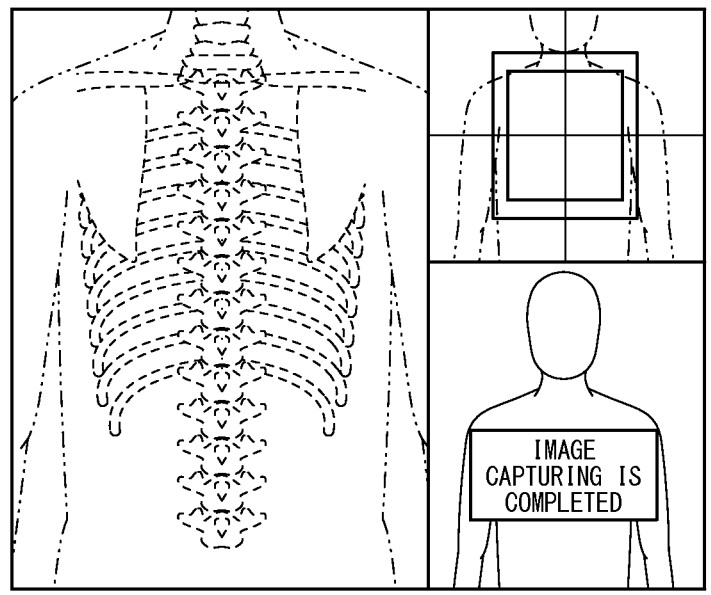
FIG. 33A is an exemplary view of a display screen of at least one of a portable information terminal and a console after completion of image capturing in the condition shown in FIG. 31A.

In addition, if image capturing is carried out in the condition shown in FIGS. 31A and 31B, then as shown in FIG. 33A, a radiographic image of a desired imaging region can reliably be obtained. FIG. 33A shows the content displayed on the display units 64, 112 following completion of image capturing, in which the radiographic image of the region to be imaged of the subject 18 is displayed in a large size. Together therewith, similar to the case of FIGS. 15A and 15B, a camera image of the subject 18 and the cassette device 22 after image capturing is displayed in a smaller size along with displaying the characters "IMAGE CAPTURING IS COMPLETED" for indicating that the image-capturing has been completed. Further, since following image capturing, it is desirable for the doctor to rapidly carry out radiographic image diagnosis, by displaying the radiographic image in a larger size than the other displayed content, radiographic image diagnosis can be performed quickly and effectively.

Figure 32A:
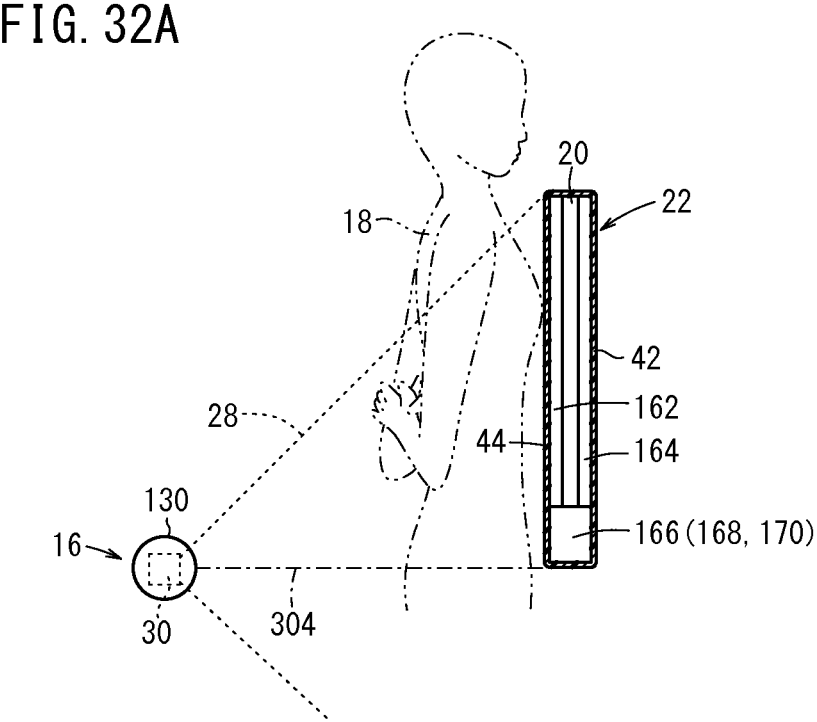
FIG. 32A is a partial structural view of a radiographic image capturing apparatus.
Figure 32B:
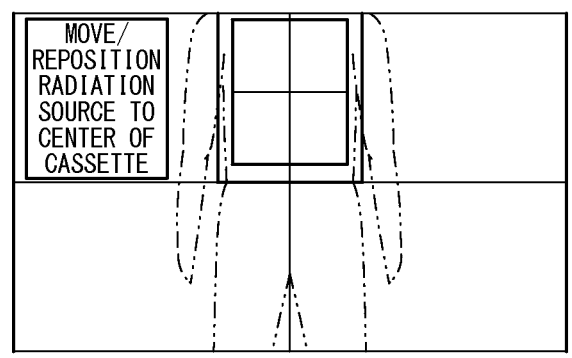
FIG. 32B is an exemplary view of a display screen of at least one of a portable information terminal and a console in the condition shown in FIG. 32A.

In contrast thereto, as shown in FIG. 32A, if the horizontal axis 304 and the center position of the guide lines 46 are not perpendicular and are significantly separated, then as shown in FIG. 32B, the cross hairs in the camera image and the center position of the guide lines 46 do not coincide with each other. Thus, the operator 32 can easily grasp that positional shifting of the radiation source device 16 with respect to the cassette device 22 has occurred.

Accordingly, while observing the camera image while image capturing preparations are carried out, the operator 32 can adjust the position of the radiation source device 16 so as to bring the cross hairs and the center position of the guide lines 46 into substantial agreement (i.e., so that the display content of FIG. 31B appears). Further, the operator 32 can reliably be notified of any positional shifting of the radiation source device 16 with respect to the cassette device 22. Further, similar to the case of FIG. 14C, as shown in FIG. 32B, at times that positional shifting of the radiation source device 16 with respect to the cassette device 22 occurs, the characters "MOVE/REPOSITION RADIATION SOURCE TO CENTER OF CASSETTE" are displayed to instruct the operator 32 to carry out image capturing preparations once again.

Figure 33B:
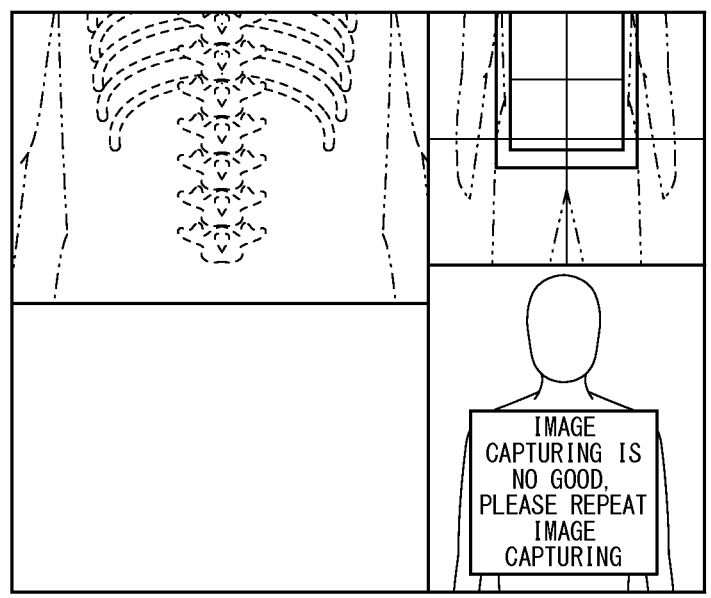
FIG. 33B is an exemplary view of a display screen of at least one of a portable information terminal and a console after completion of image capturing in the condition shown in FIG. 32A.

Incidentally, in the event that image capturing is carried out irrespective of the content displayed in FIG. 32B, or if shifting of the radiation source device 16 occurs during image capturing, then as shown in FIG. 33B, a radiographic image for which capturing was a failure is displayed together with the camera image of the subject 18 and the cassette device 22 after image capturing, and similar to the case of FIG. 15C, the characters "IMAGE CAPTURING IS NO GOOD, PLEASE REPEAT IMAGE CAPTURING" are displayed respectively on the display units 64, 112, for indicating image-recapturing. Accordingly, by confirming the displayed content, the operator 32 can easily comprehend that image capturing was a failure, and that recapturing of the image is necessary.

In the foregoing manner, in the case of FIGS. 31A through 33B, positioning of the subject 18 is carried out using the web camera 30 that is incorporated in the radiation source device 16, and together therewith, based on the camera image capturing by the web camera 30, positional shifting of the radiation source device 16 is detected. Owing thereto, during image capturing preparations, the operator 32 can reliably be notified of any positional shifting or slippage, so that image capturing preparations can be carried out effectively, together with enabling a desired radiographic image to be obtained reliably. Further, if by chance, even in the case that image capturing is a failure, a notification can reliably be given to repeat image capturing, thus enabling image recapturing to be performed swiftly.

Eleventh Modification

As shown in FIGS. 34 through 37B, a radiographic image capturing apparatus 10K and a radiographic image capturing system 11K according to an eleventh modification differ from the exemplary embodiments shown in FIGS. 1 through 33B, in that the radiation source device 16 includes a handle 310 to be gripped by the operator 32, which is disposed on a side of the radiation source device 16 opposite from a location thereof on which radiation 12 is output.

In this case, while the operator 32 grips the handle 310 with one hand, the radiation source device 16 incorporating the web camera 30 therein is directed toward the subject 18 and the cassette device 22. At the same time, the operator 32 can operate the portable information terminal 34 with the other hand while observing the display unit 64. At this time, the camera image captured by the web camera 30 is displayed on the display unit 64, and therefore, the operator 32 can carry out positioning of the subject 18 while observing the camera image and moving the radiation source device 16 to a desired position. Further, even in the case that radiation 12 is emitted while the operator 32 grips the handle 310, application of radiation 12 toward the operator 32 (exposure of the operator 32) can reliably be avoided.

The eleventh modification is particularly applicable and effective at disaster sites where several obstacles may be present. More specifically, at such disaster sites, since there are many obstacles, and it may be difficult to move the subject 18 due to injury of the subject 18 at the disaster site, as a practical matter, it is difficult to secure the radiation source device 16 and the cassette device 22 at given positions and to guide the subject 18 to a position between the radiation source device 16 and the cassette device 22. Accordingly, the radiation source device 16 and the cassette device 22 frequently need to be located at positions that are convenient to the subject 18. For this reason, although the operator 32 can direct the radiation source device 16 toward the subject 18, it may be difficult to observe the subject 18 directly due to the presence of obstacles. Consequently, it may not be easy to position the subject 18.

Thus, according to the eleventh modification, if the operator 32 grips the handle 310 with one hand and directs the radiation source device 16 toward the subject 18 and the cassette device 22, the web camera 30 captures a camera image of the subject 18 and the cassette device 22, and the captured camera image is displayed on the display unit 64. Accordingly, the operator 32 can easily operate the portable information terminal 34 with the other hand, or adjust the position of the radiation source device 16 and position the subject 18, while viewing the camera image displayed on the display unit 64.

Figure 35:
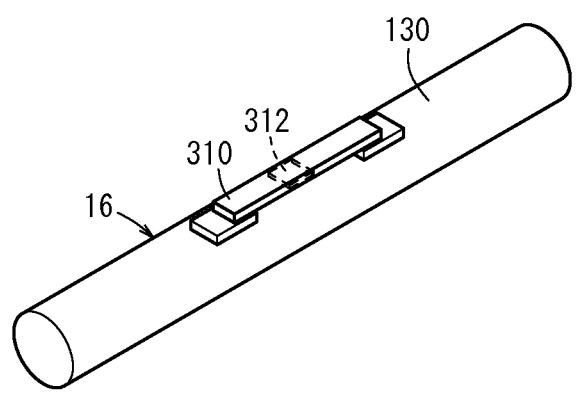
FIG. 35 is a perspective view of a radiation source device shown in FIG. 34.
Figure 36A:
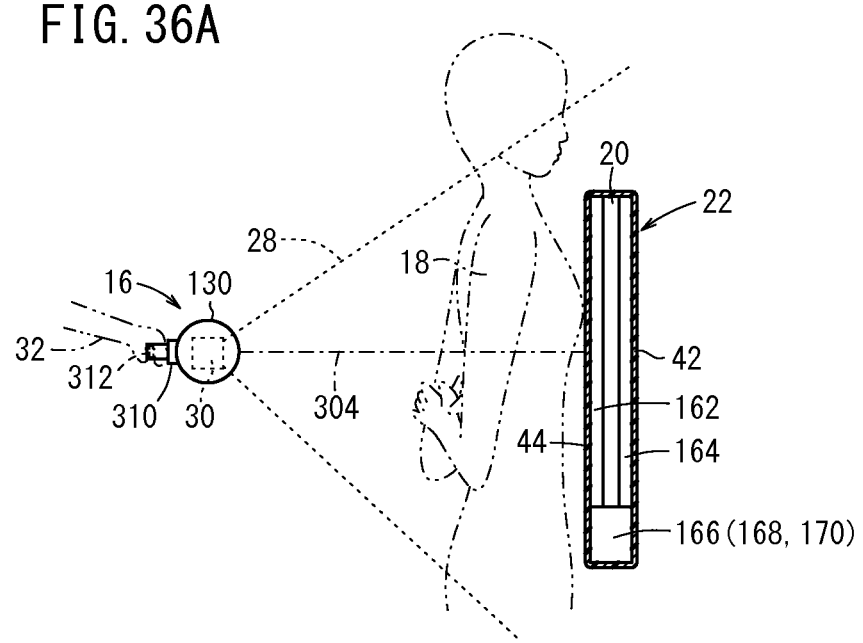
FIGS. 36A and 36B are partial structural views of a radiographic image capturing apparatus.
Figure 36B:
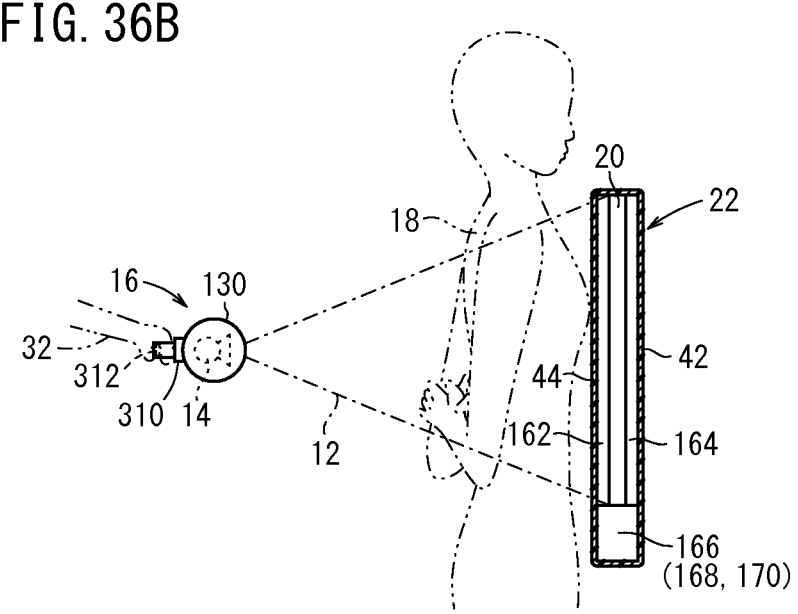

The handle 310 includes an electrostatic capacitance or resistance film type of touch sensor (gripping state detecting sensor) 312 (see FIGS. 35 through 36B). If the operator 32 grips the handle 310, the hand of the operator 32 comes into contact with a non-illustrated electrode constituting the touch sensor 312, whereupon, the touch sensor 312 outputs a detection signal to the radiation source controller 138 and the control processor 222 (see FIG. 10) based on contact between the operator's hand and the electrode. The radiation source controller 138 or the control processor 222 is able to activate the radiation source device 16 or operate the cassette device 22 based on the aforementioned detection signal.

Figure 37A:
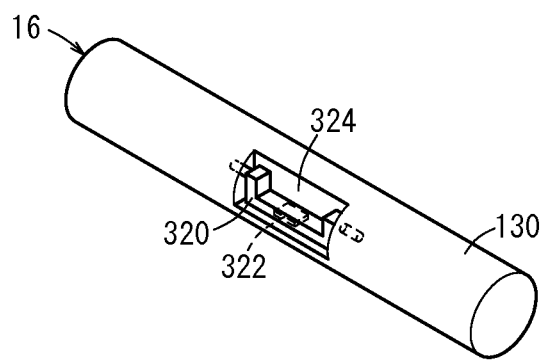
FIGS. 37A and 37B are perspective views showing other configurations of the radiation source device of FIG. 35.
Figure 37B:
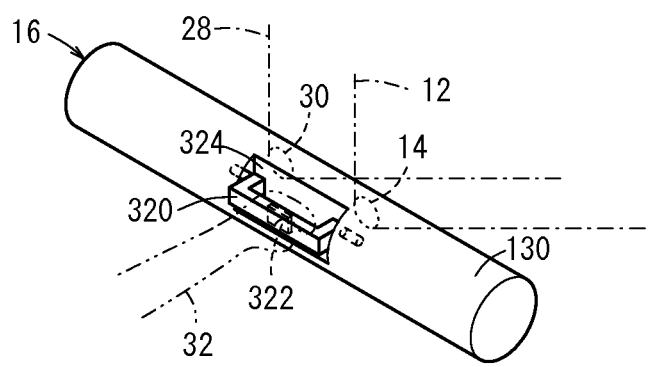

Further, as shown in FIGS. 37A and 37B, the radiation source device 16 may include a recess 324 defined in a side opposite from the location where radiation 12 is emitted, and a collapsible handle 320 may be disposed in the recess 324. A touch sensor 322, which has the same function as the touch sensor 312, may be incorporated in the handle 320. In a state in which the operator 32 is not carrying the radiation source device 16, the handle 320 is accommodated inside the recess 324 as shown in FIG. 37A. On the other hand, if the operator 32 turns the handle 320 about a proximal end, the handle 320 is raised out of the recess 324, so that the operator 32 can grip the handle 320. In this case as well, the handle 320 and the touch sensor 322 offer the same advantages as those of the handle 310 and the touch sensor 312 described above.

Further, in a case where the handle 320 is accommodated in the recess 324 (e.g., in a case where the radiation source device 16 is moved as shown in FIGS. 5 and 37A), the electrode of the touch sensor 322 is kept out of contact with the hand of the operator 32. Therefore, during activation of the radiation source device 16, the radiation source 14 can be prevented from emitting radiation 12 in error.

Apart from the features of the handles 310, 320 being provided on the radiation source device 16, the eleventh modification is the same as the exemplary embodiments shown in FIGS. 1 through 33B, and therefore, aside from the advantages that are brought about due to providing the handles 310, 320, the same effects and advantages of the embodiments of FIGS. 1 through 33B can easily be obtained.

Twelfth Modification

Figure 38:
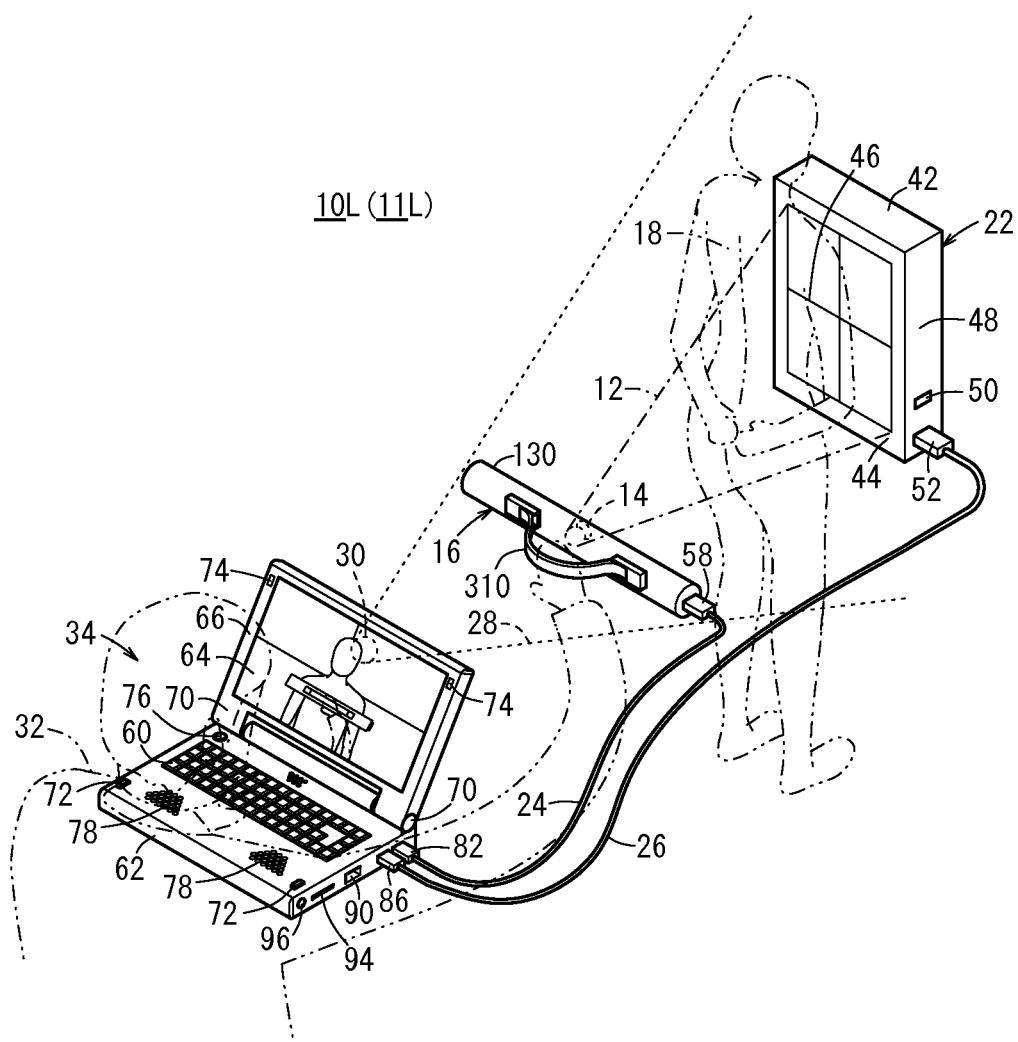
FIG. 38 is a partial structural drawing of a radiographic image capturing apparatus and a radiographic image capturing system according to a twelfth modification.

As shown in FIG. 38, a radiographic image capturing apparatus 10L and a radiographic image capturing system 11L according to a twelfth modification differ from the eleventh modification (see FIGS. 34 to 37B), in that the web camera 30 is incorporated in the portable information terminal 34, and the portable information terminal 34 is constructed integrally with the web camera 30.

In this case, the web camera 30 captures an image of the radiation source device 16, the subject 18, and the cassette device 22, and the portable information terminal 34 displays the captured camera image on the display unit 64. Accordingly, with the twelfth modification as well, the same advantages as those of the eleventh modification can be obtained.

Figure 39:
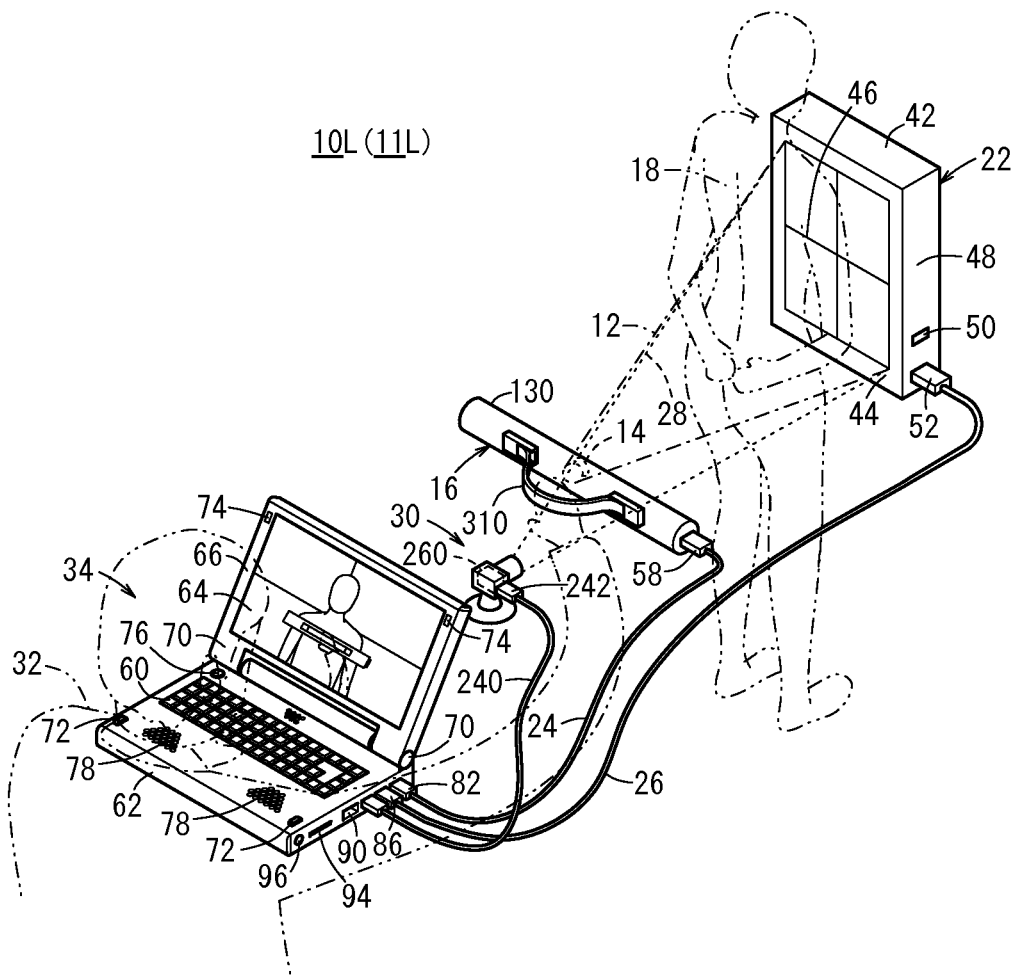
FIG. 39 is an explanatory drawing showing another configuration of the radiographic image capturing apparatus and the radiographic image capturing system of FIG. 38.

Further, with the twelfth modification, as shown in FIG. 39, a separate web camera 30 may be connected electrically with the portable information terminal 34 via a USB cable 240, whereby the web camera 30 and the portable information terminal are connected integrally in this manner. Even in this case, since the web camera 30 captures an image of the radiation source device 16, the subject 18, and the cassette device 22, and transmits the camera image to the portable information terminal 34 by way of the USB cable 240, the same advantages as those of the modification shown in FIG. 38 can be obtained. Further, similar to the case of the third modification (see FIG. 19), the web camera 30 can be arranged independently at any desired position within the range allowed by the length of the USB cable 240, and therefore, in this case as well, the degree of freedom in positioning the web camera 30 can be enhanced.

Thirteenth Modification

Figure 40:
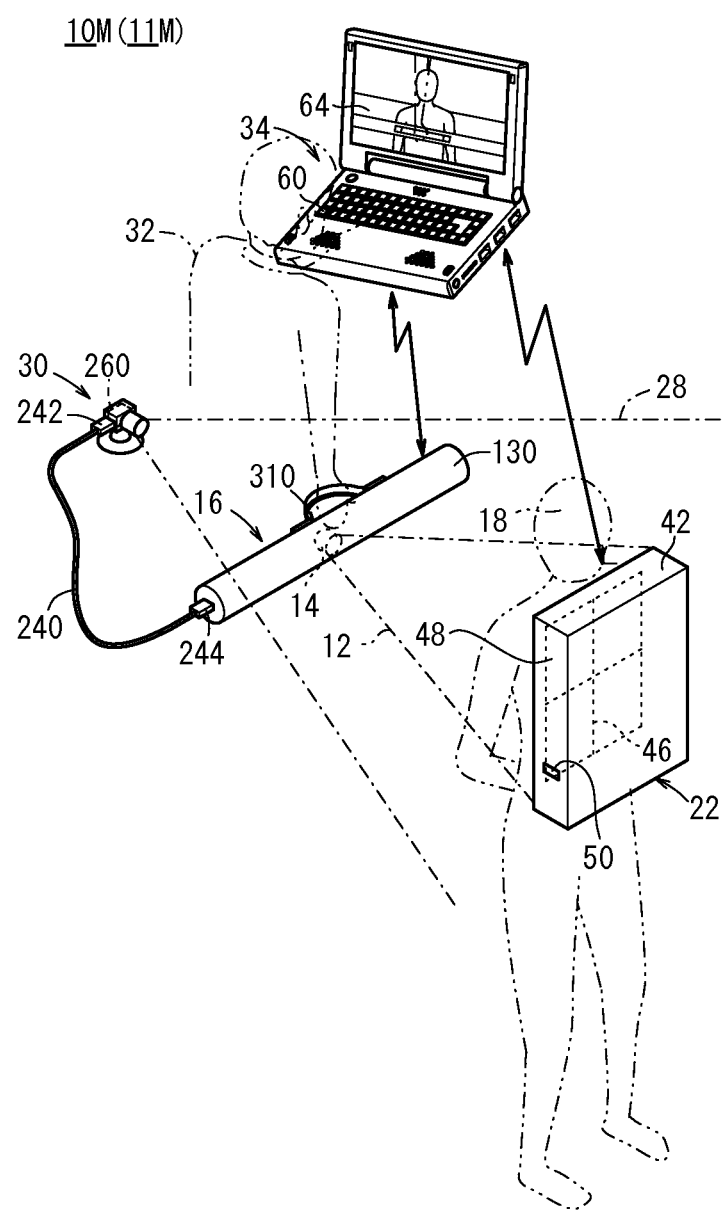
FIG. 40 is a partial structural drawing of a radiographic image capturing apparatus and a radiographic image capturing system according to a thirteenth modification.

As shown in FIG. 40, a radiographic image capturing apparatus 10M and a radiographic image capturing system 11M according to a thirteenth modification differ from the eleventh modification (see FIGS. 34 to 37B) and the twelfth modification (see FIGS. 38 and 39), in that a separate web camera 30 is connected electrically to the radiation source device 16 via a USB cable 240, and the web camera 30 and the radiation source device 16 are connected together integrally in this manner.

In this case, the web camera 30 captures an image of the radiation source device 16, the subject 18, and the cassette device 22, transmits a camera image to the radiation source device 16 via the USB cable 240, and the radiation source device 16 transfers the camera image to the portable information terminal 34 by way of wireless communications. Accordingly, the portable information terminal 34 displays the transferred camera image on the display unit 64. Thus, even in the case of the thirteenth modification, the same effects and advantages as those of the eleventh modification and the twelfth modification can be obtained. Further, as in the third modification (see FIG. 19) and the twelfth modification (see FIG. 39), because the web camera 30 can be arranged independently at any desired position within the range allowed by the length of the USB cable 240, the degree of freedom in positioning the web camera 30 can be increased also in this case.

Incidentally, in the thirteenth modification, a camera image may be transmitted directly to the portable information terminal 34 from the web camera 30 by use of wireless communications.

Fourteenth Modification

Figure 41A:
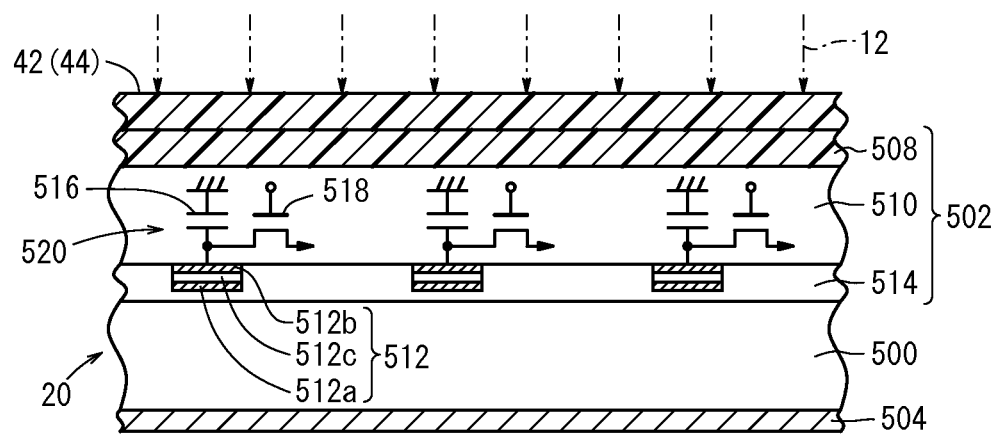
FIG. 41A is an outline explanatory drawing showing schematically an internal structure of a cassette device according to a fourteenth modification.
Figure 41B:
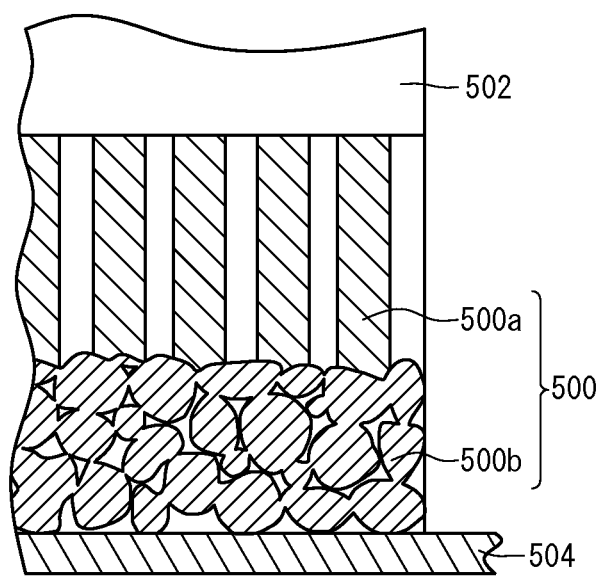
FIG. 41B is an outline explanatory drawing showing schematically and by way of example a scintillator shown in FIG. 41A.

In each of the radiographic image capturing apparatus 10, 10A through 10M (radiographic image capturing systems 11, 11A through 11M), the radiation detector 20 may be constructed as shown in FIGS. 41A and 41B (fourteenth modification). According to the fourteenth modification, a specific structure of the radiation detector, which comprises a scintillator of CsI, will be described in detail below.

According to the fourteenth modification shown in FIGS. 41A and 41B, the radiation detector 20 includes a scintillator 500 for converting radiation 12 that has passed through the subject 18 (see FIGS. 1 through 4, 10, 17 through 31A, 32A, 34, 36A, 36B, and 38 through 40) into visible light (absorbing radiation 12 and emitting visible light), and a radiation detector 502 for converting visible light generated by the scintillator 500 into electric signals (electric charges) depending on a radiographic image. In FIGS. 41A and 41B, the grid 162 and the lead plate 164 (see FIGS. 3, 4, 7, 31A, 32A, 36A and 36B) are omitted from illustration.

As shown in FIGS. 41A and 41B, the radiation detector 20 may be a face-side readout type, i.e., and ISS (Irradiation Side Sampling) type, which includes the radiation detector 502 and the scintillator 500 arranged successively with respect to the irradiated surface 44 that is irradiated with radiation 12, or a reverse-readout type, i.e., a PSS (Penetration Side Sampling) type, which includes the scintillator 500 and the radiation detector 502 arranged successively with respect to the irradiated surface 44.

The scintillator 500 emits stronger light from the irradiated surface 44, which is irradiated with radiation 12. According to an ISS type, the light emission position of the scintillator 500 is closer to the radiation detector 502. Therefore, the ISS type allows the captured radiographic image to exhibit higher resolution, while also allowing the radiation detector 502 to detect a greater amount of visible light than a PSS type. The ISS type is thus effective to increase the sensitivity of the radiation detector 20 (cassette device 22) higher than that of a PSS type.

The scintillator 500 may be made of a material such as CsI:Tl (cesium iodide with added thallium), CsI:Na (sodium-activated cesium iodide), GOS ($Gd_2O_2S$:Tb), or the like.

FIG. 41B shows by way of example a scintillator 500, which includes a columnar crystalline region formed by evaporating a material containing CsI on an evaporated substrate 504.

More specifically, the scintillator 500 shown in FIG. 41B includes a columnar crystalline region of columnar crystals 500a near the irradiated surface 44 (the radiation detector 502) to which radiation 12 is applied, and a non-columnar crystalline region of non-columnar crystals 500b positioned remotely from the irradiated surface 44. The evaporated substrate 504 preferably is made of a highly heat resistant material, e.g., aluminum (Al), in light of its low cost. The columnar crystals 500a have an average diameter, which is substantially uniform along the longitudinal directions of the columnar crystals 500a.

As described above, the scintillator 500 is made up of the columnar crystalline region (columnar crystals 500a) and the non-columnar crystalline region (non-columnar crystals 500b), in which the columnar crystalline region, which comprises columnar crystals 500a that are capable of emitting light highly efficiently, is disposed near the radiation detector 502. Therefore, visible light generated by the scintillator 500 travels through the columnar crystals 500a and is emitted toward the radiation detector 502. As a result, visible light emitted toward the radiation detector 502 is prevented from scattering, which in turn prevents the radiographic image detected by the cassette device 22 from becoming blurred. Visible light that has reached a deeper region (non-columnar crystalline region) of the scintillator 500 is reflected toward the radiation detector 502 by the non-columnar crystals 500b. Consequently, the amount of visible light that is applied to the radiation detector 502 (the efficiency at which visible light emitted by the scintillator 500 is detected) can be increased.

If it is assumed that the thickness of the columnar crystalline region of the scintillator 500, which is positioned near the irradiated surface 44, is represented by t1, whereas the thickness of the non-columnar crystalline region of the scintillator 500, which is positioned near the evaporated substrate 504, is represented by t2, then the thicknesses t1, t2 preferably satisfy the relationship $0.01 \leq t2/t1 \leq 0.25$.

Since the thickness t1 of the columnar crystalline region and the thickness t2 of the non-columnar crystalline region satisfy the above relationship, the ratio along thickness-wise directions of the scintillator 500 between the region (columnar crystalline region), which has high light emission efficiency to prevent visible light from being scattered, and the region (non-columnar crystalline region), which reflects visible light, is in an appropriate range for increasing light emission efficiency of the scintillator 500, and the efficiency at which the visible light emitted by the scintillator 500 is improved, together with enhancing the resolution of the radiographic image.

If the thickness t2 of the non-columnar crystalline region is too large, then a region with low light emission efficiency increases, resulting in a reduction in sensitivity of the cassette device 22. Therefore, the ratio (t2/t1) preferably is in a range from 0.02 to 0.1.

It has been described above that the scintillator 500 includes the columnar crystalline region and the non-columnar crystalline region in a continuous array. However, the scintillator 500 may include the columnar crystalline region and a light reflecting layer of Al or the like, which replaces the non-columnar crystalline region.

The radiation detector 502 serves to detect visible light emitted from the light emission side (columnar crystal 500a) of the scintillator 500. As shown in FIG. 41A, the radiation detector 502 includes an insulating substrate 508, a TFT layer 510, and photoelectric transducers 512, which are successively deposited on the irradiated surface 44 along the direction in which radiation 12 is applied. A planarization layer 514 is disposed in covering relation to the photoelectric transducers 512 on the bottom surface of the TFT layer 510.

Further, the radiation detector 502 is constructed as a TFT active matrix board (hereinafter referred to as a "TFT board") having a matrix of pixels 520 as viewed in plan on the insulating substrate 508. Each of the pixels 520 includes one of the photoelectric transducers 512, which may comprise a photodiode (PD) or the like, a storage capacitor 516, and a TFT 518.

The TFT 518 corresponds to the TFT 188 (see FIG. 9) described above, and the photoelectric transducer 512 and the storage capacitor 516 correspond to a pixel 180.

The photoelectric transducer 512 comprises a lower electrode 512a near the scintillator 500, an upper electrode 512b near the TFT layer 510, and a photoelectric conversion film 512c disposed between the lower electrode 512a and the upper electrode 512b. The photoelectric conversion film 512c absorbs visible light emitted from the scintillator 500, and generates electric charges depending on the absorbed visible light.

The lower electrode 512a preferably is made of an electrically conductive material, which is transparent at least to the wavelength of light emitted by the scintillator 500, because the lower electrode 512a needs to apply visible light emitted by the scintillator 500 to the photoelectric transducer 512. More specifically, it is preferable to make the lower electrode 512a of a transparent conducting oxide (TCO), which is highly permeable to visible light and has a low resistance value.

Although the lower electrode 512a may be made of a thin metal film of Au or the like, preferably, the lower electrode 512a is made of TCO, because the resistance value of a thin metal film of Au or the like tends to increase if the thin metal film has a light transmittance of 90% or higher. For example, the lower electrode 512a may be made of ITO (Indium Tin Oxide), IZO (Indium Zinc Oxide), AZO (Aluminum-doped Zinc Oxide), FTO (Fluorine-doped Tin Oxide), $SnO_2$, $TiO_2$, $ZnO_2$, or the like. However, most preferably, the lower electrode 512a is made of ITO in light of processing simplicity, low resistance, and transparency. The lower electrode 512a may be a single electrode shared by all of the pixels 520, or may be divided into a plurality of electrodes assigned to each of the pixels 520 respectively.

Further, the photoelectric conversion film 512c may be made of a material that absorbs visible light and generates electric charges. For example, the photoelectric conversion film 512c may be made of amorphous silicon (a-Si), or an organic photoelectric conversion material (OPC). If the photoelectric conversion film 512c is made of amorphous silicon, the photoelectric conversion film 512c can absorb visible light emitted from the scintillator 500 in a wide wavelength range. However, since a photoelectric conversion film 512c made of amorphous silicon needs to be evaporated, heat resistance of the insulating substrate 508 should be taken into consideration if the insulating substrate 508 is made of synthetic resin.

If the photoelectric conversion film 512c is made of a material including an organic photoelectric conversion material, then the photoelectric conversion film 512c provides an absorption spectrum, which exhibits a high absorption rate mainly in the visible range, and hence does not absorb electromagnetic waves other than visible light emitted by the scintillator 500. Therefore, noise produced if radiation 12 such as X-rays, γ-rays, or the like is absorbed by the photoelectric conversion film 512c can be minimized.

The photoelectric conversion film 512c, which is made of an organic photoelectric conversion material, can be formed by applying an organic photoelectric conversion material to a target using a liquid droplet ejection head such as an ink jet head or the like. Therefore, the target does not need to be heat resistant. According to the fourteenth modification, the photoelectric conversion film 512c is made of an organic photoelectric conversion material.

The photoelectric conversion film 512c, which is made of an organic photoelectric conversion material, absorbs almost no radiation 12. Therefore, in an ISS type of radiation detector 20 having the radiation detector 502 arranged to pass radiation 12 therethrough, attenuation of radiation 12 that has passed through the radiation detector can be reduced, thereby minimizing a reduction in sensitivity to radiation 12. Therefore, it is preferable for the photoelectric conversion film 512c to be made of an organic photoelectric conversion material, particularly if the radiation detector 20 is of an ISS type.

In order for the organic photoelectric conversion material of the photoelectric conversion film 512c to absorb visible light emitted by the scintillator 500 most efficiently, the absorption peak wavelength thereof should preferably be as close as possible to the light emission peak wavelength of the scintillator 500. Although the absorption peak wavelength of the organic photoelectric conversion material and the light emission peak wavelength of the scintillator 500 ideally are in agreement with each other, it is possible to sufficiently absorb light emitted by the scintillator 500 if the difference between the absorption peak wavelength and the light emission peak wavelength is small enough. More specifically, the difference between the absorption peak wavelength of the organic photoelectric conversion material and the light emission peak wavelength of the scintillator 500 with respect to the radiation 12 preferably is 10 nm or smaller, and more preferably, is 5 nm or smaller.

Organic photoelectric conversion materials that meet the above requirements include quinacridone-based organic compounds and phthalocyanine-based organic compounds, for example. Since quinacridone, for example, has an absorption peak wavelength of 560 nm in the visible range, if quinacridone is used as the organic photoelectric conversion material and CsI:Tl is used as the material of the scintillator 500, the difference between the above peak wavelengths can be reduced to 5 nm or smaller, thus making it possible to substantially maximize the quantity of electric charges generated by the photoelectric conversion film 512c.

The photoelectric conversion film 512c, which is applicable to the radiation detector 20, will be described in specific detail below.

The radiation detector 20 includes an electromagnetic wave absorption/photoelectric conversion region provided by an organic layer, including the upper electrode 512b and the lower electrode 512a, and the photoelectric conversion film 512c sandwiched between the upper electrode 512b and the lower electrode 512a. The organic layer may be formed by superposition or mixture of an electromagnetic wave absorption region, a photoelectric conversion region, an electron transport region, a hole transport region, an electron blocking region, a hole blocking region, a crystallization prevention region, an electrode, and an interlayer contact improving region, etc.

The organic layer preferably includes an organic p-type compound or an organic n-type compound. An organic p-type semiconductor (compound) is a donor organic compound typified mainly by a hole transport organic compound, and refers to an organic compound that tends to donate electrons. More specifically, in a case where two organic materials are placed in contact with each other, one of the organic materials, which has a lower ionization potential, is referred to as a donor organic compound. Any type of organic compound which is capable of donating electrons can be used as a donor organic compound. An organic n-type semiconductor (compound) is an acceptor organic compound typified mainly by an electron transport organic compound, and refers to an organic compound that tends to accept electrons. More specifically, in a case where two organic materials are placed in contact with each other, one of the organic materials, which has a larger electron affinity, is referred to as an acceptor organic compound. Any type of organic compound which is capable of accepting electrons can be used as an acceptor organic compound.

Materials that can be used as the organic p-type semiconductor and the organic n-type semiconductor, and arrangements of the photoelectric conversion film 512c are disclosed in detail in Japanese Laid-Open Patent Publication No. 2009-032854, and will not be described in detail below.

The photoelectric transducer 512 of each pixel may include at least the upper electrode 512b, the lower electrode 512a, and the photoelectric conversion film 512c. For preventing dark current from increasing, the photoelectric transducer 512 preferably includes at least one of an electron blocking film and a hole blocking film, and more preferably, includes both the electron blocking film and the hole blocking film.

The electron blocking film may be disposed between the upper electrode 512b and the photoelectric conversion film 512c. If a bias voltage is applied between the upper electrode 512b and the lower electrode 512a, the electron blocking film can prevent electrons from being injected from the upper electrode 512b into the photoelectric conversion film 512c, thereby preventing dark current from increasing. The electron blocking film may be made of an organic material that can donate electrons. The electron blocking film actually is made of a material which is selected depending on the material of the adjacent electrode and the material of the adjacent photoelectric conversion film 512c. A preferable material has an electron affinity (Ea), which is at least 1.3 eV greater than the work function (Wf) of the material of the adjacent electrode, and an ionization potential (Ip) equal to or smaller than the Ip of the material of the adjacent photoelectric conversion film 512c. Materials that can be used as an organic material and which are capable of donating electrons are disclosed in detail in Japanese Laid-Open Patent Publication No. 2009-032854, and such materials will not be described in detail below.

The thickness of the electron blocking film preferably is in the range from 10 nm to 200 nm, more preferably, is in the range from 30 nm to 150 nm, and particularly preferably, is in the range from 50 nm to 100 nm, in order to reliably achieve a dark current reducing capability and to prevent the photoelectric conversion efficiency of the photoelectric transducer 512 from being lowered.

The hole blocking film may be disposed between the photoelectric conversion film 512c and the lower electrode 512a. In the case that a bias voltage is applied between the upper electrode 512b and the lower electrode 512a, the hole blocking film can prevent holes from being injected from the lower electrode 512a into the photoelectric conversion film 512c, thereby preventing dark current from increasing. The hole blocking film may be made of an organic material capable of accepting electrons. The hole blocking film actually is made of a material, which is selected depending on the material of the adjacent electrode and the material of the adjacent photoelectric conversion film 512c. A preferable material should have an ionization potential (Ip), which is at least 1.3 eV greater than the work function (Wf) of the material of the adjacent electrode, and an electron affinity (Ea), which is equal to or greater than the Ea of the material of the adjacent photoelectric conversion film 512c. Materials that can be used as an organic material and which can accept electrons are disclosed in detail in Japanese Laid-Open Patent Publication No. 2009-032854, and such materials will not be described in detail below.

The thickness of the hole blocking film preferably is in the range from 10 nm to 200 nm, more preferably, is in the range from 30 nm to 150 nm, and particularly preferably, is in the range from 50 nm to 100 nm, in order to reliably achieve a dark current reducing capability and to prevent the photoelectric conversion efficiency of the photoelectric transducer 512 from being lowered.

For setting a bias voltage to move holes, which exist among the electric charges generated in the photoelectric conversion film 512c, toward the lower electrode 512a, and to move electrons, which exist among the electric charges generated in the photoelectric conversion film 512c, toward the upper electrode 512b, the electron blocking film and the hole blocking film may be switched in position. Both the electron blocking film and the hole blocking film are not necessarily required, and either one of them may be included to provide a certain dark current reducing capability.

Each of the TFTs 518 of the TFT layer 510 includes a stacked assembly of a gate electrode, a gate insulating film, and an active layer (channel layer). A source electrode and a drain electrode are disposed on the active layer and are spaced from each other with a gap therebetween. The active layer may be made of any one of amorphous silicon, an amorphous oxide, an organic semiconductor material, and carbon nanotubes. However, the active layer is not limited to being made from such materials.

Amorphous oxide, which the active layer may be made of, preferably is an oxide (e.g., In—O oxide) including at least one of In, Ga, and Zn, more preferably, is an oxide (e.g., In—Zn—O oxide, In—Ga oxide, or Ga—Zn—O oxide) including at least two of In, Ga, and Zn, and particularly preferably, is an oxide including In, Ga, and Zn. An In—Ga-An-O amorphous oxide preferably is an amorphous oxide the crystalline composition of which is represented by $InGaO_3(ZnO)_m$ where m represents a natural number smaller than 6, and particularly preferably, is $InGaZnO_4$. The amorphous oxide, which the active layer may be made of, is not limited to these materials.

The organic semiconductor material, which the active layer may be made of, preferably is a phthalocyanine compound, pentacene, vanadyl phthalocyanine, or the like, but is not limited to these materials. The composition of such a phthalocyanine compound is disclosed in detail in Japanese Laid-Open Patent Publication No. 2009-212389, and will not be described in detail below.

If the active layer of each of the TFTs 518 is made of one of an amorphous oxide, an organic semiconductor material, and carbon nanotubes, then the active layer is effective at reducing noise generated in the radiation detector 502, because the active layer does not absorb radiation 12 such as X-rays, or absorbs only an extremely small amount of radiation 12.

If the active layer is made of carbon nanotubes, then the TFTs 518 can have a high switching speed and exhibit a low absorption rate for visible light in the TFTs 518. If the active layer is made of carbon nanotubes, since the performance of the TFTs 518 could be greatly degraded by trace metal impurities mixed therewith, it is necessary to separate and extract highly pure carbon nanotubes using a centrifugal separator or the like.

Films made of an organic photoelectric conversion material, and films made of an organic semiconductor material are sufficiently flexible. If the photoelectric conversion film 512c, which is made of an organic photoelectric conversion material, and the TFTs 518, the active layer of which is made of an organic semiconductor, are combined, then the radiation detector 502, on which the weight of the subject 18 is applied as a load, does not necessarily need to be made highly rigid.

The insulating substrate 508 may be made of any material insofar as the material is permeable to light and does not absorb a significant amount of radiation 12. The amorphous oxide of the active layer of the TFTs 518 and the organic photoelectric conversion material of the photoelectric conversion film 512c of the photoelectric transducer 512 can be deposited as films at low temperatures. Therefore, the insulating substrate 508 is not limited to a highly heat-resistant substrate, such as a semiconductor substrate, a quartz substrate, a glass substrate, or the like, but may be a flexible substrate made of synthetic resin, a substrate of aramid fibers, or a substrate of bionanofibers. More specifically, the insulating substrate 508 may be a flexible substrate made of polyester such as polyethylene terephthalate, polybutylene phthalate, polyethylene naphthalate, or the like, polystyrene, polycarbonate, polyethersulfone, polyarylate, polyimide, polycycloolefine, norbornene resin, poly(chlorotrifluoroethylene), or the like. A flexible substrate made of plastic enables the radiation detector 20 to be light in weight and hence easy to carry around. The insulating substrate 508 may include an insulating layer for making the insulating substrate 508 electrically insulative, a gas barrier layer for making the insulating substrate 508 impermeable to water and oxygen, and an undercoat layer for making the insulating substrate 508 flat or to facilitate intimate contact with the electrode.

Since a high-temperature process at 200 degrees Celsius may be applied to aramid fibers, aramid fibers allow a transparent electrode material to be set at a high temperature for providing lower resistance. Such aramid fibers also allow driver ICs to be automatically mounted thereon by a process including a solder reflow process. Furthermore, inasmuch as aramid fibers have a coefficient of thermal expansion close to ITO and glass, an insulating substrate made of aramid fibers is less liable to warp and crack after fabrication. In addition, an insulating substrate made of aramid fibers may be made thinner than a glass substrate or the like. Such an insulating substrate 508 may be in the form of a stacked assembly made of an ultrathin glass substrate together with aramid fibers.

Bionanofibers are made by compounding a bundle of cellulose microfibrils (bacteria cellulose) produced by bacteria (acetic acid bacteria, *Acetobacter Xylinum*) and a transparent resin. The bundle of cellulose microfibrils has a width of 50 nm, which is 1/10 of the wavelength of visible light, is highly strong and highly resilient, and is subject to low thermal expansion. Bionanofibers that contain 60% to 70% fibers and which exhibit a light transmittance of about 90% at a wavelength of 500 nm can be produced by impregnating bacteria cellulose with a transparent resin such as an acrylic resin, an epoxy resin, or the like, and setting the transparent resin. In addition to being flexible, bionanofibers have a low coefficient of thermal expansion ranging from 3 ppm to 7 ppm, which is comparable to silicon crystals, a high strength of 460 MPa that matches the strength of steel, and a high resiliency of 30 GPa. Therefore, an insulating substrate 508 made of bionanofibers can be thinner than glass substrates or the like.

If a glass substrate is used as the insulating substrate 508, then the radiation detector 502 (TFT substrate) has an overall thickness of about 0.7 mm, for example. According to the fourteenth modification, the insulating substrate 508 comprises a thin substrate made of a light-permeable synthetic resin in order to make the cassette device 22 thinner. The overall thickness of the insulating substrate 508 is reduced to about 0.1 mm, thereby making the radiation detector 502 flexible. The radiation detector 502, which is made flexible in this manner, increases the shock resistance of the cassette device 22, such that the radiation detector 502 is less liable to break even if the cassette device 22 is subjected to shocks. Plastic resins, aramid fibers, bionanofibers, etc., do not absorb radiation 12 significantly. Thus, if the insulating substrate 508 is made of any of the aforementioned materials, the amount of radiation 12 absorbed by the insulating substrate 508 can be reduced. Consequently, even though radiation 12 passes through an ISS type of radiation detector 502, a reduction in sensitivity to radiation 12 is minimized.

The insulating substrate 508 of the cassette device 22 need not necessarily comprise a substrate of synthetic resin, but may be a substrate made of another material, such as a glass substrate or the like.

A planarization layer 514 for planarizing the radiation detector 502 is disposed on a side of the radiation detector 502 (TFT substrate), which is remote from the side (near the scintillator 500) to which radiation 12 is applied.

According to the fourteenth modification, the radiation detector 20 may be constructed in the following ways.

(1) The photoelectric transducer 512 including the PD may be made of an organic photoelectric conduction material, and the TFT layer 501 may comprise CMOS sensors. Since only the PD is made of an organic material, the TFT layer 510 including the CMOS sensors is not required to be flexible. The photoelectric transducer 512, which is made of an organic photoelectric conduction material, and the CMOS sensors are disclosed in Japanese Laid-Open Patent Publication No. 2009-212377, and will not be described in detail below.

(2) The photoelectric transducer 512 including the PD may be made of an organic photoelectric conduction material, and the TFT layer 501, which is flexible, may comprise a CMOS circuit having TFTs made of an organic material. Pentacene may be used as a p-type organic semiconductor material used in the CMOS circuit, and cupric fluoride phthalocyanine ($F_{16}CuPc$) may be used as an n-type organic semiconductor material. Thus, the TFT layer 510 is made flexible enough to achieve a smaller radius of curvature. With the TFT layer 510 being constructed in this manner, the gate insulating film may be made significantly thinner for thereby reducing the drive voltage. The gate insulating film, the semiconductor, and the electrodes may be fabricated at room temperature or at a temperature of 100° C. or lower. The CMOS circuit may be fabricated directly on the flexible insulating substrate 508. The TFTs, which are made of an organic material, can be microfabricated by a fabrication process according to a scaling law. The insulating substrate 508 can be formed as a flat substrate that is free of surface irregularities by coating a thin polyimide substrate with a polyimide precursor according to a spin-coating process, and heating the coated substrate to change the polyimide precursor into polyimide.

(3) The PDs and TFTs, which are made of crystalline Si, may be disposed on a resin insulating substrate 508 according to a fluidic self-assembly process for placing a plurality of micron order device blocks in given positions on a substrate. More specifically, the PDs and TFTs as minute device blocks on a micron order are fabricated on another substrate, and then are cut off from the substrate. Then, the PDs and TFTs are scattered over the insulating substrate 508 as a target substrate and placed statistically thereon. The insulating substrate 508 is processed to match the device blocks, so that the device blocks can selectively be placed on the insulating substrate 508. Therefore, optimum device blocks (PDs and TFTs), which are made of an optimum material, can be integrated on an optimum substrate (insulating substrate 508). Therefore, it is possible to integrate PDs and TFTs on a non-crystalline insulating substrate 508 (resin substrate).

Other Arrangements of the Present Exemplary Embodiment

It is a matter of course that the present embodiment is not limited to the arrangements described above.

More specifically, the radiographic image capturing apparatus 10, 10A through 10M, and the radiographic image capturing systems 11, 11A through 11M, which include the various configurations described above, may also adopt the following configurations listed below.

(1) A structure may be adopted having the radiation source device 16, the cassette device 22, the web camera 30, and the portable information terminal 34, in which the radiation source device 16 and the portable information terminal 34 are constituted separately from each other, and the web camera 30 is incorporated in the portable information terminal 34 (see FIGS. 1 through 17, and FIGS. 20, 22, 25 and 38).

Figure 34:
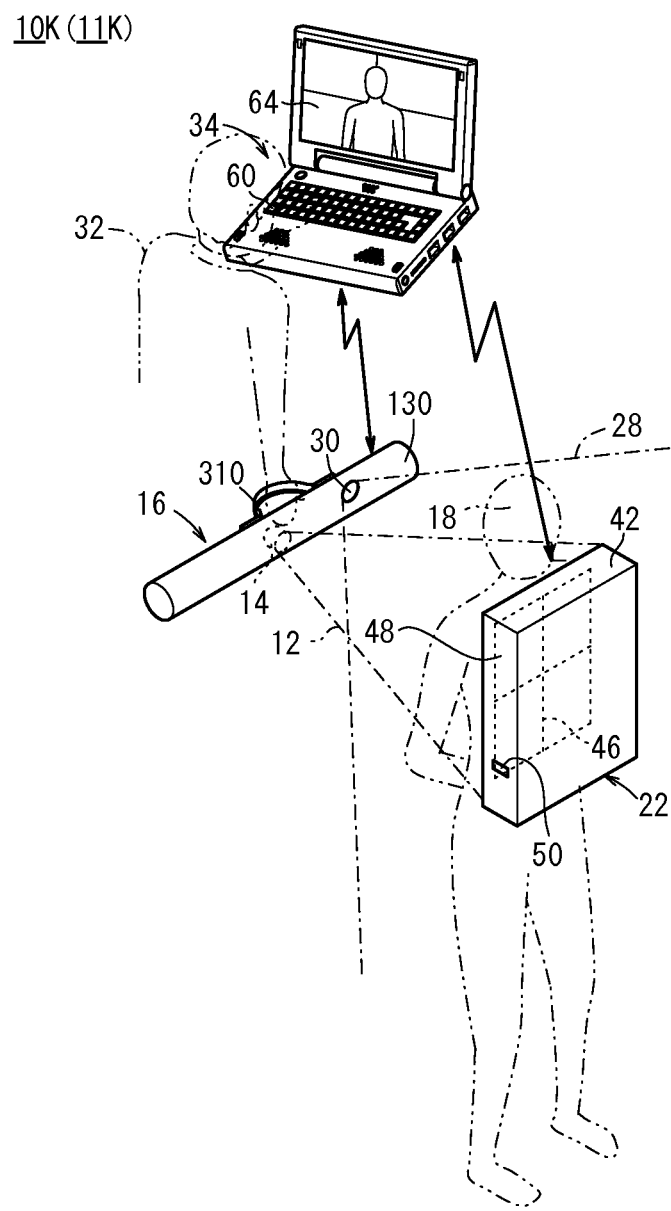
FIG. 34 is a partial structural drawing of a radiographic image capturing apparatus and a radiographic image capturing system according to an eleventh modification.

(2) A structure may be adopted having the radiation source device 16, the cassette device 22, the web camera 30, and the portable information terminal 34, in which the radiation source device 16 and the portable information terminal 34 are constituted separately from each other, and the web camera 30 is incorporated in the radiation source device 16 (see FIGS. 18 and 34).

(3) A structure may be adopted having the radiation source device 16, the cassette device 22, the web camera 30, and the portable information terminal 34, in which the radiation source device 16 and the portable information terminal 34 are constituted separately from each other, and the portable information terminal 34 and the web camera 30 are connected integrally via the USB cable 240 (see FIGS. 19 and 39).

(4) A structure may be adopted having the radiation source device 16, the cassette device 22, the web camera 30, and the portable information terminal 34, in which the radiation source device 16 and the portable information terminal 34 are constituted separately from each other, and the radiation source device 16 and the web camera 30 are connected integrally via the USB cable 240 (see FIG. 40).

(5) A structure may be adopted having the radiation source device 16, the cassette device 22, the web camera 30, and the portable information terminal 34, in which the radiation source device 16 and the portable information terminal 34 are constituted separately from each other, and the web camera 30 also is constituted separately from the radiation source device 16, the cassette device 22, and the portable information terminal 34.

(6) A structure may be adopted having the radiation source device 16, the cassette device 22, the web camera 30, and the portable information terminal 34, in which the radiation source device 16 and the portable information terminal 34 are constructed integrally, and the web camera 30 is incorporated in the portable information terminal 34 (see FIG. 21).

(7) A structure may be adopted having the radiation source device 16, the cassette device 22, the web camera 30, and the portable information terminal 34, in which the radiation source device 16 and the portable information terminal 34 are constructed integrally, and the web camera 30 is incorporated in the radiation source device 16.

(8) A structure may be adopted having the radiation source device 16, the cassette device 22, the web camera 30, and the portable information terminal 34, in which the radiation source device 16 and the portable information terminal 34 are constructed integrally, and the web camera 30 is constituted separately from the radiation source device 16, the cassette device 22, and the portable information terminal 34.

(9) A structure may be adopted having the radiation source device 16, the cassette device 22, and the web camera 30, and in which the radiation source device 16 and the web camera 30 are constituted separately from each other (see FIG. 23).

(10) A structure may be adopted having the radiation source device 16, the cassette device 22, and the web camera 30, and in which the radiation source device 16 and the web camera 30 are constructed integrally with each other (see FIGS. 24, 31A and 32A).

In addition, in the foregoing configurations (1) through (10), in the case that the communication unit 136 of the radiation source device 16, the communication unit 170 of the cassette device 22, (the communication unit 218 of the portable information terminal 34, the communication unit 262 of the high-voltage power supply 252), and the communication unit 260 of the web camera 30 are provided, the camera image captured by the web camera 30 may be transmitted from any one of such communication units, including the communication unit 260 of the web camera 30, to the communication unit 104 of the medical organization 40 via the network 36. In other words, any one of such communication units functions as a web camera communication unit for transmitting the camera image.

Further, in configurations (1) through (10), in the case that the communication unit 136 of the radiation source device 16, the communication unit 170 of the cassette device 22, (the communication unit 218 of the portable information terminal 34, the communication unit 262 of the high-voltage power supply 252), and the communication unit 260 of the web camera 30 are provided, the radiographic image output from the radiation detector 20 may be transmitted from any one of such communication units, including the communication unit 260 of the web camera 30, to the communication unit 104 of the medical organization 40 via the network 36.

Accordingly, in configurations (1) through (10), in the event that the communication unit 136 of the radiation source device 16, the communication unit 170 of the cassette device 22, (the communication unit 218 of the portable information terminal 34, the communication unit 262 of the high-voltage power supply 252), and the communication unit 260 of the web camera 30 are provided, transmission and reception of signals via the network 36 between the radiographic image capturing apparatus 10, 10A through 10M and the communication unit 104 of the medical organization 40 can be carried out between the communication unit 104 and any one of the other communication units, including the communication unit 260 of the web camera 30.

Furthermore, in the above exemplary embodiments, signals are sent and received by way of at least one of wireless communications and wired communications. However, if the subject 18 is held in contact with the radiation source device 16 and the cassette device 22 with a short SID, then signals (e.g., a synchronization control signal) may be sent and received between the radiation source device 16 and the cassette device 22 by way of intrabody communications through the subject 18. Further, as in the case of modifications 11 through 13 (see FIGS. 34 through 40), if the operator 32 is held in contact with both the radiation source device 16 and the portable information terminal 34, then signals may be sent and received between the radiation source device 16 and the portable information terminal 34 by way of intrabody communications through the operator 32.

The present invention is not limited to the above exemplary embodiments, and it is a matter of course that various additional or alternative arrangements may be adopted without departing from the scope of the invention.

The invention claimed is:

1. A radiographic image capturing apparatus comprising:
a radiation source for outputting radiation;
a camera; and
a display unit;
wherein the radiographic image capturing apparatus includes:
a first surface that includes
a permeation surface from which the radiation source outputs the radiation, and
an image capturing surface from which the camera captures an image;

a second surface that includes a display surface on which the display unit displays at least the image captured by the camera; and a portable information terminal which is made integral with the radiation source, the portable information terminal incorporating therein the camera and the display unit, wherein the portable information terminal is a controller that controls the radiation source, wherein the camera and the display unit are accommodated in a housing of the controller, and wherein one surface of the housing is constructed as the first surface and another surface of the housing is constructed as the second surface.

2. The radiographic image capturing apparatus according to claim 1, further comprising:

a radiation detector that detects the radiation output from the radiation source and converts the radiation into a radiographic image; and a cassette device that is permeable to the radiation and accommodates the radiation detector, wherein the camera captures at least an image of the cassette device, and the display unit displays the image of the cassette device captured by the camera.

3. The radiographic image capturing apparatus according to claim 2, wherein the camera captures an image of an irradiation surface of the cassette device, the irradiation surface facing the permeation surface and being irradiated with the radiation, and the display unit displays the image of the irradiation surface captured by the camera.

4. The radiographic image capturing apparatus according to claim 3, wherein in a case where a subject is placed between the first surface and the irradiation surface and is positioned such that a region to be imaged of the subject is inside an irradiated field of the radiation, the camera captures an image of the subject and the irradiation surface, and the display unit display the image of the irradiation surface within which the subject is visible.

5. The radiographic image capturing apparatus according to claim 2, wherein the camera captures a moving image or a still image of the cassette device.

6. The radiographic image capturing apparatus according to claim 5, wherein the camera is an optical camera.

7. The radiographic image capturing apparatus according to claim 1, wherein rotating the display unit about a shaft causes the display surface to be rotated through a desired angle.

8. The radiographic image capturing apparatus according to claim 2, wherein a first communication unit that communicates with the exterior is housed in the housing, a second communication unit that communicates with the exterior is housed in the cassette device, the second communication unit transmits the radiographic image to the first communication unit by at least one of wireless communications and wired communications, and the display unit displays the radiographic image received by the first communication unit.

9. The radiographic image capturing apparatus according to claim 2, wherein the controller further controls the cassette device.

10. The radiographic image capturing apparatus according to claim 2, wherein the cassette device is portable.

* * * * *